(12) United States Patent
Hsieh et al.

(10) Patent No.: US 7,964,700 B2
(45) Date of Patent: Jun. 21, 2011

(54) INHIBITORS OF TASPASE1 PROTEASE ACTIVITY

(75) Inventors: James J. D. Hsieh, Ladue, MO (US); Stanley J. Korsmeyer, Weston, MA (US); Susan Korsmeyer, legal representative, Weston, MA (US); Emily H. Y. Cheng, Ladue, MO (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 182 days.

(21) Appl. No.: 11/851,301

(22) Filed: Sep. 6, 2007

(65) Prior Publication Data

US 2008/0177034 A1    Jul. 24, 2008

Related U.S. Application Data

(62) Division of application No. 10/974,127, filed on Oct. 26, 2004, now abandoned.

(60) Provisional application No. 60/515,187, filed on Oct. 27, 2003.

(51) Int. Cl.
*C07K 4/00* (2006.01)
(52) U.S. Cl. ...................................................... 530/300
(58) Field of Classification Search ........................ None
See application file for complete search history.

(56) References Cited

U.S. PATENT DOCUMENTS 6,872,560 B1 * 3/2005 Yue et al. ...................... 435/226

FOREIGN PATENT DOCUMENTS

EP          1488480        1/2005
WO     WO/01/16334   *    3/2001

OTHER PUBLICATIONS

A_Geneseq_200907 database Acc. No. ABB56765, from Shimkets et al WO/01/038586. Alignment with SEQ ID No. 7.*
Bullock et al, Peptide Aldehyde Complexes with Wheat Serine Carboxypeptidase II. Journal of Molecular Biology vol. 255, Issue 5, Feb. 9, 1996, pp. 714-725.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
UniProt database Acc. No. Q9SB03 May 1, 2000 from Hirano et al, Mol. Biol. Evol. 15:978-987(1998). Alignment with SED ID No. 6.*
Issued_Patents_AA database US7425335 Gore et al, 2008 SEQ ID No. 4. Alignment with SEQ ID No. 6.*
A_Geneseq_8 database Accession No. AAB67580 Yue et al. Mar. 8, 2001. Alignment with SEQ ID No. 1.
Galye et al., "Identification of regions in interleukin-1 alpha important for activity" *J. Biol. Chem.* 268(29):22105-22111 (1993).
Issued_Patents_AA database US 6,872,560 Yue et al. Mar. 29, 2005 (priority Sep. 1, 1999) SEQ ID No. 12. Alignment with SEQ ID No. 1.
Whisstock et al., "Prediction of protein function from protein sequence and structure" *Q. Rev Biophys.* 36(3):307-340 (2003).

* cited by examiner

*Primary Examiner* — Sheridan Swope
(74) *Attorney, Agent, or Firm* — Fish & Richardson P.C.

(57) ABSTRACT

A novel protease, Taspase1, is described. Taspase1 is involved in the cleavage of the myeloid/lymphoid or mixed-lineage leukemia (i.e., MLL) protein, which is required for proper HOX gene regulation. Diagnostic methods utilizing Taspase1 are provided, as well as inhibitors of Taspase1. Methods of using the inhibitors of Taspase1 are also described. For example an inhibitor of Taspase1 can be used to treat a cancer, e.g., leukemia, in a subject.

24 Claims, 23 Drawing Sheets

FIG. 1B

CS1:
```
G K G S R A E G Q V [D G A D] L S T S D E    Human MLL       (SEQ ID NO: 19)
G K R S   A E G Q V [D G A D] L S T S D E    Mouse MLL       (SEQ ID NO: 20)
R K K S   A E G Q V [D G A D] I S T S S E S  Pufferfish MLL  (SEQ ID NO: 21)
```

CS2:
```
C D L P K H S Q L  [D G V D D] G T E S D T    Human MLL             (SEQ ID NO: 22)
C L L P K H S Q L  [D G V D D] G T E S D T    Mouse MLL             (SEQ ID NO: 23)
L G K P Q H G Q L  [D G V D D] G S C H D D A  Pufferfish MLL        (SEQ ID NO: 24)
F Q M L K I H M Q M [D G V D D] H T E F G T   Anopheles trithorax   (SEQ ID NO: 25)
A A K M R H M Q L  [D G V D D] S D T E F F R  Drosophila trithorax  (SEQ ID NO: 26)
P G P A P R H E Q L [D G V D D] G E A D S E A  Human MLL2           (SEQ ID NO: 27)
```

FIG. 3C

Asparaginase_2 homology domain (positions 41–391, ending at 420)

Taspase1

| | | | | | | | |
|---|---|---|---|---|---|---|---|
| T | L | D | T | V | G | A | V V V | Homo sapiens (SEQ ID NO: 28) |
| T | L | D | T | V | G | A | V V V | Mus musculus (SEQ ID NO: 29) |
| A | L | D | T | V | G | A | V V V | Rattus norvegicus (SEQ ID NO: 30) |
| C | L | D | T | V | G | A | V V V | Fugu rubripes (SEQ ID NO: 31) |
| C | L | D | T | V | G | A | V V V | Danio rerio (SEQ ID NO: 32) |
| P | L | D | T | V | G | A | V C V | Anopheles gambiae (SEQ ID NO: 33) |
| A | L | D | T | V | G | A | V C V | Drosophila melanogaster (SEQ ID NO: 34) |

Glycosylasparaginase

| | | | | | | | |
|---|---|---|---|---|---|---|---|
| G | H | D | T | I | G | M | V V I | Homo sapiens (SEQ ID NO: 35) |
| S | H | D | T | I | G | M | V V I | Mus musculus (SEQ ID NO: 36) |
| A | H | D | T | I | G | M | I A I | Fugu rubripes (SEQ ID NO: 37) |
| N | H | D | T | I | G | M | V A V | Spodotera frugiperda (SEQ ID NO: 38) |
| N | H | D | T | I | G | M | I A L | Flavobacterium meningosepticum (SEQ ID NO: 39) |

L-Asparaginase

| | | | | | | | |
|---|---|---|---|---|---|---|---|
| N | L | G | T | V | G | A | V A L | Homo sapiens (SEQ ID NO: 40) |
| N | S | G | T | V | G | A | V A L | Mus musculus (SEQ ID NO: 41) |
| K | M | G | T | V | G | A | V A V | Fugu rubripes (SEQ ID NO: 42) |
| Q | I | G | T | V | G | C | V A V | Arabidopsis thaliana (SEQ ID NO: 43) |
| Q | I | G | T | V | G | C | V A V | Lupinus arboreus (SEQ ID NO: 44) |

(SEQ ID NO: 1)
(SEQ ID NO: 45)
(SEQ ID NO: 46)
(SEQ ID NO: 47)
(SEQ ID NO: 48)
(SEQ ID NO: 49)
(SEQ ID NO: 50)

(SEQ ID NO: 8)

(SEQ ID NO: 7)

(SEQ ID NO: 17)

(SEQ ID NO: 9)

Human Taspase1 Protein

MTMEKGMSSGEGLPSRSSQVSAGKITAKELETKQSYKEKRGGFVLVHAGAGYHSESKAKEYKHVCKRACQKAIEKLQAGA
LATDAVTAALVELEDSPFTNAGMGSNLNLLGEIECDASIMDGKSLNFGAVGALSGIKNPVSVANRLLCEGQKGKLSAGRI
PPCFLVGEGAYRWAVDHGIPSCPPNIMTTRFSLAAFKRNKRKLELAERVDTDFMQLKKRQSSEKENDSGTLDTVGAVVV
DHEGNVAAAVSSGGLALKHPGRVGQAALYGCGCWAENTGAHNPYSTAVSTSGCGEHLVRTILARECSHALQAEDAHQALL
ETMQNKFISSPFLASEDGVLGGVIVLRSCRCSAEPDSSQNKQTLLVEFLWSHTTESMCVGYMSAQDGKAKTHISRLPPGA
VAGQSVAIEGGVCRLESPVN

FIG. 12

Human Taspase1 cDNA

ATGACCATGGAGAAGGGATGAGTTCTGGAGAAGGGCTGCCTTCCAGATCATCTCAGGTTTCGGCTGTGTAAAATAACAGC
CAAAGAGTTGGAAACAAGCCAGTCCTATAAACATGTATCCAAACGAGCTTGTCAGAAGGAGCTTTGTCATGCAGGTTATCATT
CTGAATCCAAAGCCAAGCAGTATAAACATGTATCCAAACGAGCTTGTCAGAAGGAGCTTGTGTTGGTCATGCAGGTTATCATT
CTTGCAACTGACGCAGTCACTGCAGCACTGGTGCAAACGAGCTTGAGGATTCTCCTTTACAAATGCAGGAATGGAATCTAATCT
AAATCTGTTAGGTGAAATTGAGTGTGATGCCAACAGAGCCTACAGATGGGCAGTAGAGAACAAGAGAAACTAGAGCTGGAGCACTGA
GTGGAATCAAGAACCCAGTCTGGTTGCCAACAGAGCCTACAGATGGGCAGTAGAGAACAAGAGAAACTAGAGCTGGAGCACTGA
CCTCCCTGCTTTTTAGTGTGGAAGAAGCAGTAGCTGCATTAAAAGAACAAGTGAGGAAGAAAATGACTCAGGAGCACTTTGA
GACCACAAGAATTCAGTTAGCTGCATTAAAAGAACAAGTGAGGAAGAAAATGACTCAGGAGCACTTTGAAACATCCGGGGAG
TGCAACTAAAGAAAGAAGACAATCAAGTGAGGAAGAAAATGACTCAGGAGCACTTTGAAACATCCGGGGAGAGTTGGGCAGGCTGC
GACCAGAAGGGAATGTTGCTGCTGGGCTAGCACCATACTGGTGGCTAGAGAATGTTCACATGCTTAGAGATGTCCAAGCCCTGTTG
TCTTTATGGATGTGGCTGCCACCATACTGGCTAGAGAATGTTCACATGCTTAGAGATGTCCAAGCCCTGTTG
GAGAGCATCTTGTGCGAACAACAAGTTTATCAGTTCACCTTTCCTTGCCAGTGAAGATGGCGTGCGTCAGTGAATTTCGTGGAGCCACAGA
GAGAGCATCTTGTGCGAACAACAAGTTTATCAGTTCACCTTTCCTTGCCAGTGAAGATGGCGTGCTGGCCAGTGAATTTCGTGGAGCCACAGA
TTCATGCAGATGTTCTGCCGAGCCTGACTCCTGCCGATATGTCAGCCCAGGATGGGAAAAGCCAAGAACACATTTCAAGACTTCCTCCTGGTCCG
CGGAGAGCATGTGTGTCGGATATGTCAGCCCAGGATGGGAAAAGCCAAGAACACATTTCAAGACTTCCTCCTGGTGCG
GTGGCAGGACAGTCTGTGCAATCGTGGCAATCTGTGGGGTGGGGTGTGCCGCCCTGAAGGAGAGCCCAGTGAACTGA

FIG. 13

MLL accession number: L04284

Total of 3969 aa

MAHSCRWRFPARPGTTGGGGGGRRGLGGXPRQRVPALLLPPGPPVGGGGPGAPPSPPAVAAAAAAGSSGAGVPGGAAA
ASAASSSSASSSSSSSASSGPALLRVGPGFDAALQVSAAIGTNLRRFRAVFGESGGGGSGEDEQFLGFGSDEEVRVR
SPTRSPSVKTSPRKPRGRPRSGSDRNSAILSDPSVFSPLNKSETKSGDKIKKKDSKSIEKKRGRPPTFPGVKIKITHGKD
ISELPKGNKEDSLKKIKRTPSATFQQATKIKKLRAGKLSPLKSKFKTGKLQIGRKGVQIVRRGRPPSTERIKTPSVSSL
ILNWKSPRKSGKTRKEHLHLQKKIRQLSDKALEGLSQLGLFLLQKGQMQPLLSNSYRGQKKGAQKKIEKEAAQLQGRKVK
TQVKNIRQFIMPVVSAISSRIIKTPRRFIEDEDYDPPIKIARLESTPNSRFSAPSCGSSEKSSAASQHSSQMSSDSSRSS
SPSVDTSTDSQASEEIQVLPEERSDTPEVHPPLPISQSPENESNDRRSRRYSVSERSFGSRTTKKLSTLQSAPQQQTSSS
PPPPLLTPPPLQPASSISDHTPWLMPPTIPLASPFLPASTAPMQGKRKSILREPTFRWTSLKHSRSEPQYFSSAKYAKE
GLIRKPIFDNFRPPLLTPEDVGFASGFSASGTAASARLFSPLHSGTRFDMHKRSPLLRAPRFTPSEAHSRIFESVTLPSN
RTSAGTSSSGVSNRKRKRKVFSPIRSEPRSPSHSMRTRSGRLSSSELSPLTPPSSVSSSLSISVSPLATSALNPTFTFPS
HSLTQSGESAEKNQRPRKQTSAPAEPFSSSSPTPLFPWETPGSQTERGRNKDKAPEELSKDRDADKSVEKDKSRERDRER
EKENKRESRKEKRKKGSEIQSSSALYPVGRVSKEKVVGEDVATSSSAKKATGRKKSSSHDSGTDITSVTLGDTTAVKTKI
LIKKGRGNLEKTNLDLGPTAPSLEKEKTLCLSTPSSSTVKHSTSSIGSMLAQADKLPMTDKRVASLLKKAKAQLCKIEKS
KSLKQTDQPKAQGQESDSSETSVRGPRIKHVCRRAAVALGRKRAVFPDDMPTLSALPWEEREKILSSMGNDDKSSIAGSE
DAEPLAPPIKPIKPVTRNKAPQEPPVKKGRRSRRCGQCPGCQVPEDCGVCTNCLDKPKFGGRNIKKQCCKMRKCQNLQWM
PSKAYLQKQAKAVKKEKKSKTSEKKDSKESSVVKNVVDSSQKPTPSAREDPAPKKSSSEPPPRKPVEEKSEEGNVSAPG
PESKQATTPASRKSSKQVSQPALVIPPQPTTGPPRKEVPKTTPSEPKKQPPPESGPEQSKQKKVAPRPSIPVKQKPK
EKEKPPPVNKQENAGTLNILSTLSNGNSSKQKIPADGVHRIRVDFEKEDCEAENVWEMGGLGILTSVPITPRVVCFLCASS
GHVEFVYCQVCCEPFHKFCLEENERPLEDQLENWCCRRCKFCHVCGRQHQATKQLLECNKCRNSYHPECLGPNYPTKPTK
KKKVWICTKCVRCKSCGSTTPGKGWDAQWSHDFSLCHDCAKLFAKGNFCPLCDKCYDDDYESKMMQCGKCDRWVHSKCE
NLSDEMYEILSNLPESVAYTCVNCTERHPAEWRLALEKELQISLKQVLTALLNSRTTSHLLRYRQAAKPPDLNPETEESI
PSRSSPEGPDPPVLTEVSKQDDQQPLDLEGVKRKMDQGNYTSVLEFSDDIVKIIQAAINSDGGQPEIKKANSMVKSFFIR
QMERVFPWFSVKKSRFWEPNKVSSNSGMLPNAVLPPSLDHNYAQWQEREENSHTEQPLMKKIIPAPKPKGPGEPDSPTP
LHPPTPPILSTDRSREDSPELNPPPGIEDNRQCALCLTYGDDSANDAGRLLYIGQNEWTHVNCALWSAEVFEDDGSLKN
VHMAVIRGKQLRCEFCQKPGATVGCCLTSCTSNYHFMCSRAKNCVFLDDKKVYCQRHRDLIKGEVVPENGFEVFRRVFVD

FIG. 14A

FEGISLRRKFLNGLEPENIHMMIGSMTIDCLGIINDLSDCEDKLFPIGYQCSRVYWSTTDARKRCVYTCKIVECRPPVVE
PDINSTVEHDENRTIAHSPTSFTESSSKESQNTAEIISPPSPDRPPHSQTSGSCYYHVISKVPRIRTPSYSPTQRSPGCR
PLPSAGSPTPTTHEIVTVGDPLLSSGLRSIGSRRHSTSSLSPQRSKLRIMSPMRTGNTYSRNNVSSVSTTGTATDLESSA
KVVDHVLGPLNSSTSLGQNTSTSSNLQRTVTVGNKNSHLDGSSSEMKQSSASDLVSKSSSLKGEKTKVLSSKSSEGSA
HNVAYPGIPKLAPQVHNTTSRELNVSKIGSFAEPSSVSFSSKEALSFPHLHLRGQRNDRDQHTDSTQSANSSPDEDTEVK
TLKLSGMSNRSSINEHMGSSRDRRQKGKKSCKETFKEKHSSKSFLEPGQVTTGEEGNLKPEFMDEVLTPEYMGQRPCN
NVSSDKIGDKGLSMPGVPKAPPMQVEGSAKELQAPRKRTVKVTLTPLKMENESQSKNALKESSPASPLQIESTSPTEPIS
ASENPGDGPVAQPSPNNTSCQDSQSNNYQNLPVQDRNLMLPDGPKPQEDGSFKRYPRRSARARSNMFFGLTPLYGVRSY
GEEDIPFYSSTGKKRGKRSAEGQVDGADDLSTSDEDDLYYNFTRTVISSGGEERLASHNLFREEEQCDLPKISQLDGV
DDGTESDTSVTATTRKSSQIPKRNGKENGTENLKIDRPEDAGEKEHVTKSSVGHKNEPKMDNCHSVSRVKTQGQDSLEAQ
LSSLESSRRVHTSTPSDKNLLDTYNTELLKSDSDNNNSDDCGNILPSDIMDFVLKNTPSMQALGESPESSSELLNLGEG
LGLDSNREKDMGLFEVFSQQLPTTEPVDSSVSSSISAEEQFELPLELPSDLSVLTTRSPTVPSQNPSRLAVISDSGEKRV
TITEKSVASSESDPALLSPGVDPTPEGHMTPDHFIQGHMDADHISSPPCGSVEQGHGNNQDLTRNSSTPGLQVPVSPTVP
IQNQKYVPNSTDSPGPSQISNAAVQTTPPHLKPATEKLIVVNQNMQPLYVLQTLPNGVTQKIQLTSSVSSTPSVMETNTS
VLGPMGGGLTLTTGLNPSLPTSQSLFPSASKGLLPMSHHQHLHSFPAATQSSFPPNISNPPSGLLIGVQPPPDQLLVSE
SSQRTDLSTTVATPSSGLKKRPISRLQTRKNKKLAPSSTPSNIAPSDVVSNMTLINFTPSQLPNHPSLLDLGSLNTSSHR
TVPNIIKRSKSSIMYFEPAPLLPQSVGGTAATAAGTSTISQDTSHLTSGSVSGLASSSVLNVVSMQTTTTPTSSASVPG
HVTLTNPRLLGTPDIGSINLLIKASQQSLGIQDQPVALPPSSGMFPQLGTSQTPSTAAITAASSICVLPSTQTTGITAA
SPSGEADEHYQLQHVNQLLASKTGIHSSQRDLDSASGPQVSNFTQTVDAPNSMGLEQNKALSSAVQASPTSPGGSPSSPS
SGQRSASPSVPGPTKPKPKTKRFQLPLDKGNGKKHKVSHLRTSSSEAHIPDQETTSLTSGTGTPGAEAEQQDTASVEQSS
QKECGQPAGQVAVLPEVQVTQNPANEQESAEPKTVEEEESNFSSPLMLWLQQEQKRKESITEKKPKGLIVFEISSDDGFQ
ICAESIEDAWKSLTDKVQEARSNARLKQLSFAGVNGLRMLGILHDAVVFLIEQLSGAKHCRNYKFREHKPEEANEPPLNP
HGSARAEVHLRKSAFDMFNFLASKHRQPPEYNPNDEEEEVQLKSARRATSMDLPMPMRFRHLKKTSKEAVGVYRSPIHG
RGLFCKRNIDAGEMVIEYAGNVIRSIQTDKREKYYDSKGIGCYMFRIDDSEVVDATMHGNRARFINHSCEPNCYSRVINI
DGQKHIVIFAMRKIYRGEELTYDYKFPIEDASNKLPCNCGAKKCRKFLN

FIG. 14B

INHIBITORS OF TASPASE1 PROTEASE ACTIVITY

CLAIM OF PRIORITY

This application is a divisional and claims priority under 35 USC §120 to U.S. patent application Ser. No. 10/974,127, filed on Oct. 26, 2004, now abandoned which claims priority under 35 USC §119(e) to U.S. Patent Application Ser. No. 60/515,187, filed on Oct. 27, 2003, the entire contents of which is hereby incorporated by reference.

TECHNICAL FIELD

This invention relates to a novel protease.

BACKGROUND

MLL/HRX/ALL1 encodes a 3,969 amino acid nuclear protein bearing multiple conserved domains with assigned activities including: an N terminus with three AT-hook motifs that bind AT rich DNA segments (Zeleznik-Le et al., (1994) Proc. Natl. Acad. Sci. USA, 91:10610-10614), a DNA methyl transferase homology domain that represses transcription (Xia et al., (2003) Proc. Natl. Acad. Sci. USA), four PHD fingers that mediate protein-protein interactions (Fair et al., (2001) Mol. Cell. Biol., 21:3589-3597), a transactivation domain that interacts with CBP (Ernst et al., (2001) Mol. Cell. Biol., 21:2249-2258), and a C-terminal SET domain with histone H3 lysine 4 methyl transferase activity (Milne et al., (2002) Mol. Cell., Vol. 10:1107-1117; Nakamura et al., (2002) Mol. Cell., 10:1119-1128) (FIG. 1A). MLL and its *Drosophila* homologue trithorax are required for maintaining proper Hox and homeotic gene expression patterns, respectively (Breen and Harte, (1993) Development, 117:119-134; Yu et al., (1998) Proc. Natl. Acad. Sci. USA, 95:10632-10636).

Chromosome translocations characteristically found in human infant leukemia disrupt MLL (11q23), generating chimeric proteins between the MLL N-terminus and multiple translocation partners that vary substantially (Ayton and Cleary, Oncogene, (2001) 20:5695-5707; Domer et al., (1993) Proc. Natl. Acad. Sci. USA, 90:7884-7888; Downing and Look, (1996) Cancer Treat. Res., 84:79-92; Gu et al., (1992) Cell, 71:701-708; Thirman et al., (1993) New England Journal of Medicine, 329:909-914; Tkachuk et al., (1992) Cell, 71:691-700). Mice carrying engineered Mll translocations develop leukemia (Corral et al., (1996) Cell, 85:853-851; Forster et al., (2003) New England Journal of Medicine, 326:800-806). Gene expression profiles of infant leukemias bearing MLL translocations identified a characteristic gene expression profile that distinguishes this poor prognosis leukemia from other leukemias (Armstrong et al., (2002) Nat. Genet., 30:41-47; Yeoh et al., (2002) Cancer Cell, 1: 133-143). Among the upregulated genes were some recognized targets of MLL including select HOX genes. Deregulated expression of HOX genes typifies certain malignancies (Buske and Humphries, (2002) Int. J. of Hematol., 71:391-398; Cillo et al., (2001) Int. J. Hematol., 71:161-169; Dash and Gilliland, (2001) Best Pract. Res. Clin. Haematol., 14:49-64).

Recently, we and others demonstrated that MLL is normally processed at two cleavage sites, CS1 (D/GADD) and CS2 (D/GVDD), and that mutation of both sites abolishes the proteolysis (Hsieh et al., (2003) Mol. Cell. Biol., 23:186-194; Yokoyama et al., (2002) Blood, 100:3710-3718) (FIG. 1B). The sequence of the cleavage site is highly conserved in MLL homologues from flies to mammals. MLL cleavage generates N-terminal p320 (N320) and C-terminal p180 (C180) fragments, which heterodimerize to form a stable complex that localizes to a subnuclear compartment. Within this complex, the FYRN domain of N320 directly interacts with the FYRC and SET domains of C180. This dynamic post-cleavage association confers stability to N320 and correct nuclear sublocalization of the MLL complex for proper target gene expression (Hsieh et al., (2003) Mol. Cell. Biol., 23:186-194).

Site-specific proteolysis is essential in many important biological pathways including the sequential activation of blood coagulation factors (Furie and Furie, (1992) New England Journal of Medicine, 326:800-806), cholesterol-gauged liberation of SREBP from the ER (Brown et al., (2000) Cell, 100:391-398), ligand-activated cleavage and subsequent release of the intracellular domain of Notch (Brown et al., (2000) Cell, 100:391-398), maturation of the hedgehog signaling molecule (Ye and Fortini, Semin. (2000) Cell Dev. Biol., 11:211-221), separation of HCF-1 for proper cell cycle regulation (Wilson et al., (1995) Genes. Dev., 9:2445-2458), and activation of caspases and their subsequent cleavage of death substrates during apoptosis (Thornberry and Lazebnik, (1998) Science, 281:1312-1316). Identification and characterization of the responsible proteases has not only proven critical to understanding such biologic processes but also for developing targeted therapeutics for diseases involving specific pathways.

SUMMARY

The present invention is based, in part, on the discovery of a novel protease, referred to herein as "Taspase1". The amino acid sequence of a human Taspase1 polypeptide is shown in SEQ ID NO:1 (See e.g., FIG. 12), and the nucleotide sequence of a cDNA encoding human Taspase1 is shown in SEQ ID NO:2 (See e.g., FIG. 13).

Accordingly, in one aspect, the invention features, Taspase1 polypeptides, and biologically active or antigenic fragments thereof that are useful, e.g., as reagents or targets in assays applicable to treatment and diagnosis of Taspase1-mediated or Taspase1-related disorders or as antigens for eliciting antibodies directed against Taspase1. In another embodiment, the invention provides Taspase1 polypeptides having a Taspase1 activity. Preferred polypeptides are Taspase1 proteins including at least one Taspase1 domain, e.g., an Asparaginase_2 homology domain, and, preferably, having MLL CS1 and/or CS2 cleavage activity.

In other embodiments, the invention provides Taspase1 polypeptides, e.g., a Taspase1 polypeptide having the amino acid sequence shown in SEQ ID NO: 1; an amino acid sequence that is substantially identical to the amino acid sequence shown in SEQ ID NO: 1; or an amino acid sequence encoded by a nucleic acid molecule having a nucleotide sequence which hybridizes under a stringency condition described herein to a nucleic acid molecule comprising the nucleotide sequence of SEQ ID NO:2, wherein the nucleic acid encodes a full length Taspase1 protein or an active fragment thereof.

In a related aspect, the invention provides Taspase1 polypeptides or fragments operatively linked to non-Taspase1 polypeptides to form fusion proteins.

In another aspect, the invention features antibodies and antigen-binding fragments thereof, that react with, or more preferably specifically bind Taspase1 polypeptides or fragments thereof.

In another aspect, the invention provides methods of screening for compounds that modulate (e.g., inhibit) the expression or activity of a Taspase1 polypeptide or nucleic acid.

In still another aspect, the invention provides a process for modulating (e.g., inhibiting) Taspase1 polypeptide or nucleic acid expression or activity, e.g. using a peptide, derived peptide, or small molecule that inhibits the ability of Taspase1 to cleave a Taspase1 substrate, e.g., MLL (which is shown in SEQ ID NO: 59 (See e.g., FIG. 14)). Thus a suitable inhibitor might have a $K_i$ for inhibition of MLL cleavage of about $10^{-4}$ M, $10^{-5}$ M, $10^{-6}$ M, $10^{-7}$ M, $10^{-8}$ M, $10^{-9}$ M or less. In certain embodiments, the methods involve treatment of conditions related to aberrant activity or expression of the Taspase1 polypeptides or nucleic acids, such as conditions involving aberrant or deficient HOX gene expression and cellular proliferation or differentiation. Thus, such inhibitors can be used to reduce undesirable Taspase1 proteolytic activity. The inhibitors can also inhibit other proteases having the same mechanism as Taspase1. In some instances it is desirable to inhibit normal Taspase1 expression or activity, wherein the inhibition of such Taspase1 activity will reduce the expression or activity of other gene products such as MLL or HOX gene products, which are expressed, for example, in malignant cells.

In yet another aspect, the invention provides methods for reducing Taspase1 expression. The method includes contacting the cell with a compound or agent (e.g., a compound identified using the methods described herein) that modulates (e.g., inhibits) the expression, of the Taspase1 polypeptide or nucleic acid. In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol.

In a preferred embodiment, the compound is an inhibitor of a Taspase1 polypeptide. Preferably, the inhibitor is chosen from a peptide (e.g., a polypeptide including naturally occurring as well as non-naturally occurring amino acids), a peptidomimetic, a phosphopeptide, a small organic molecule, a small inorganic molecule and an antibody. In another preferred embodiment, the compound is an inhibitor of a Taspase1 nucleic acid, e.g., an antisense, a ribozyme, or an RNAi or a triple helix molecule.

The compound can be administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

In another aspect, the invention features methods for treating or preventing a disorder characterized by aberrant cellular proliferation or differentiation of a Taspase1-expressing cell in a subject. Preferably, the method includes administering to the subject (e.g., a mammal, e.g., a human) an effective amount of a compound (e.g., a compound identified using the methods described herein) that modulates the activity, or expression, of the Taspase1 polypeptide or nucleic acid (e.g., inhibits proteolytic cleavage of MLL). In a preferred embodiment, the disorder is a cancerous or pre-cancerous condition (e.g., leukemia).

In another aspect, the invention provides methods for evaluating the efficacy of a therapeutic or prophylactic agent (e.g., an anti-neoplastic agent). The method includes: contacting a sample with an agent (e.g., a polypeptide inhibitor or a compound identified using the methods described herein) and, evaluating the expression or function of Taspase1 nucleic acid or polypeptide in the sample before and after the contacting step. A change, e.g., a decrease or increase, in the level of Taspase1 nucleic acid (e.g., mRNA) or polypeptide function (e.g., proteolysis of MLL) in the sample obtained after the contacting step, relative to the level of expression in the sample before the contacting step, is indicative of the efficacy of the agent. The level of Taspase1 nucleic acid or polypeptide expression or function can be detected by any method described herein (e.g., measuring the cleavage of MLL using a labeled MLL substrate and SDS-PAGE).

The invention also features a nucleic acid molecule that encodes a Taspase1 protein or polypeptide, e.g., a biologically active portion of the Taspase1 protein. In a preferred embodiment the isolated nucleic acid molecule encodes a polypeptide having the amino acid sequence of SEQ ID NO:1. In other embodiments, the invention provides isolated Taspase1 nucleic acid molecules having the nucleotide sequence shown in SEQ ID NO:2. In other embodiments, the invention provides a nucleic acid molecule which hybridizes under a stringency condition described herein to a nucleic acid molecule comprising the nucleotide sequence of SEQ ID NO:2, wherein the nucleic acid encodes a full length Taspase1 protein or an active fragment thereof.

In a related aspect, the invention further provides nucleic acid constructs that include a Taspase1 nucleic acid molecule described herein. In certain embodiments, the nucleic acid molecules of the invention are operatively linked to native or heterologous regulatory sequences. Also included are vectors and host cells containing the Taspase1 nucleic acid molecules of the invention e.g., vectors and host cells suitable for producing Taspase1 nucleic acid molecules and polypeptides.

In still another related aspect, isolated nucleic acid molecules that are antisense to or interfere with (e.g., an RNAi) a Taspase1 encoding nucleic acid molecule are provided.

In one aspect, the invention features an isolated polypeptide having an amino acid sequence, which is at least about 80% identical to the amino acid sequence of SEQ ID NO:1.

The peptide can have one or more of the following features. The polypeptide can include a heterologous polypeptide. The polypeptide can cleave a polypeptide comprising an Asp-Gly-Ala-Asp-Asp (SEQ ID NO:3) or Asp-Gly-Val-Asp-Asp (SEQ ID NO:4) sequence between the Asp and the Gly amino acids of the Asp-Gly-Ala-Asp-Asp (SEQ ID NO:3) or Asp-Gly-Val-Asp-Asp (SEQ ID NO:4) sequence. The polypeptide can be intramolecularly proteolyzed into a first peptide fragment and a second peptide fragment. One of the first or second peptide fragments can include a threonine at the N-terminus. The polypeptide can have a conserved Leu-Asp-Thr-Val-Gly (SEQ ID NO:5) motif. Amino acids 232-236 of the peptide can be Leu-Asp-Thr-Val-Gly (SEQ ID NO:5). The polypeptide can include the amino acid sequence of SEQ ID NO: 1, wherein up to 20 amino acids are substituted.

In another embodiment, the invention features an isolated polypeptide encoded by a nucleic acid that hybridizes under high stringency conditions to the nucleic acid of SEQ ID NO:2.

In one embodiment, the invention features a host cell including the any one of the polypeptides described herein.

In one embodiment, the invention features a method for producing a polypeptide described herein including culturing a host cell under conditions in which the nucleic acid encoding the polypeptide is expressed.

The invention also features an antibody that selectively binds to a polypeptide described herein.

In one embodiment, the invention features an inhibitor of a polypeptide described herein. The inhibitor can be a polypeptide. In some instances, the polypeptide includes one of the following amino acid sequences, Ser-Gln-Leu-Ala (SEQ ID NO:6), Ile-Ser-Gln-Leu-Ala (SEQ ID NO:7) or Lys-Ile-Ser-Gln-Leu-Ala (SEQ ID NO:8), Ser-Gln-Leu-Asp-aldehyde (SEQ ID NO:9), Ile-Ser-Gln-Leu-Asp-aldehyde (SEQ ID NO:10), or Lys-Ile-Ser-Gln-Leu-Asp-aldehyde (SEQ ID NO:11), Ser-Gln-Leu-Asp-chloromethylketone (SEQ ID NO:12), Ile-Ser-Gln-Leu-Asp-chloromethylketone (SEQ ID NO:13), or Lys-Ile-Ser-Gln-Leu-Asp-chloromethylketone (SEQ ID NO:14). The inhibitor can also include a peptidomimetic of one of amino acid sequences Ser-Gln-Leu-Ala (SEQ ID NO:6), Ile-Ser-Gln-Leu-Ala (SEQ ID NO:7) or Lys-Ile-Ser-Gln-Leu-Ala (SEQ ID NO:8), Ser-Gln-Leu-Asp-aldehyde (SEQ ID NO:9), Ile-Ser-Gln-Leu-Asp-aldehyde (SEQ ID NO:10), or Lys-Ile-Ser-Gln-Leu-Asp-aldehyde (SEQ ID NO:11), Ser-Gln-Leu-Asp-chloromethylketone (SEQ ID NO:12), Ile-Ser-Gln-Leu-Asp-chloromethylketone (SEQ ID NO:13), or Lys-Ile-Ser-Gln-Leu-Asp-chloromethylketone (SEQ ID NO:14).

In one embodiment, the invention features a method of treating a subject including administering to the subject an inhibitor of any of the polypeptides described herein. In some instances, the method includes administering an additional therapeutic agent.

In another embodiment, the invention features a method of treating cancer in a subject including administering to the subject an inhibitor of any of the polypeptides described herein. In some instances, the method includes administering an additional therapeutic agent (e.g., an anti-cancer agent). In some instances, the cancer is a hematopoietic neoplasm or a solid cancer. In other instances, the cancer is a leukemia.

In one embodiment, the invention features a method of identifying an inhibitor of a polypeptide described herein, the method including:
 (a) providing a polypeptide described herein;
 (b) contacting the polypeptide with a candidate inhibitor and a proteolytic substrate;
 (c) measuring proteolysis of the substrate in the presence of the candidate inhibitor, and
 (d) comparing the proteolysis of the substrate in the presence of the candidate inhibitor to the proteolysis of the substrate in the absence of the candidate inhibitor, wherein a decrease in proteolytic activity identifies the candidate inhibitor as an inhibitor.

The method can include one or more of the following features: The polypeptide can be provided in vivo or in vitro. The substrate can include a Taspase1 substrate. Alternatively, the substrate can include a CS1-like or CS2-like motif. The substrate can include a fragment of an MLL family protein including one or more of a CS1, CS2, Ile-Ser-Gln-Leu-Asp (SEQ ID NO:15), or Glu-Gly-Gln-Val-Asp (SEQ ID NO:16) motif. The method can be performed in an array format. The method can also include generating dataset correlating a value for the measured function with the determination of whether the agent is an inhibitor of the polypeptide.

In another aspect, the invention features a method of treating a subject including administering to the subject an inhibitor identified by a method described herein.

In yet another aspect, the invention features a method of treating cancer in a subject including administering to the subject an inhibitor identified by a method described herein. In some instances, the cancer can be a solid tumor or leukemia.

In still another aspect, the invention features a method of treating a heomatopoetic proliferative disorder in a subject including administering to the subject an inhibitor identified by a method described herein.

In still another aspect, the invention features an inhibitor identified by a method described herein.

The Taspase1 polypeptide, fragments thereof, and derivatives and other variants of the sequence in SEQ ID NO:1 thereof are collectively referred to as "polypeptides or proteins of the invention" or "Taspase1 polypeptides or proteins".

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C.

An "isolated" or "purified" polypeptide or protein is substantially free of cellular material or other contaminating proteins from the cell or tissue source from which the protein is derived, or substantially free from chemical precursors or other chemicals when chemically synthesized.

A "non-essential" amino acid residue is a residue that can be altered from the wild-type sequence of Taspase1 without abolishing or substantially altering a Taspase1 activity. An "essential" amino acid residue is a residue that, when altered from the wild-type sequence of Taspase1, results in abolishing or substantially abolishing a Taspase1 activity. For example, conserved amino acid residues in Taspase1 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a Taspase1 protein is preferably replaced with another amino acid residue from the same side chain family.

The term "peptidomimetic" refers to a chemical compound that mimics the ability of a peptide to recognize certain physiological molecules, such as proteins (e.g., Taspase1) and DNA.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1B depicts the conservation of CS1 (D/GADD) (SEQ ID NO:3) and CS2 (D/GVDD) (SEQ ID NO:4) among MLL family members.

FIG. 3C depicts alignment of active sites among Asparaginase_2 family proteins.

FIG. 3E depicts alignment of the amino acid sequences of putative Taspase1 proteins in various species.

FIG. 12 depicts the amino acid sequence of human Taspase1 (SEQ ID NO:1).

FIG. 13 depicts the cDNA sequence of human Taspase1 (SEQ ID NO:2).

FIG. 14 depicts the amino acid sequence of human MLL (SEQ ID NO:59).

DETAILED DESCRIPTION

The invention is based, in part, on the discovery of a novel protease, Taspase1. Taspase1 cleaves MLL at two conserved sites (D/GADD (referred to herein as CS1) and D/GVDD (referred to herein as CS2)) generating N-terminal 320 kDa and C-terminal 180 kDa fragments, which heterodimerize to both stabilize the complex and confer it subnuclear destination.

Taspase1 was purified and cloned using highly conserved cleavage motifs within MLL. Upon the purification and cloning of Taspase1, it was discovered that Taspase1 (threonine aspartase 1) is the first endopeptidase within a family of enzymes possessing an Asparaginase_2 homology domain. Other members present in both prokaryotes and eukaryotes include the amidohydrolases, L-Asparaginase in intermediary amino acid metabolism and Glycosylasparaginase. Glycosylasparaginase participates in the ordered degradation of N-linked glycoproteins by cleaving Asn-GlcNAc linkages that join oligosaccharides to proteins.

Site Specific MLL Cleavage Substrate

Figure 1A:
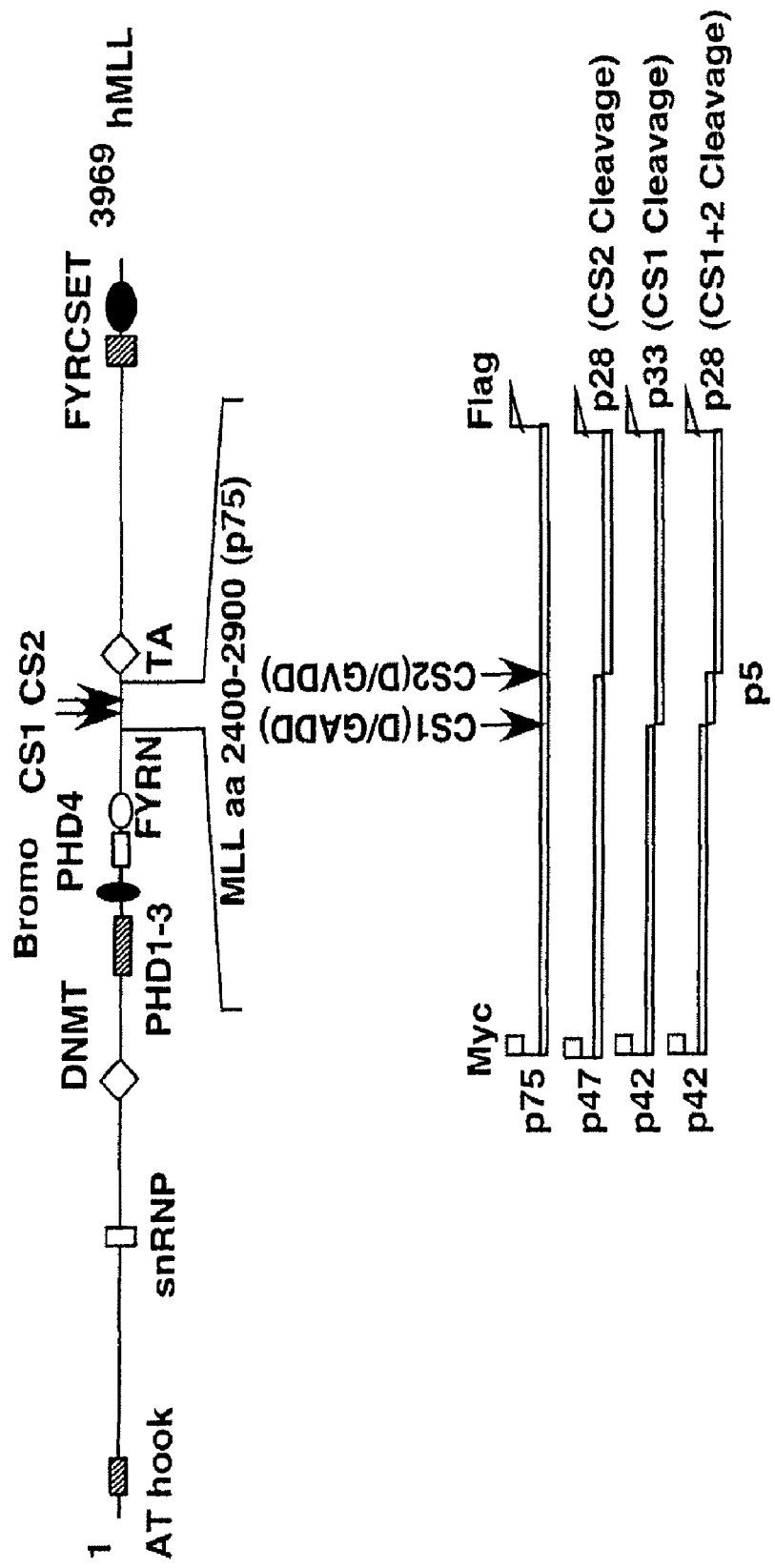
FIG. 1A depicts conserved domain structures of human MLL with cleavage sites (CS1 (D/GADD (SEQ ID NO:3)) and CS2 (D/GVDD (SEQ ID NO:4))) positioned thereon.
Figure 1C:
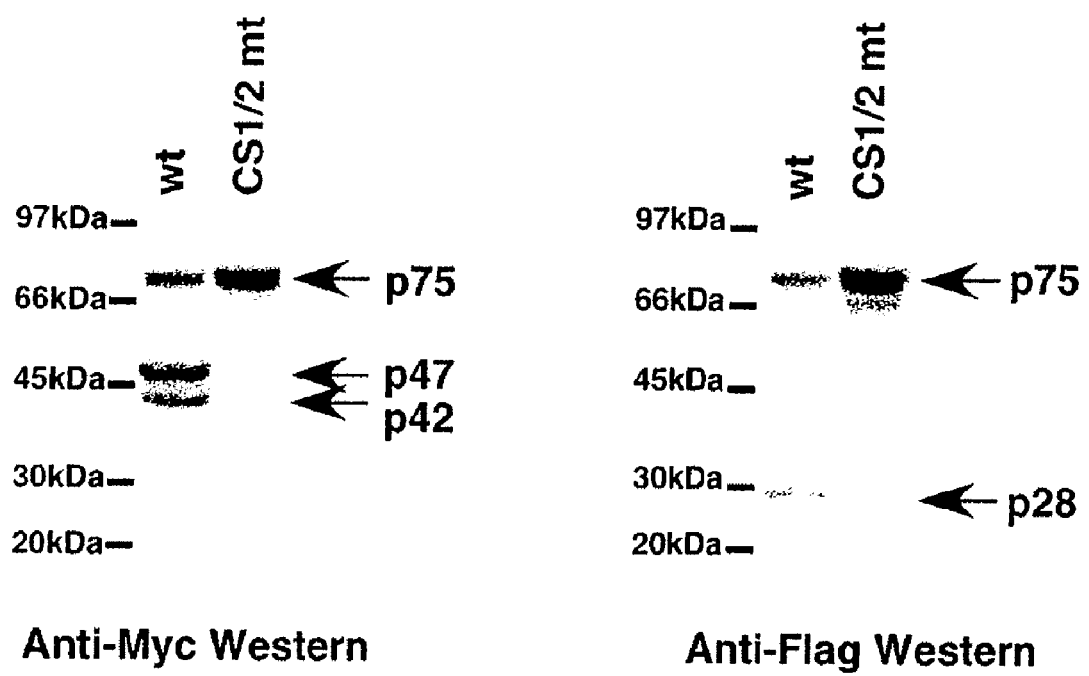
FIG. 1C depicts the results of a study showing that Taspase1 has a preference for the CS2 over the CS1 cleavage site.
Figure 2A:
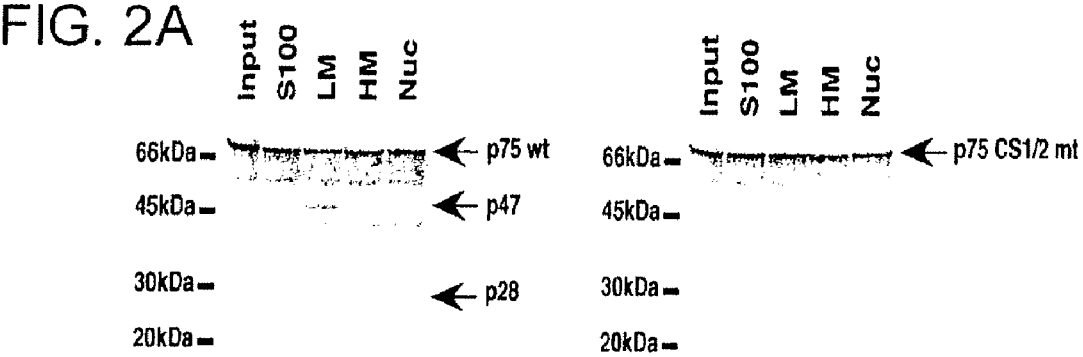
FIG. 2A depicts the results of a study demonstrating in vitro reconstitution of MLL cleavage using subcellular fractions.
Figure 2B:
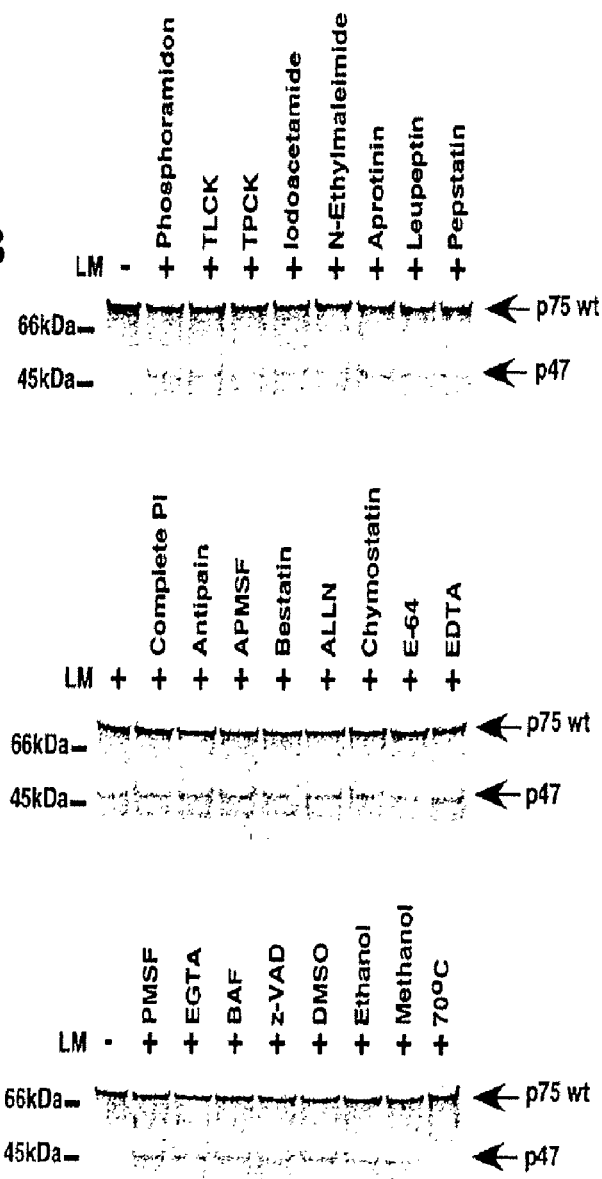
FIG. 2B depicts the results of a study showing that Taspase1 proteolysis of MLL is not affected by various protease inhibitors.

To facilitate the purification and characterization of the MLL protease, we generated a tractable cleavage substrate. We found that aa 2,400 to 2,900 of MLL containing CS1 (aa 2,666) and CS2 (aa 2,718) are sufficient to recapitulate endogenous MLL cleavage (FIG. 1C). Proteolysis of this p75 MLL test substrate at CS 1 or CS2 would generate N-terminal Myc-tagged p42 or p47 fragments and C-terminal Flag-tagged p33 or p28 respectively (FIG. 1A). The p47 and p28 fragments were most abundant, indicating processing at CS2 is more efficient than at CS1. This is consistent with our prior observations of the proteolysis of full-length MLL protein (Hsieh et al., Mol. Cell. Biol., Vol. 23, pp. 186-194; 2003)). The transfected p75 MLL substrate with mutant CS1/CS2 sites (CS1/2 mt) was not cleaved, indicating the specificity of this substrate (FIG. 1C). Subcellular fractions derived from 293T cells (a human embryonic kidney cell line) were incubated with in vitro transcribed/translated $^{35}$S-methionine labeled p75 MLL substrates. The light membrane (LM) fraction displayed the most enzymatic activity (FIG. 2A, left panel) and did not cleave the mutant fragment (CS1/2 mt) (FIG. 2A, right panel). Inhibitors of multiple classes of proteases including serine proteases, cysteine proteases, metalloproteases, acid proteases, and the 26S proteosome, were examined but again showed no substantial inhibition of MLL proteolysis in this fraction enriched for endoplasmic reticulum (FIG. 2B). Only heat incubation at 70° C. for 30 minutes inactivated the proteolytic activity in light membranes.

Purification

Figure 3A:
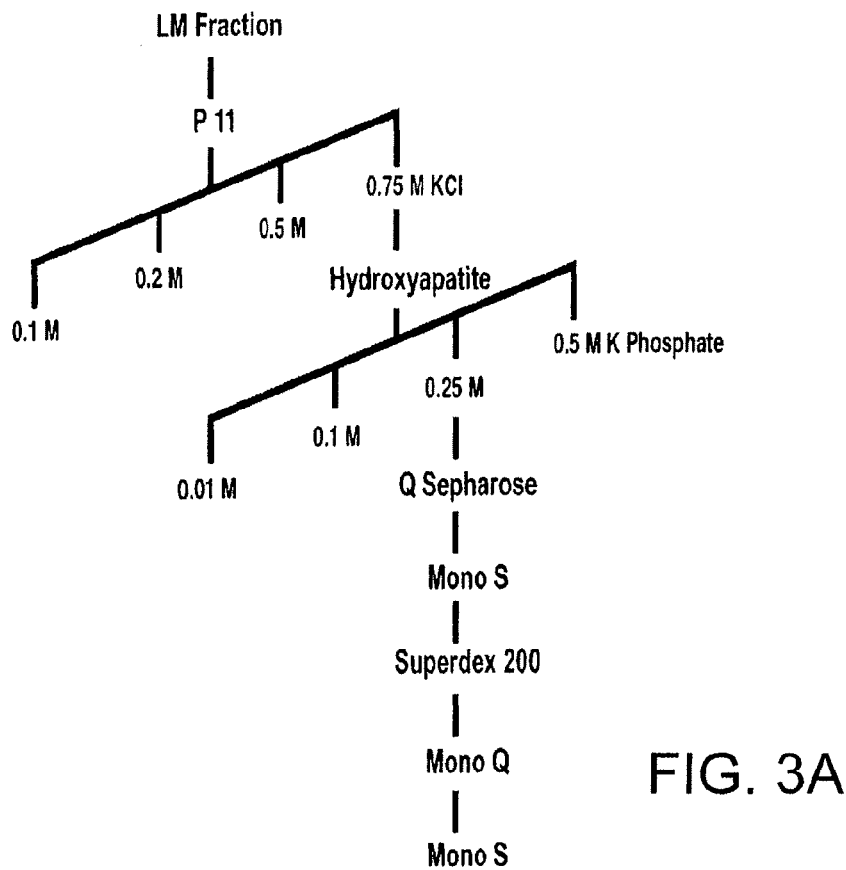
FIG. 3A schematically depicts the methods used for purification of the MLL cleaving protease, Taspase1.
Figure 3B:
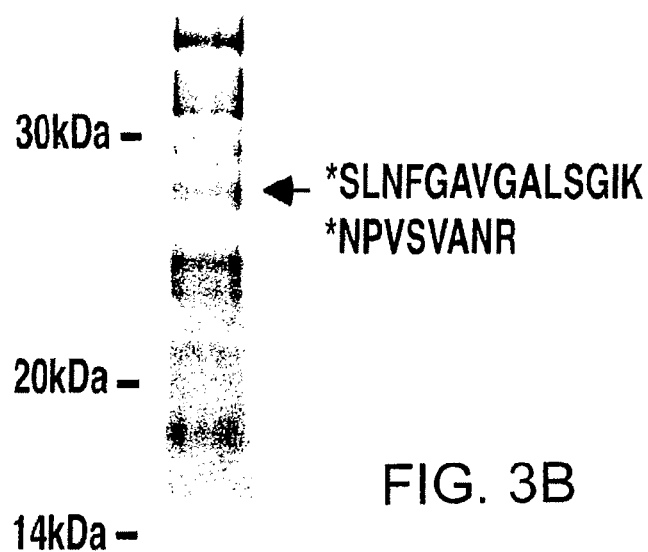
FIG. 3B depicts a silver stained SDS-PAGE of the mono S fraction with maximum enzymatic activity. The amino acid sequence SLNFGAVGALSGIK corresponds to amino acids 124-137 of SEQ ID NO:1. The amino acid sequence NPVSVANR corresponds to amino acids 138-145 of SEQ ID NO:1.

The LM fraction possessing the protease activity was subjected to serial column chromatography and the activity followed by an in vitro cleavage assay. Seven chromatographic steps achieved an approximately 200,000-fold enrichment of the proteolytic activity (FIG. 3A). The ultimate mono S fractions displaying the highest enzymatic activity were subjected to SDS-PAGE followed by a silver stain (FIG. 3B). Polypeptide bands whose presence best correlated with the proteolytic activity were digested with trypsin and subjected to liquid chromatography and tandem mass spectrometry (LC-MS/MS) sequence analysis. Two peptide sequences corresponding to aa 124 to 137 and aa 138 to 145 of an uncharacterized open reading frame (orf) present on chromosome 20 (c20orf13) were identified from a gel slice that migrated at ~28 kDa (FIG. 3B). The orf predicts a 420 aa protein possessing an Asparaginase_2 homology domain (pfam 01112, interpro 000246) from aa 41 to 391 (FIG. 3C). Typical proteins that contain this signature motif include L-Asparaginase and Glycosylasparaginase (FIG. 3C). Three distinct conserved motifs distinguish the Taspase1, Glycosylasparaginase and L-Asparaginase subfamilies. L-Asparaginase catalyzes an amide bond hydrolysis to convert L-asparagine to L-aspartate. Glycosylasparaginase is an amidohydrolase which catalyzes the N-acetylglucosamine-asparagine bond that links oligosaccharides to asparagine. However, no endopeptidase activity had been demonstrated to date among the Asparaginase_2 family enzymes. The characteristics of this MLL cleaving protease (c20orf13) as subsequently detailed here prompts its designation as Taspase1 (Threonine aspartase1). Sequence alignment searches of the public databases identified highly conserved Taspase1 orthologues in fly, mosquito, pufferfish, zebrafish, rat, mouse, and human (FIG. 3C and FIG. 3E), but not in the nematode, C. elegans. The conserved LDTVG motif that surrounds a putative threonine active site is distinct from L-Asparaginase and Glycosylasparaginase (FIG. 3C) suggesting it may have a unique specificity.

Recombinant Taspase1 Activity

Figure 4A:
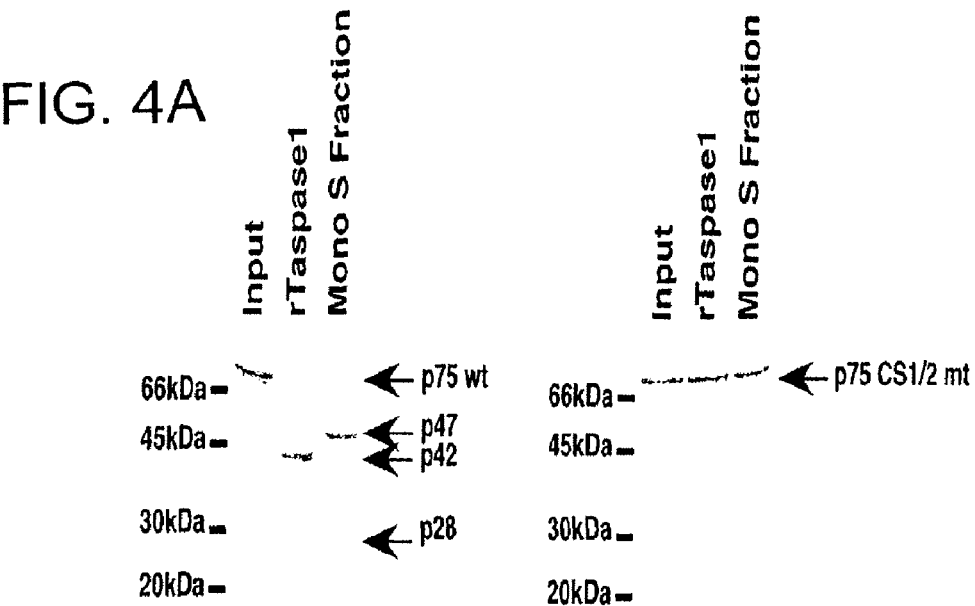
FIG. 4A depicts the results of a study comparing cleavage of MLL wild type substrate and mutant substrate by recombinant Taspase1 versus Mono S fraction.
Figure 4B:
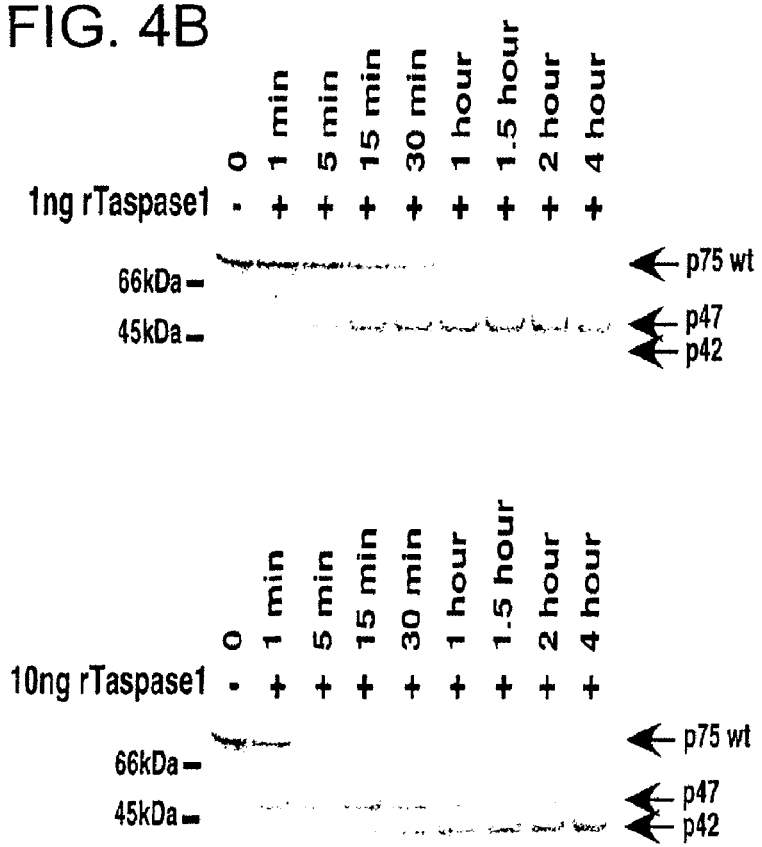
FIG. 4B depicts the results of a study demonstrating that Taspase1 sequentially cleaves CS1 and CS2.

To assess the potential activity of this candidate protease, we expressed and purified recombinant N-terminal Histagged Taspase1 from E. coli. Recombinant Taspase1 (rTaspase1) cleaved the wt p75 MLL but not the CS1/2 mt substrate (FIG. 4A). rTaspase1 more efficiently processed p75 MLL to completion based on the predominance of the p42 fragment when compared to the activity in the original mono S fraction (FIG. 4A). The p42 fragment results from cleavage at the CS1 (D/GADD) (SEQ ID NO:3) site, which is less conserved than CS2 (D/GVDD) (SEQ ID NO:4) and is also less efficiently processed in vivo (Hsieh et al., (2003) Mol. Cell. Biol., 23:186-194). We next examined the differential sensitivity of CS1 and CS2 sites for cleavage by rTaspase1. The p47 fragment appears first, while higher enzyme concentration or more time is needed for the appearance of the p42 fragment indicating a preference of rTaspase1 for CS2 over CS1 (FIG. 4B). Thus the proteolytic characteristics of rTaspase1 match the pattern of endogenous MLL proteolysis.

Characterization of Taspase1

Figure 3D:
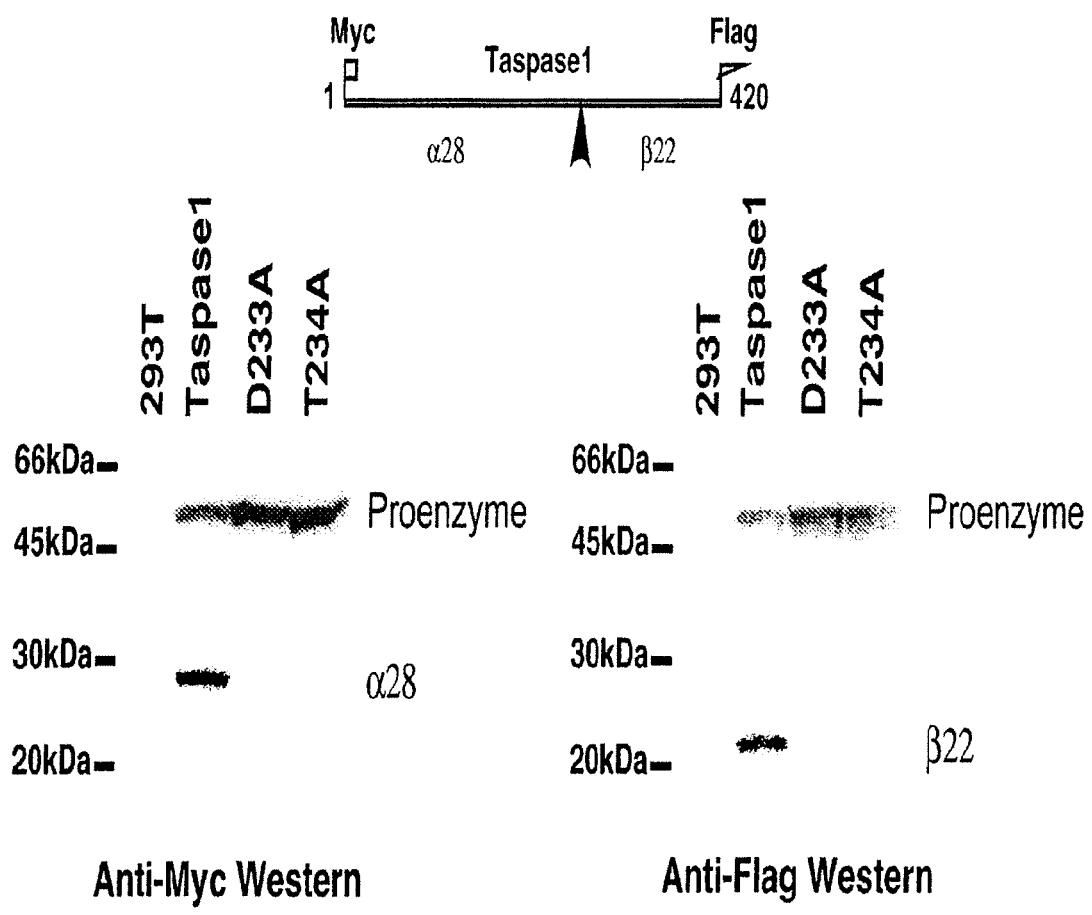
FIG. 3D depicts the results of a study demonstrating the self-proteolysis of Taspase1.
Figure 3E-1:
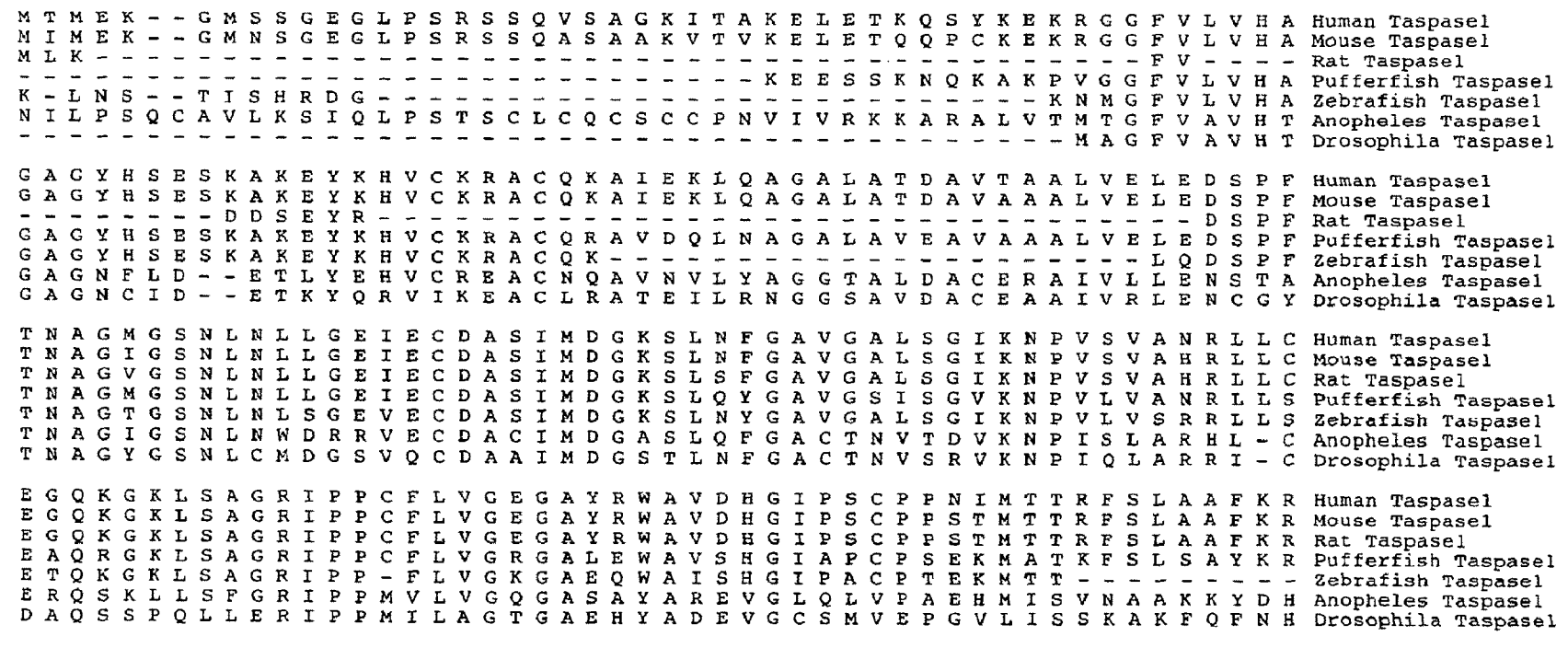
Figure 3E-2:
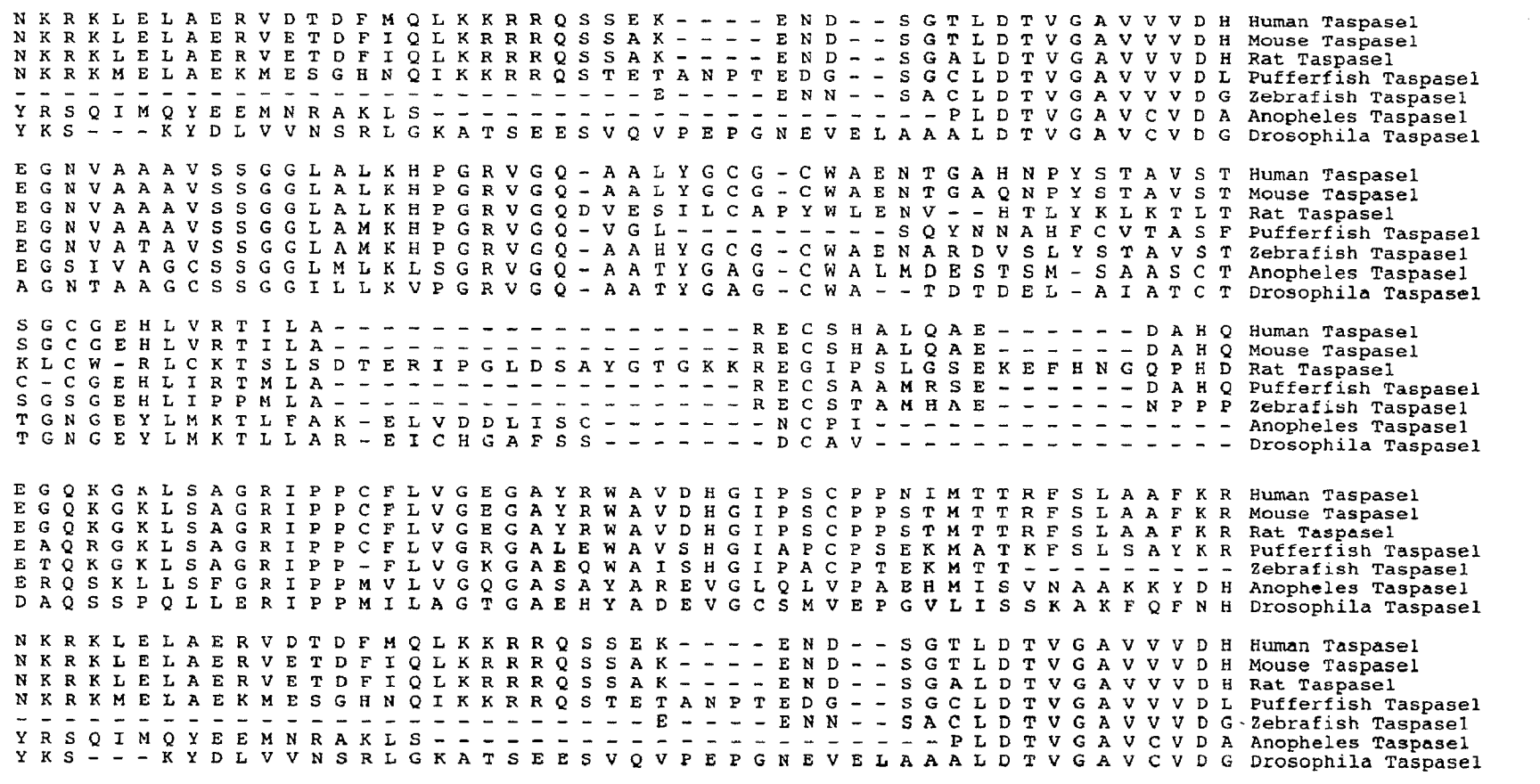
Figure 5A:
FIG. 5A depicts the results of coomassie blue staining of purified recombinant Taspase1, demonstrating that Taspase1 proenzyme undergoes intramolecular processing to an active 29 kDa α/22 kDa β heterodimer.
Figure 5B:
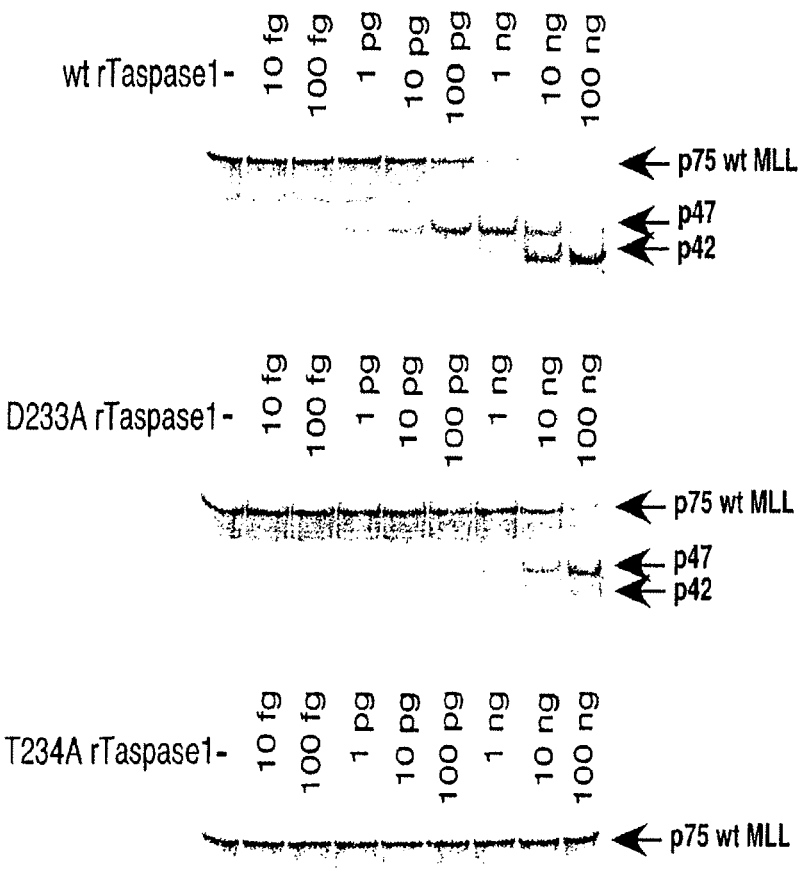
FIG. 5B, depicts the results of coomassie blue staining of purified recombinant Taspase1, demonstrating Threonine 234 of Taspase1 is essential for its enzymatic activity.

Purification of recombinant N-terminal His-tagged Taspase1 yielded an expected 50 kDa product, a His-tagged 28 kDa a subunit, and a co-purified 22 kDa polypeptide (FIG. 5A). This 22 kDa polypeptide was subjected to N-terminal Edman degradation analysis, which identified threonine 234 of Taspase1 as the N-terminal amino acid of the apparent 22 kDa β subunit (FIG. 5A). This represents proteolysis between aspartate 233 and threonine 234 of the 50 kDa putative proenzyme. Similarly when an N-terminal and C-terminal epitope tagged human Taspase1 cDNA was expressed in the human 293 T cell line, the 50 kDa product also appeared to be processed to a 28 kDa N-terminal α subunit and a 22 kDa C-terminal β subunit (FIG. 3D). This suggested that Taspase1 may be intramolecularly proteolyzed and processed subunits reassembled through a non-covalent association. Amino acid substitution of either aspartate 233 (D233A) or threonine 234 (T234A) to alanine abolished the intramolecular processing of Taspase1 expressed in E. coli (FIG. 5A) or in mammalian cells (FIG. 3D). However, the D233A mutant retained some residual enzymatic activity, although it was ~1000 fold less efficient than the wt enzyme (FIG. 5B, middle panel). Conversely, threonine 234 which became the N-terminus of the β subunit is absolutely essential for cleavage activity (FIG. 5B, lower panel). These enzymatic characteristics are similar to properties shared by L-Asparaginase and Glycosylasparaginase which also demonstrate autoproteolysis of a proenzyme into an active α/β heterodimeric enzyme in which the N-terminal threonine of the β subunit is the active site nucleophile for catalysis (Guan et al., (1996) J. Biol. Chem., 27:1732-1737; Liu et al., (1998) J. Biol. Chem., 273:9688-9694; Tikkanen et al., (1996) Embo. J., 15:2954-2960; Xu et al., (1999) Cell, 98:651-661). Thus, this MLL cleaving protease is the first endopeptidase within the Asparaginase_2 family with the novel characteristic of being a threonine aspartase, Taspase1.

Proteolysis of MLL In Vivo Requires Taspase1

Figures 6A, 6B:
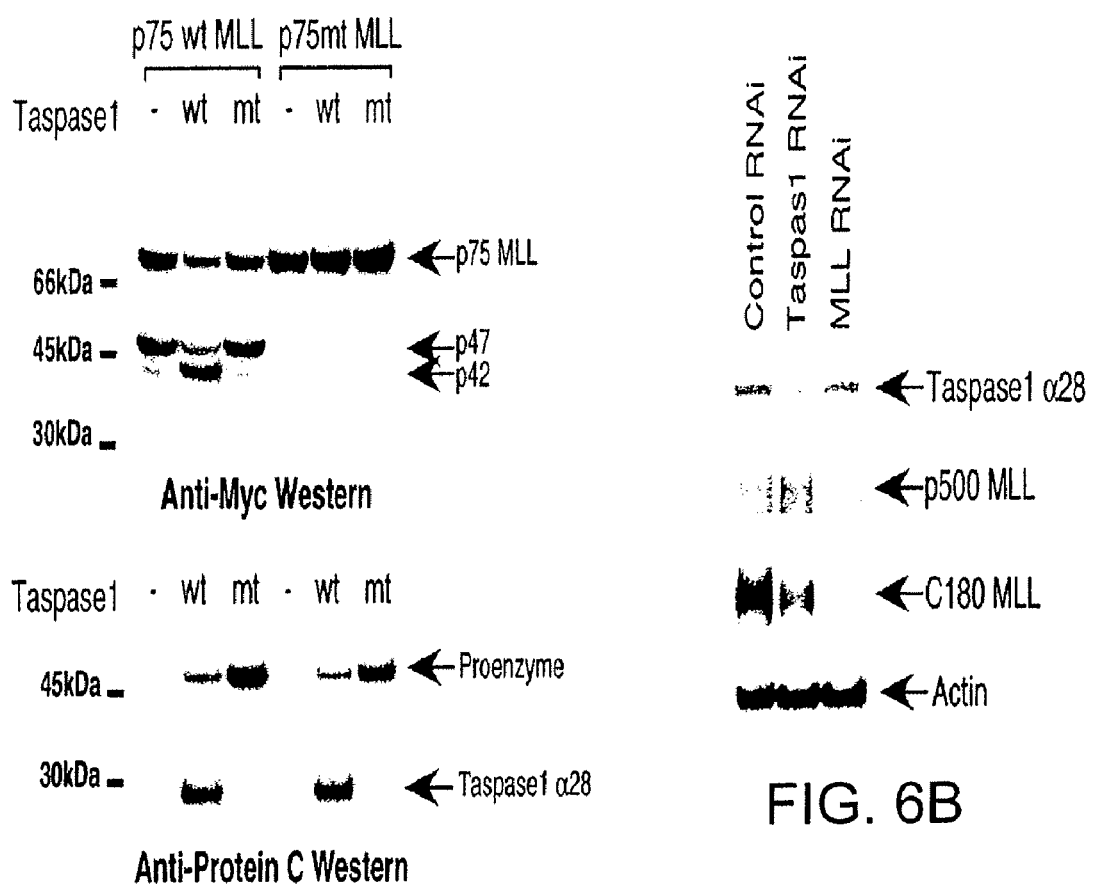
FIG. 6A depicts the results of an assay demonstrating that Taspase1 cleaves the MLL reporter but not the CS1/2 mutant and that wild type Taspase1 but not the T234A Taspase1 mutant underwent intramolecular processing.
FIG. 6B depicts the results of a study demonstrating that RNAi against Taspase1 resulted in the decrease of Taspase1 expression as well as MLL cleavage.

We next asked whether Taspase1 was required to cleave MLL within mammalian cells. As a model system to test specificity, we co-expressed the p75 MLL substrate reporter together with Taspase1 in 293T cells. Taspase1 resulted in cleavage of wt p75 MLL but not the p75 CS1/2 mt reporter (FIG. 6A). Wt Taspase1, but not the T234A mutant Taspase1, enhanced the processing of p75 MLL to the final p42 product (FIGS. 1A and 6A). Only wt Taspase1, but not the T234A mutant of the nucleophile site demonstrated intramolecular processing into α/β fragments (FIGS. 3D and 6A). To assess the role of endogenous Taspase1, we designed duplex RNAi against Taspase1 which knocked down the expression of endogenous Taspase1 by ~80% (FIG. 6B). Taspase1 RNAi resulted in a ~50% decrease in the endogenous, processed C180 MLL fragment and in the appearance of full-length p500 MLL (FIG. 6B). In contrast, MLL RNAi resulted in the marked reduction of the C180 MLL fragment, but did not increase p500 MLL. In total, both the in vitro and in vivo cleavage assays confirm the role of Taspase1 in the proper processing of MLL.

Taspase1 is Required for Proper HOX Gene Expression

Figure 6C:
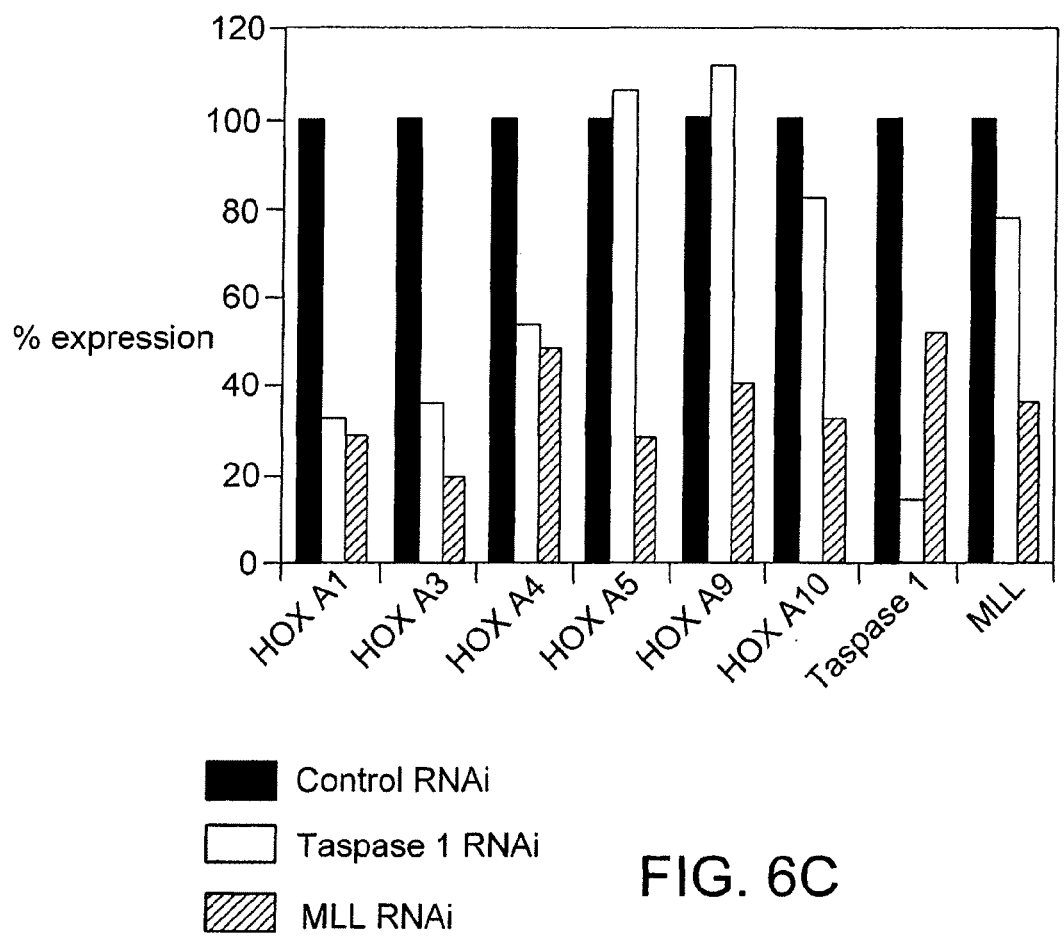
FIG. 6C depicts the results of a study indicating that knockdown of Taspase1 diminished the expression of the earlier expressed HOX genes, but not the later expressed HOX genes.
Figure 7:
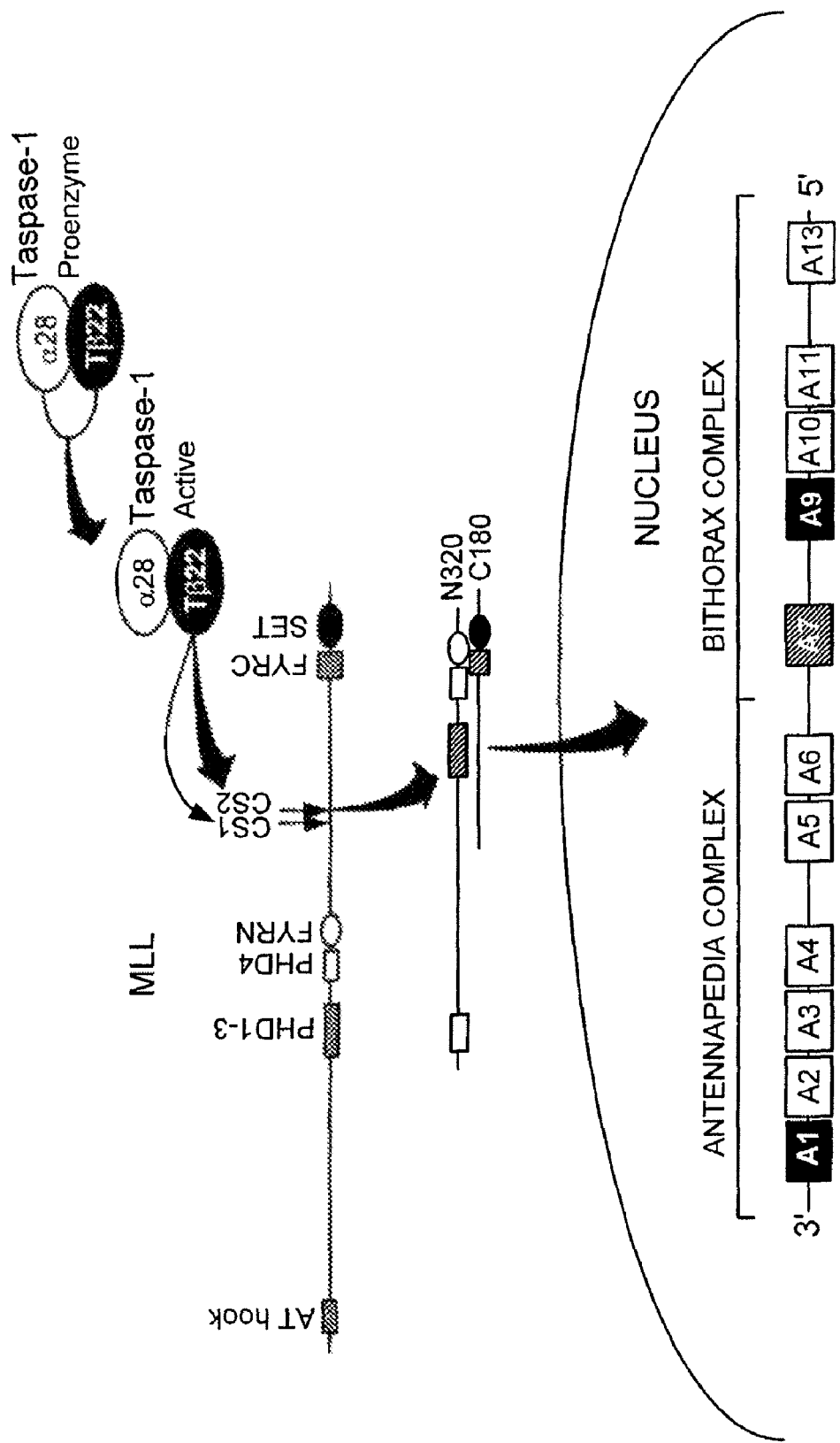
FIG. 7 is a schematic model depicting the intramolecular proteolysis of Taspase1 followed by MLL processing required for proper HOX gene expression.

Genetic studies in both mice and flies establish that Mll and trithorax regulate Hox and homeotic gene expression, respectively (Mazo et al., (1990) Proc. Natl. Acad. Sci. USA, 87:2112-2116; Yu et al., (1995) Nature, 378:505-508). Mice heterozygous for an Mll$^{-exon3LacZ}$ disruption demonstrated haploinsufficiency with bi-directional homeotic transformations and shifted anterior boundaries of several Hox genes (Yu et al., (1995) Nature, 378:505-508). Mll−/−deficient embryos and mouse embryonic fibroblasts (MEFs) demonstrated Mll is required for the maintenance of selected Hox gene expression (Hanson et al., (1999) Proc. Natl. Acad. Sci. USA, 96:14372-14377; Yu et al., (1998) Proc. Natl. Acad. Sci. USA, 95:10632-10636; Yu et al., (1995) Nature, 378: 505-508). As a first assessment of whether reduced Taspase1 activity would alter gene expression, we examined the gene expression profile of HeLa cells treated with the Taspase1 RNAi versus a control RNAi (FIG. 6B). Initial analysis of Affymetrix (HG-U133A) oligonucleotide array based RNA profiles indicated diminished expression of selected HOX genes (data not shown). Consequently, we used a quantitative RT-PCR approach to determine the relative expression of genes across the HOX A cluster. Of note, the knockdown of Taspase1 diminished the expression of the 3' located and "earlier" expressed genes in the HOX A cluster (A1, A3, and A4), but not those genes located more 5' and expressed "later" during embryonic development (A5, A9, and A10) (FIG. 6C). This selected attenuation contrasts with the global decrease in expression of most HOX A genes (A1 to A10) in cells with MLL knocked down (FIG. 6C). These data suggest the importance of Taspase1 in the correct expression of the early HOX A gene cluster (equivalent to the ANT-C cluster of *Drosophila*) (FIG. 7).

Inhibitors of Taspase1 Activity

Point Mutations of CS2 Cleavage Site

Figure 8:
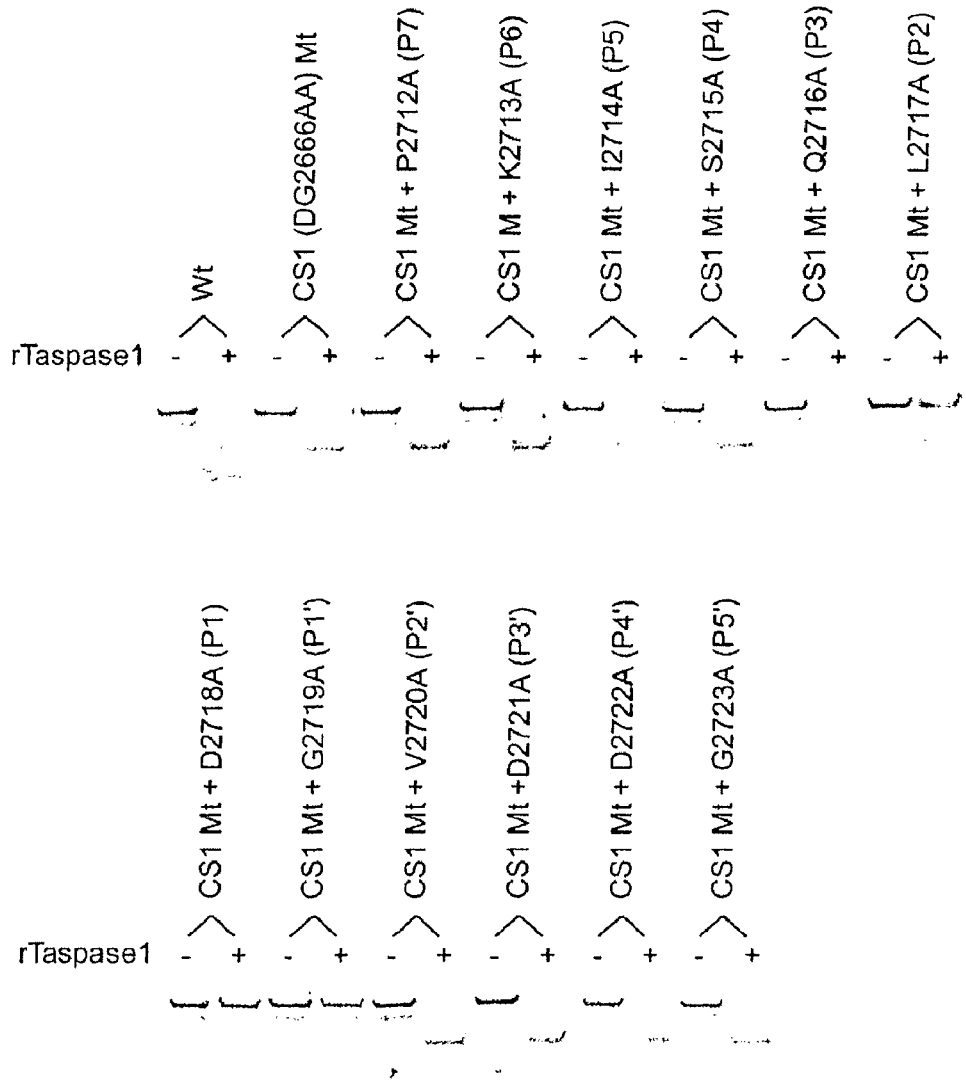
FIG. 8 depicts the results of a study demonstrating the effects of various point mutations in the CS2 cleavage site.

In order to identify essential amino acids relating to the CS2 cleavage site, mutant MLL substrates were prepared and labeled with $^{35}$S-methionine. The mutant MLL substrates included p45, a 300 amino acid portion of the MLL protein including the amino acids from 2500-2800. In order to prevent proteolytic cleavage at the CS1 cleavage site, the CS1 cleavage site was mutated at amino acids 2666-2670 from amino acid sequence DGADD to amino acid sequence AAADD. Individual mutant substrates of the CS1 mutated MLL substrate were then generated to provide mutants having point mutations at each of P7 through P5' (i.e., amino acids 2712-2723). In each mutant, the naturally occurring amino acid was substituted with an alanine as depicted in FIG. 8. The labeled mutant substrates were incubated with rTaspase1 and the results analyzed by SDS-PAGE followed by autoradiography. As seen in FIG. 8, mutation at P1 or P1' virtually eliminates any detectable proteolytic cleavage of the MLL substrate. Mutations at P2, P3 and P5 significantly reduce detectable proteolytic cleavage of the MLL substrate.

Polypeptide Inhibitors of Taspase1

Figure 9:
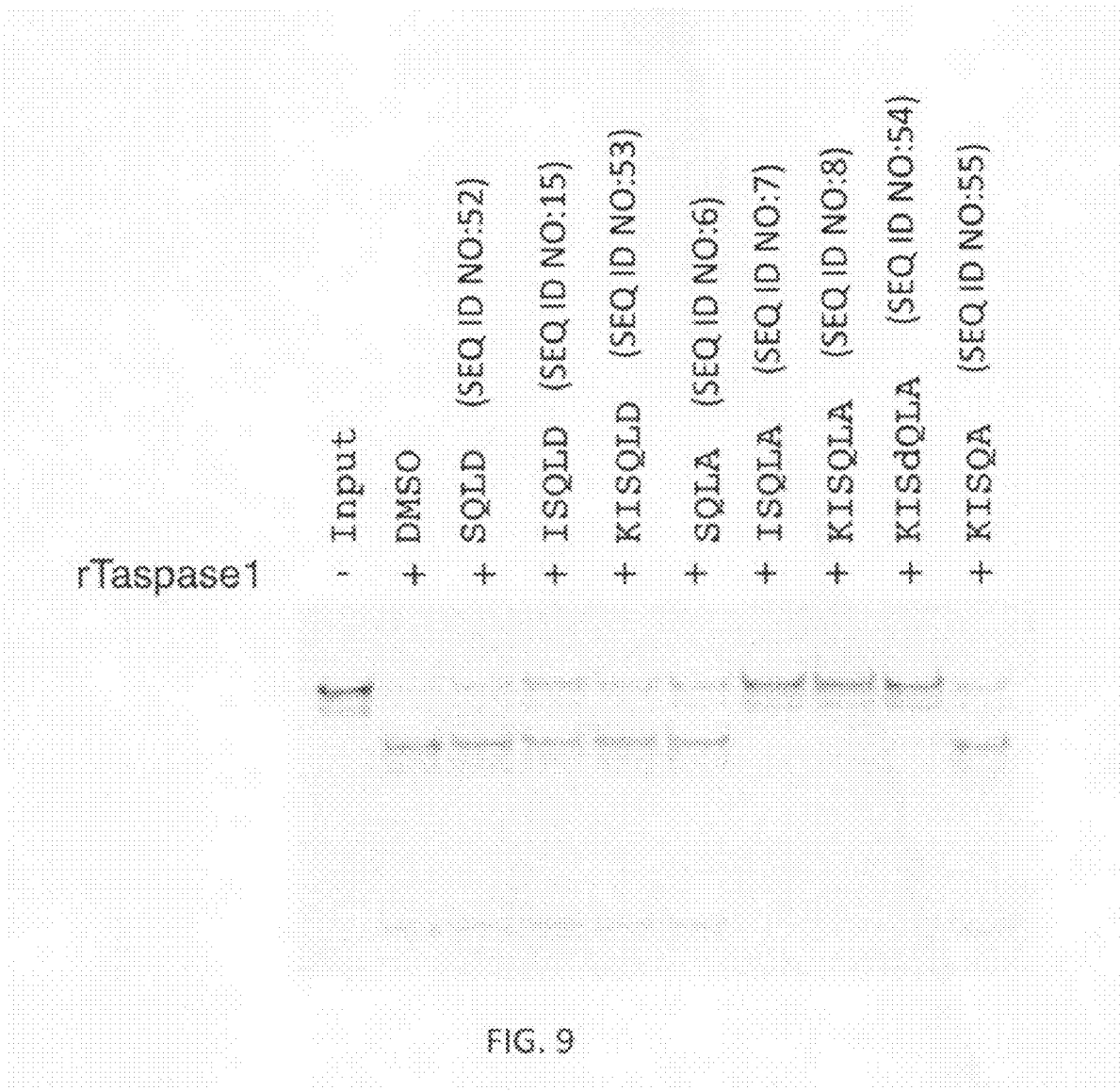
FIG. 9 depicts the results of a study demonstrating the effect of a change in length of peptide inhibitor on substrate cleavage and demonstrating the effect of a change in amino acid P1 from D to A on substrate cleavage.

Polypeptides of varying length (i.e., 4 to 7 amino acids in length) were prepared to identify preferred lengths and sequences of polypeptide inhibitors of Taspase1. The polypeptide inhibitors were based on the amino acid sequence that includes a upstream portion of the CS2 cleavage site of MLL as well as a portion of the CS2 cleavage site (See FIG. 1B and FIG. 9). The peptide inhibitors were purchased from Tufts University Peptide Core Facility and AnaSpec Inc. of San Jose, Calif. 1 mM of each of the inhibitors was incubated with 5 ng of rTaspase1 for 20 minutes before adding labeled substrate for another 60 minutes at 37° C. The results were analyzed by SDS-PAGE followed by autoradiography. As depicted in FIG. 9, polypeptides SQLD (SEQ ID NO:52), ISQLD (SEQ ID NO:15), and KISQLD (SEQ ID NO:53) had little inhibitory effect on the rTaspase1 enzyme. A likely reason for this result is due to the efficiency of the enzyme, where it cleaves the polypeptide inhibitor quickly, allowing the active site of Taspase1 to become available for another MLL substrate. On the other hand, in polypeptides where the P1 aspartate residue was substituted for an alanine residue (i.e., KISQLA (SEQ ID NO:8), KISdQLA (SEQ ID NO:54), and KISQA (SEQ ID NO:55)), inhibitory effect was observed. This suggests that the P1 is an essential amino acid for MLL cleavage activity. As seen in FIG. 9, polypeptides having greater than four amino acids have improved inhibitory effect. The results of the study also demonstrate the importance of the P2 amino acid, as mutation of P2 (i.e., omission of the leucine residue at P2) resulted in significantly decreased inhibition of rTaspase1 relative to the Taspase1 inhibition of the corresponding five amino acid alanine containing polypeptide having a P2 leucine (ISQLA) (SEQ ID NO:7).

Dose Response of Taspase1 with Two Polypeptide Inhibitors

Figure 10:
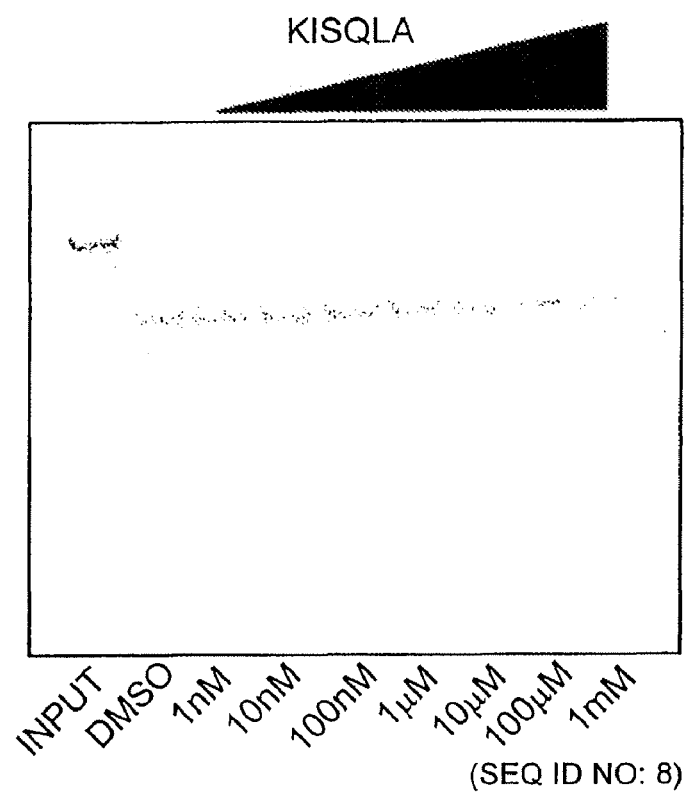
FIG. 10 depicts the results of a study demonstrating the difference in effectiveness of a five amino acid Taspase1 inhibitor and a six amino acid Taspase1 inhibitor.
Figure 10:
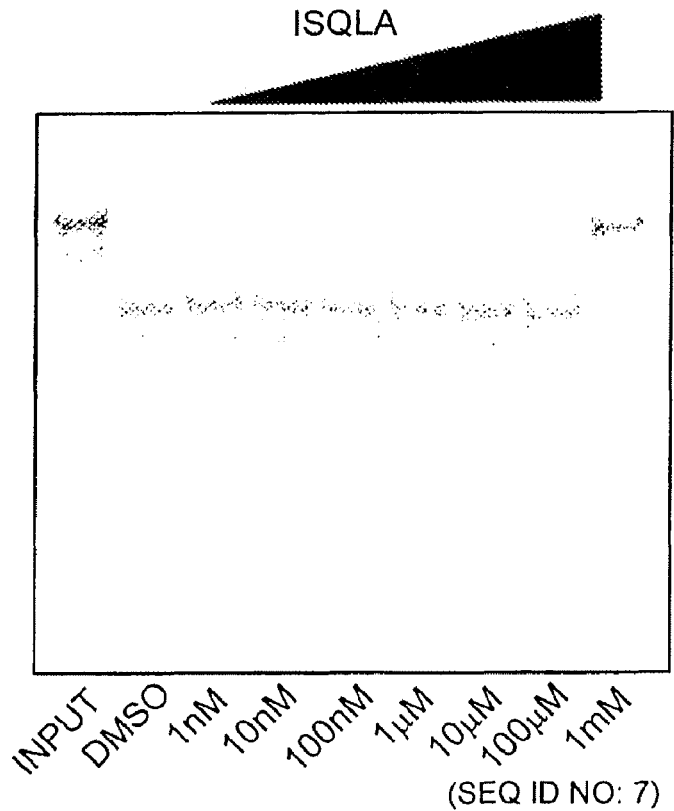

In order to determine a preferred length of polypeptide inhibitors of Taspase1, dose responses were tested for a six amino acid polypeptide inhibitor (KISQLA) (SEQ ID NO:8) and a five amino acid polypeptide inhibitor (ISQLA) (SEQ ID NO:7). The polypeptides were incubated at the concentrations depicted in FIG. 10 with 5 ng of rTaspase1 for 20 minutes before adding labeled MLL substrate for another 60 minutes at 37° C. The results were analyzed by SDS-PAGE followed by autoradiography. As can be seen in FIG. 10, the five amino acid polypeptide was a more effective inhibitor at lower concentrations than the corresponding six amino acid polypeptide. Thus, based on the results of this experiment, a five amino acid polypeptide inhibitor is likely to be more effective than a six amino acid polypeptide inhibitor.

Dose Responses of Polypeptide-Aldehyde Taspase1 Inhibitors

Figure 11A:
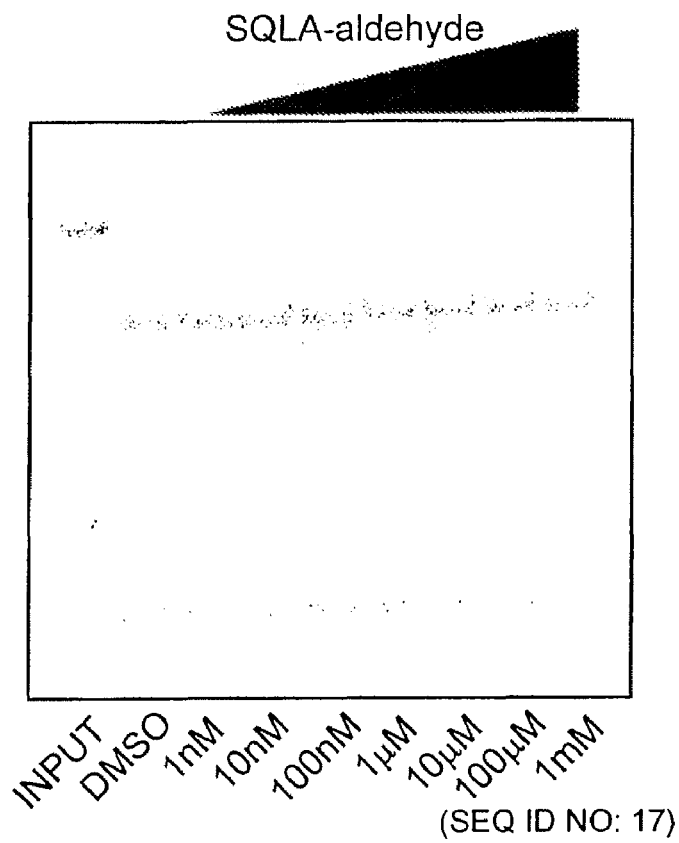
FIGS. 11A-C depicts the results of a study demonstrating the dose dependent inhibitory effects of three different amino acid aldehyde Taspase1 inhibitors, SQLA-aldehyde (SEQ ID NO: 17), SQLD-aldehyde (SEQ ID NO:9), and KISQLD-aldehyde (SEQ ID NO:11).
Figure 11B:
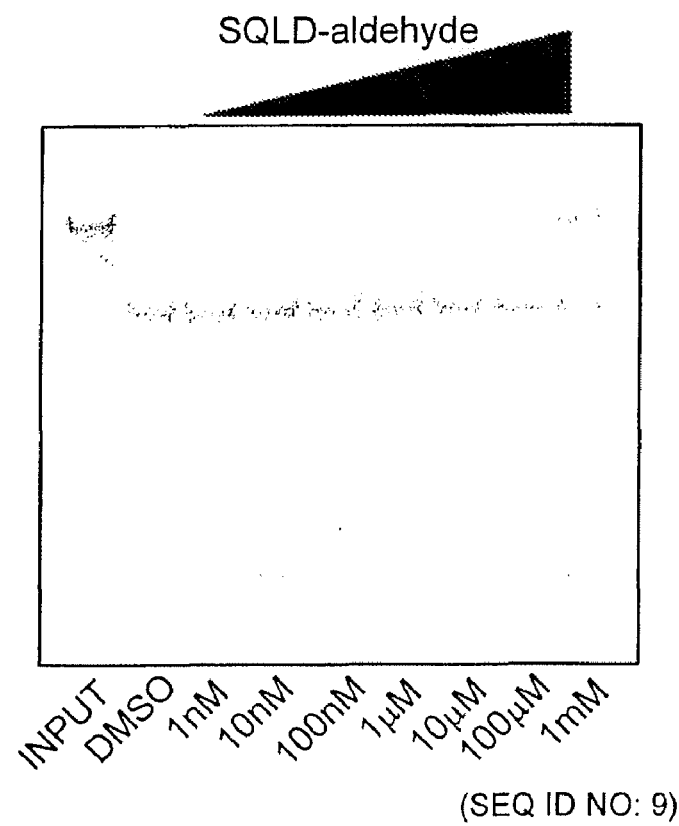
Figure 11C:
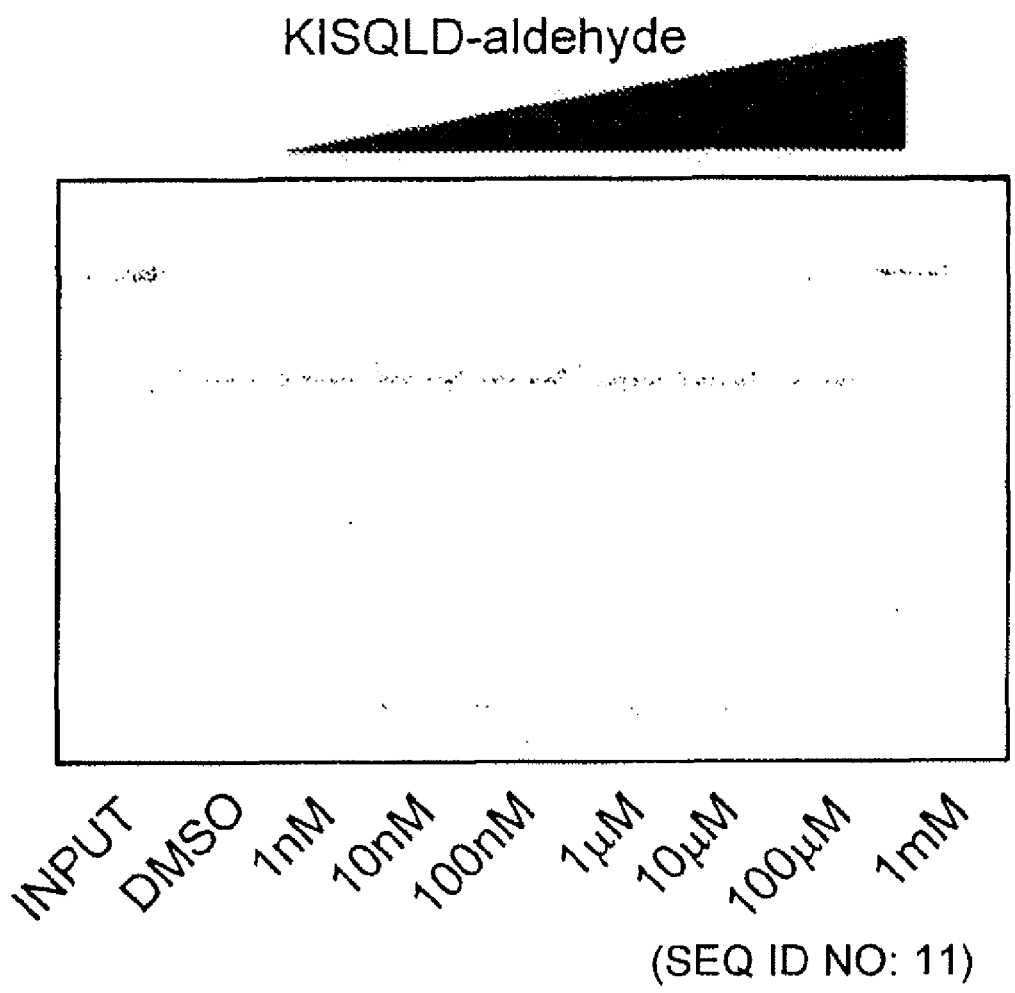

Three modified polypeptide inhibitors were prepared wherein the carboxy terminals of the polypeptides were replaced with an aldehyde (SQLA-aldehyde (SEQ ID NO:17), SQLD-aldehyde (SEQ ID NO:9), and KISQLD-aldehyde (SEQ ID NO:11)). Chemical syntheses of these modified polypeptides is well known to one of skill in the art, and the modified polypeptides are also are available commercially at AnaSpec Inc. of San Jose, Calif. The polypeptides were incubated in the concentrations depicted in FIGS. 11A-11C with 5 ng of rTaspase1 for 20 minutes before adding labeled MLL substrate for another 60 minutes at 37° C. The results were analyzed by SDS-PAGE followed by autoradiography. As depicted in FIGS. 11A and 11B, the SQLD-aldehyde (SEQ ID NO:9) was a more effective inhibitor than the SQLA-aldehyde (SEQ ID NO:17). Although the prior experiments showed that polypeptide sequences including SQLA (SEQ ID NO:6) were more effective Taspase1 inhibitors than polypeptide sequences including SQLD (SEQ ID NO:52), the modification of the C-terminal portion of the peptide significantly reduces the cleavage efficiency of the enzyme by causing a reversible (but very inefficiently reversible) bond between the polypeptide inhibitor and the enzyme. Accordingly, the modified polypeptides can keep the active site of the enzyme occupied for a greater length of time, blocking entrance of the MLL substrate from entering the active site as required for cleavage. Moreover, experimental studies showed that the six amino acid aldehyde (KISQLD) (SEQ ID NO:53) was more effective than both of the four amino acid aldehyde. (See FIG. 11C.).

Methods and Materials

Plasmid Construction and Antibody Production

PCR fragments consisting of MLL aa 2,400 to 2,900 derived from either wild type or noncleavable MLL mt (CS1/CS2 mt) were inserted into a Myc/Flag doubly-tagged eukaryotic expression vector for transient transfection assays. These constructs also contain a 5' T7 promoter for generating in vitro transcription/translation product of $^{35}$S-methionine labeled p75 MLL substrates. Full-length Taspase1 was cloned from 293T cell cDNA and inserted into the Myc/Flag doubly-tagged expression vector, a Protein C tagged vector, and a His-tagged bacteria expression vector, ET15b (Novagen). Taspase1 mutants were generated using QuikChange site-directed mutagenesis kit (Stratagene). Rabbit anti-Taspase1 polyclonal antibody was raised against aa 7 to 212 of purified recombinant human Taspase1. Transient transfection, in vitro transcription/translation, $^{35}$S-methionine labeling, and immunoblot assays were performed as previously described (Hsieh et al., (2003) Mol. Cell. Biol., 23:186-194).

In Vitro Cleavage Assays $^{35}$S-methionine labeled MLL substrate was incubated with 2 μl of indicated subcellular fractions or specified amounts of rTaspase1 in cleavage buffer (100 mM HEPES [pH 7.9], 5 mM MgCl$_2$, 20 mM KCl, 5 mM DTT, and 10% sucrose) for 1 hour at 37° C. or indicated periods of time. Protease inhibitors utilized include 8.5 μM Phosphoramidon, 100 μM TLCK, 100 µM TPCK, 5 mM Iodoacetamide, 5 mM N-Ethylmaleimide, 0.3 µM Aprotinin, 100 µM Leupeptin, 1 µM Pepstatin, 1× Complete protease inhibitor cocktail (Roche), 100 µM Antipain, 100 µM APMSF, 10 µM Bestatin, 25 µM ALLN, 100 µM Chymostatin, 10M E-64, 5 mM EDTA, 1 mM PMSF, 1 mM EGTA, 50 µM BAF (Boc-Aspartyl-FMK), and 50 µM z-VAD (z-VAD-FMK).

Purification and LC-MS/MS

Human 293T cells from one hundred 15-cm dishes were collected and incubated in hypotonic buffer (10 mM HEPES [pH 7.9], 1.5 mM $MgCl_2$, 10 mM KCl, 0.2 mM PMSF, 1 mM EDTA, 1 mM EDTA, 1 mM EGTA, and protease inhibitor cocktail [Roche]) for 15 min on ice. Supplemented protease inhibitors were omitted during the initial characterization of MLL cleaving protease. Cells were homogenized using a glass dounce and the homogenized cellular extract was subjected to centrifugal fractionation. Nuclei (Nuc) and unbroken cells were twice separated at 700 g for 10 min. The heavy membrane (HM) fraction pellet was collected after two centrifugations of the supernatant at 7,000 g for 10 minutes. The resulting supernatant was centrifuged at 100,000 g for 30 minutes to yield the light membrane pellet (LM) and final soluble fraction (S100). Proteins were solubilized in buffer A (20 mM HEPES [pH 7.9], 100 mM KCl, 1.5 mM $MgCl_2$, 0.2 mM PMSF, 1 mM DTT, 1 mM EDTA, 1 mM EGTA, 0.1% Tween 20, and 10% glycerol) with additional 0.5% of Tween 20. Solubilized LM fraction was applied to a P11 column and the bound protease was eluted with gradients of KCl. Positive fractions were collected and dialyzed against buffer B (10 mM HEPES [pH 7.9], 100 mM KCl, 1 mM $MgCl_2$, 10 uM $CaCl_2$, 0.2 mM PMSF, 1 mM DTT, 1 mM EDTA, 1 mM EGTA, 10% glycerol, 0.1% Tween 20, and 10 mM potassium phosphate [pH 7.9]) and applied to a hydroxyapatite column. Elution was performed with a phosphate gradient and the protease positive fractions were dialyzed against buffer A before loading onto indicated chromatographic columns. LC-MS/MS was performed by the Taplin Biological Mass Spectrometry Facility at the Harvard Medical School.

Recombinant Enzyme and Edman Degradation Analysis

His-tagged Taspase1 was expressed in BL21(DE3) cells and purified with a TALON column (Clontech). N-terminal protein sequencing was performed by Molecular Biology Core Facility at the Dana-Farber Cancer Institute.

RNAi, Reverse Transcription and Quantitative PCR

HeLa cells were transfected with indicated duplex RNAi (Dharmacon) using oligofectamine (Invitrogen). Double-stranded ribo-oligonucleotides with overhanging 3' deoxy TT were prepared to target mRNAs of either hTaspase1 (GACUCACAUUUCAAGACUU) (SEQ ID NO:56) or hMLL (GAAGUCAGAGUGCGAAGUC) (SEQ ID NO:57). Cells harvested 72 hours after transfection were either lysed in RIPA buffer for immunoblots or with Trizol (Invitrogen) for RNA purification using RNeasy (Qiagen). Reverse transcription were performed with oligo-dT primers using Superscript II (Invitrogen). Quantitative PCR was performed in triplicate using indicated gene specific primers (supplementary methods) with SYBR green (PE biosystems) on the ABI Prism 7700 sequence detection system.

Determination of Sequence Homology or Identity

The "percent identity" of two amino acid sequences or of two nucleic acids is determined using the algorithm of Karlin and Altschul (1990) *Proc. Natl. Acad. Sci.* USA 87:2264-2268, modified as in Karlin and Altschul (1993) *Proc. Natl. Acad. Sci.* USA 90:5873-77. Such an algorithm is incorporated into the BLASTN and BLASTX programs (version 2.0) of Altschul et al. (1990) *J. Mol. Biol.* 215:403-410. BLAST nucleotide searches can be performed with the BLASTN program, score=100, wordlength=12 to obtain nucleotide sequences homologous to the nucleic acid molecules of the invention. BLAST protein searches can be performed with the BLASTX program, score=50, wordlength=3 to obtain amino acid sequences homologous to the protein molecules of the invention. Where gaps exist between two sequences, Gapped BLAST can be utilized as described in Altschul et al. (1997) *Nucleic Acids Res.* 25:3389-3402. When utilizing BLAST and Gapped BLAST programs, the default parameters of the respective programs (e.g., BLASTX and BLASTN) can be used (available on the Internet at ncbi.nlm.nih.gov).

Particularly preferred Taspase1 polypeptides have an amino acid sequence substantially identical to the amino acid sequence of SEQ ID NO:1. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%, 95%, 96%, 97%, 98% or 99% identity to SEQ ID NO:1 are termed substantially identical.

Isolated Taspase1 Polypeptides

In another aspect, the invention features, an isolated Taspase1 protein or fragment, e.g., a biologically active portion. Taspase1 protein can be isolated from cells or tissue sources using standard protein purification techniques. Taspase1 protein or fragments thereof can be produced by recombinant DNA techniques or synthesized chemically.

The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

The Taspase1 proteins, or fragment thereof, can differ from the corresponding sequence in SEQ ID: 1, for example, by at least one but by less than 20, 15, 10 or 5 amino acid residues. Alternatively, it can differ from the corresponding sequence in SEQ ID NO:1 by at least one residue but less than 20%, 15%, 10% or 5% of the residues in it differ from the corresponding sequence in SEQ ID NO:1. The differences can be conservative, non-conservative or both.

In one embodiment, the protein includes an amino acid sequence at least about 80%, 85%, 90%, 95%, 98%, 99% or more homologous to SEQ ID NO:1.

The peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-NH2 protected by either t-Boc or F-moc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Alternatively, the longer synthetic peptides can be synthesized by well known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which have a stimulatory or inhibitory effect on, for example, Taspase1 expression or Taspase1 activity (e.g., proteolytic cleavage of an MLL substrate), have a stimulatory or inhibitory effect on, for example, the expression or activity of a Taspase1 substrate (e.g., MLL), or which bind to Taspase1. Desirable inhibitors of Taspase1 activity reduce the proteolytic activity of Taspase1 and include those which reduce cleavage of MLL at CS1 or CS2 or both CS1 and CS2. Inhibitors can be identified by their ability to reduce cleavage of MLL family proteins or some other substrate, e.g., a fragment of MLL containing CS1 and/or CS2 such as the p75 fragment of MLL (amino acids 2400-2900 of SEQ ID NO: 3) or the p45 fragment of MLL (amino acids 2500-2800 of SEQ ID NO: 3).

In one embodiment, the invention includes assays to determine the ability of a candidate compound to modulate the proteolytic cleavage of a Taspase1 substrate such as MLL or a fragment of MLL (e.g., an MLL fragment containing CS1 and/or CS2, such as the p75 fragment or the p45 fragment). Taspase1 is exposed to a candidate compound in the presence of MLL or a fragment thereof under conditions sufficient to allow cleavage of the MLL or MLL fragment (e.g., 37° C. for about 60 minutes). The reaction mixture is then analyzed (for example, using labeled MLL or a labeled MLL fragment and SDS-PAGE followed by autoradiography) to determine whether a candidate compound modulates (e.g., stimulates or inhibits) the activity of Taspase1 (e.g., the proteolytic cleavage of MLL or an MLL fragment). In some instances, it is desirable for the candidate compound to inhibit the activity of Taspase1 (e.g., decrease the level of MLL proteolytic cleavage). In other instances, it is desirable for the compound to enhance or stimulate the activity of Taspase1 (e.g., increase the level of MLL proteolytic cleavage).

The $K_i$ of candidate compounds can be determined using, for example, a titration assay. Taspase1 can be exposed to varying concentrations of candidate compound (e.g., 1 nM, 10 nM, 100 nM, 1 μM, 10 μM, 100 μM, 1 mM, and 10 mM) in the presence of a substrate such as MLL or a fragment thereof (e.g., a CS1 and/or CS2 containing MLL fragment). The effect of each concentration of candidate compound is then analyzed (e.g., using labeled MLL and SDS-PAGE followed by autoradiography) to determine the effect of the candidate compound on Taspase1 activity (e.g., inhibition of MLL cleavage) at varying concentrations, which can be used to calculate the $K_i$ of the candidate compound. The candidate compound can modulate Taspase1 activity in a competitive or non-competitive manner.

The assays described herein can be performed with individual candidate compounds or can be performed with a plurality of candidate compounds. Where the assays are performed with a plurality of candidate compounds, the assays can be performed using mixtures of candidate compounds or can be run in parallel reactions with each reaction having a single candidate compound. The test compounds or agents can be obtained using any of the numerous approaches in combinatorial library methods known in the art.

In one embodiment, an assay is a cell-based assay in which a cell that expresses a Taspase1 protein or biologically active portion thereof is contacted with a test compound, and the ability of the test compound to modulate Taspase1 activity is determined. Determining the ability of the test compound to modulate Taspase1 activity can be accomplished by monitoring, for example, MLL cleavage.

In yet another embodiment, a cell-free assay is provided in which a Taspase1 protein or biologically active portion thereof is contacted with a test compound and the ability of the test compound to modulate Taspase1 activity is evaluated. Preferred biologically active portions of the Taspase1 proteins to be used in assays of the present invention include fragments which have the ability to proteolytically cleave a Taspase1 substrate, e.g., MLL or a CS1 and/or CS1 containing fragment thereof such as the p75 fragment or the p45 fragment. Preferred biologically active portions of the Taspase1 proteins used in the assays described herein include fragments that have the ability to proteolytically cleave a Taspase1 substrate, e.g., MLL. For example a cell-free assay can involve preparing a reaction mixture of a Taspase1 polypeptide or a fragment thereof and the candidate compound under conditions and for a time sufficient to allow the two components to interact and bind, thus forming a complex that can be removed and/or detected. Candidate compounds that have the ability to form a covalent bond with Taspase1 can be detected, for example, by preparing a labeled candidate compound (e.g., a modified polypeptide including a peptide aldehyde and a chloromethylketone or a fluoromethylketone peptide derivative), exposing Taspase1 to the candidate compound, and subsequently measuring the amount of radioactive Taspase1. Alternatively, cell free assays can be used to determine the ability of the compound to modulate (i.e., enhance or inhibit) Taspase1 activity (e.g., MLL cleavage), for example, using labeled MLL or a CS1 and/or CS2 containing fragment thereof.

In one embodiment, a cell free assay can measure the ability of Taspase1 to proteolytically cleave a substrate using a peptide-based fluorescence resonance energy transfer (FRET) assay. FRET assays are known to one of skill in the art. (see, for example, Cummings G. et al., (2002) PNAS 99:6603-6) For example, Taspase1 or a fragment thereof can be incubated in the presence of a doubly labeled peptide substrate (e.g., MLL, a p75 fragment of MLL, a p45 fragment of MLL, or a fragment of MLL containing a CS1 and/or a CS2) and a candidate compound, wherein the peptide substrate is doubly labeled with suitable fluorophore/quencher pair (e.g., a coumarin fluorophore paired with either DAB-CYL or QSY-35 as the quencher). After incubation under conditions to allow proteolytic cleavage of the substrate, the peptide is then removed from the mixture and the peptide substrates and products separated (e.g., using HPLC). The degree of inhibition of the candidate compound is then measured by a change in fluorescence relative to a control sample, wherein a decrease in Taspase1 activity (e.g., MLL cleavage) corresponds to a relative decrease in fluorescence and an increase Taspase1 activity corresponds to a relative increase in fluorescence.

In another embodiment, Taspase1 or a fragment thereof is incubated in the presence of a candidate compound and a substrate (e.g., MLL, a p75 fragment of MLL, a p45 fragment of MLL, or a fragment of MLL containing a CS1 and/or a CS2). After incubation under conditions sufficient to allow proteolytic cleavage of the substrate, the reaction mixture is analyzed using MS (e.g., LC/MS, ESI-LC/MS, FAB-MS). (see, for example, Zhu et al., (2003) J. Biol. Chem., 278: 22418-23) Quantitative measurements of substrate conversion can be made using ratiometric analysis of the substrate (e.g., MLL or a fragment thereof) and product (e.g., the cleaved MLL or fragment thereof) peak areas in the extracted ion chromatograms of each species. The ratios of substrate and product in the presence of a candidate compound can be compared to a control to determine whether the candidate compound had an inhibitory effect or an enhancing effect on the Taspase1 activity (e.g., proteolytic cleavage of substrate).

In one embodiment, Taspase1, Taspase1 fragment, or test compound is anchored onto a solid phase. The Taspase1/test compound complexes anchored on the solid phase can be detected at the end of the reaction. Preferably, the Taspase1 or a fragment thereof is anchored onto a solid surface, and the test compound (which is not anchored) can be labeled, either directly or indirectly, with detectable labels discussed herein.

Cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) Trends Biochem. Sci. 18:284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) Current Protocols in Molecular Biology, J. Wiley: New York). Such resins and chromatographic techniques are known to one skilled in the art (see, e.g., Heegaard, N. H., (1998) J Mol Recognit 11: 141-8; Hage, D. S., and Tweed, S. A. (1997) J Chromatogr. B. Biomed. Sci. Appl. 699:499-525). Further, fluorescence energy transfer may also be conveniently utilized, as described herein, to detect binding without further purification of the complex from solution.

These assays can be conducted in a heterogeneous or homogeneous format. Heterogeneous assays involve anchoring either the target gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, candidate compounds that interfere with the interaction between Taspase1 and an MLL polypeptide, e.g., by competition, can be identified by conducting an MLL proteolytic cleavage reaction in the presence of the candidate compound.

In a heterogeneous assay system, either the Taspase1 or the MLL polypeptide, is anchored onto a solid surface (e.g., a microtiter plate), while the non-anchored species is labeled either directly or indirectly. The anchored species can be immobilized by non-covalent or covalent attachments. Alternatively, an immobilized antibody specific for the species to be anchored can be used to anchor the species to the solid surface.

In an alternate embodiment of the invention, a homogeneous assay can be used. For example, a preformed complex of Taspase1 or a fragment thereof and MLL or a fragment thereof can be prepared in that either the Taspase1 or MLL are labeled, but the signal generated by the label is quenched due to complex formation (see, e.g., U.S. Pat. No. 4,109,496 that utilizes this approach for immunoassays). The addition of candidate compound that competes with and displaces one of the species from the preformed Taspase1/MLL substrate complex will result in the generation of a signal above background. In this way, test substances that disrupt Taspase1/MLL interaction can be identified. In some instances it is desirable to modify the MLL substrate in order to prevent proteolytic cleavage of the substrate upon interaction with Taspase1, thus maintaining the MLL substrate in the Taspase1/MLL substrate complex for a greater length of time.

This invention further pertains to novel agents identified by the above-described screening assays. Accordingly, it is within the scope of this invention to further use an agent identified as described herein (e.g., a Taspase1 modulating agent such as a Taspase1 inhibitor, an antisense Taspase1 nucleic acid molecule, a Taspase1-specific antibody, or a Taspase1-binding partner) in an appropriate animal model to determine the efficacy, toxicity, side effects, or mechanism of action, of treatment with such an agent. Furthermore, novel agents identified by the above-described screening assays can be used for treatments as described herein.

Inhibitors of Taspase1 Activity

In one embodiment, the invention includes an inhibitor of Taspase1 activity. The inhibitor can be, for example a polypeptide, a modified polypeptide, or a peptidomimetic. Preferred peptides are of between about 5 and 7 amino acids in length. However, longer and shorter polypeptides are also envisioned. Preferred polypeptides include amino acid sequences of Ile-Xaa-Gln-Leu-Xaa (SEQ ID NO:58) (e.g., Ile-Ser-Gln-Leu-Asp (SEQ ID NO:16) or Ile-Ser-Gln-Leu-Ala (SEQ ID NO:7)).

In some instances, the polypeptides are modified at the C-terminal end or the N-terminal end. Modification of the C-terminal end can provide a chemically reactive group that will form a covalent bond between Taspase1 and the polypeptide, wherein the bond is either irreversible or inefficiently reversible, thus allowing the polypeptide to occupy the active site of Taspase1, for a longer period of time. Some examples of C-terminal modifications include replacing the carboxy end of the polypeptide with an aldehyde, a chloromethylketone or a fluoromethylketone. Other C-terminal modifications are envisioned for the polypeptide inhibitors described herein. Methods of modification of polypeptides are well known to one of skill in the art.

In some instances, it is desirable to modify a backbone of a polypeptide in order to improve the bioavailability of the polypeptide, improve the potency of the polypeptide, or prevent (e.g., slow) the metabolism of the polypeptide in the body. Preferably, one or more hydrolyzable amide bonds of the polypeptide are replaced with a non-hydrolyzable isosteric group of the amide or the transition state of the amide during hydrolysis. Some examples of peptide backbone modifications include replacing the amide bond with a hydroxyethylamine, hydroxyethylene, hydroxyethylurea, urea, norstatine, a C2 symmetric monoalcohol, or diol(dihydroxyethylene). (See e.g., Abdel-Rahman et al., (2002) Cur. Med. Chem. 9:1905-1922.) Other peptide modifications are also envisioned. For example, the use of a terminal (e.g., N-terminal or C-terminal) thiazole group can increase the chemical stability towards metabolic oxidation while maintaining water solubility, or the addition of a pyridyl group to the polypeptide (e.g., a terminal portion of the polypeptide) can improve the water solubility of the polypeptide.

Small molecule inhibitors are also envisioned. For example, the small molecule inhibitors can include heterocyclic compounds having motifs that mimic the CS1 or CS2 binding sites of MLL.

Isolated Nucleic Acid Molecules

In one aspect the invention provides an isolated or purified, nucleic acid molecule that encodes a Taspase1 polypeptide described herein, e.g., a full-length Taspase1 protein or a fragment thereof, e.g., a biologically active portion of Taspase1 protein.

In one embodiment, an isolated nucleic acid molecule of the invention includes the nucleotide sequence shown in SEQ ID NO:2, or a portion of any of these nucleotide sequences. In one embodiment, the nucleic acid molecule includes sequences encoding the human Taspase1 protein, as well as 5' untranslated sequences.

In another embodiment, an isolated nucleic acid molecule of the invention includes a nucleic acid molecule which is a complement of the nucleotide sequence shown in SEQ ID NO:2, or a portion of any of these nucleotide sequences. In other embodiments, the nucleic acid molecule of the invention is sufficiently complementary to the nucleotide sequence shown in SEQ ID NO:2, such that it can hybridize (e.g., under a stringency condition described herein) to the nucleotide sequence shown in SEQ ID NO:2, thereby forming a stable duplex.

In one embodiment, an isolated nucleic acid molecule of the present invention includes a nucleotide sequence which is at least about 80%, 85%, 90%, 91%, 92%, 93%, 94%, 95%, 96%, 97%, 98%, 99%, or more homologous to the entire length of the nucleotide sequence shown in SEQ ID NO:2, or a portion, preferably of the same length, of any of these nucleotide sequences.

Antisense Nucleic Acid Molecules, Ribozymes, RNAi, and Modified Taspase1 Nucleic Acid Molecules To inhibit the expression of Taspase1, one can administer one or more nucleic acid inhibitory agents, such as antisense RNA, a small inhibitory RNA (i.e., RNAi), or a ribozyme, any of which can be designed to target a sequence within Taspase1 or a fragment thereof.

In another aspect, the invention features, an isolated nucleic acid molecule which is antisense to Taspase1. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire Taspase1 coding strand, or to only a portion thereof. For example, the antisense oligonucleotide can be complementary to the region surrounding the translation start site of Taspase1 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a Taspase1 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein.

Taspase1 Chimeric or Fusion Proteins

In another aspect, the invention provides Taspase1 chimeric or fusion proteins. As used herein, a Taspase1 "chimeric protein" or "fusion protein" includes a Taspase1 polypeptide linked to a non-Taspase1 polypeptide. A "non-Taspase1 polypeptide" refers to a polypeptide having an amino acid sequence corresponding to a protein which is not substantially homologous to the Taspase1 protein, e.g., a protein which is different from the Taspase1 protein and which is derived from the same or a different organism. The Taspase1 polypeptide of the fusion protein can correspond to all or a portion e.g., a fragment described herein of a Taspase1 amino acid sequence. In a preferred embodiment, a Taspase1 fusion protein includes at least one (or two) biologically active portion of a Taspase1 protein. The non-Taspase1 polypeptide can be fused to the N-terminus or C-terminus of the Taspase1 polypeptide.

The Taspase1 fusion proteins of the invention can be incorporated into pharmaceutical compositions and administered to a subject in vivo and can be used to affect the bioavailability of a Taspase1 substrate. Additionally, Taspase1 fusion proteins may be useful therapeutically for the treatment of disorders caused by, for example, (i) aberrant modification or mutation of a gene encoding a Taspase1 protein; (ii) misregulation of the Taspase1 gene; and (iii) aberrant post-translational modification of a Taspase1 protein.

Expression vectors are commercially available that already encode a fusion moiety (e.g., a GST polypeptide). A Taspase1-encoding nucleic acid can be cloned into such an expression vector such that the fusion moiety is linked in frame to the Taspase1 protein.

Anti-Taspase1 Antibodies

The Taspase1 polypeptide can be used to produce an anti-Taspase1 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL).

The term "antigen-binding fragment" of an antibody (or simply "antibody portion," or "fragment"), as used herein, refers to one or more fragments of a full-length antibody that retain the ability to specifically bind to the antigen, e.g., Taspase1 polypeptide or fragment thereof. These antibody fragments are obtained using conventional techniques known to those with skill in the art, and the fragments are screened for utility in the same manner as are intact antibodies.

The anti-Taspase1 antibody can be a polyclonal or a monoclonal antibody. In other embodiments, the antibody can be recombinantly produced, e.g., produced by phage display or by combinatorial methods.

Phage display and combinatorial methods for generating anti-Taspase1 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) Proc. Natl. Acad. Sci. USA 89:5547, and Paillard (1989) Human Gene Therapy 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) Science 249:374-379) and the a-fetoprotein promoter (Campes and Tilghman (1989) Genes Dev. 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a Taspase1 nucleic acid molecule within a recombinant expression vector or a Taspase1 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell.

A host cell can be any prokaryotic or eukaryotic cell. For example, a Taspase1 protein can be expressed in bacterial cells (such as *E. coli*), insect cells, yeast or mammalian cells (such as Chinese hamster ovary cells (CHO) or COS cells (African green monkey kidney cells CV-1 origin SV40 cells; Gluzman (1981) Cell I23:175-182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

Pharmaceutical Compositions

The nucleic acids and polypeptides, fragments thereof, anti-Taspase1 antibodies, inhibitors of Taspase1 activity, or enhancers of Taspase1 activity (also referred to herein as "active compounds") of the invention can be incorporated into pharmaceutical compositions. Such compositions typically include the nucleic acid molecule, protein, antibody, or inhibitor and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. (1997) J. Acquired Immune Deficiency Syndromes and Human Retrovirology 14:193).

The present invention encompasses agents which modulate expression or activity (e.g., inhibit Taspase1 activity or enhance Taspase1 activity). An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Methods of Treatment

The present invention provides for both prophylactic and therapeutic methods of treating a subject at risk of (or susceptible to) a disorder or having a disorder associated with aberrant or unwanted Taspase1 expression or activity (e.g., MLL proteolytic cleavage). As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

It is possible that some Taspase1 disorders can be caused, at least in part, by an abnormal level of Taspase1, or by the presence of Taspase1 exhibiting abnormal activity. As such, the reduction in the level and/or activity of Taspase1 would bring about the amelioration of disorder symptoms. Moreover, even normal levels of activity of Taspase1 may lead to expression of HOX genes that are present in malignant cells, thus consequently inhibiting Taspase1 activity could reduce the level of target proteins such as the HOX products and ameliorate the disorder (e.g., a cancer).

The Taspase1 molecules can act as novel diagnostic targets and therapeutic agents for controlling one or more of cellular proliferative and/or differentiative disorders, for example cancer, e.g., carcinoma, sarcoma, metastatic disorders or hematopoietic neoplastic disorders, e.g., leukemias.

As used herein, the terms "cancer", "hyperproliferative" and "neoplastic" refer to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

As discussed, successful treatment of Taspase1 dependent disorders can be brought about by techniques that serve to inhibit the expression or activity of Taspase1. For example, compounds, e.g., an agent identified using an assays described above, that proves to exhibit negative modulatory activity (e.g., inhibits MLL proteolysis), can be used in accordance with the invention to ameliorate symptoms of Taspase1 dependent disorders, such as cancer. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')2 and Fab expression library fragments, scFV molecules, and epitope-binding fragments thereof).

Further, antisense, siRNA (small interfering RNA), and ribozyme molecules that inhibit expression of Taspase1 can also be used in accordance with the invention to reduce the level of Taspase1 expression, thus effectively reducing the level of target gene activity. Still further, triple helix molecules can be utilized in reducing the level of Taspase1 activity. Antisense, ribozyme, siRNA, and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

The identified compounds that inhibit target gene expression, synthesis and/or activity can be administered to a patient at therapeutically effective doses to prevent, treat or ameliorate Taspase1 disorders. A therapeutically effective dose refers to that amount of the compound sufficient to result in amelioration of symptoms of the disorders. Toxicity and therapeutic efficacy of such compounds can be determined by standard pharmaceutical procedures as described above.

Another aspect of the invention pertains to methods of modulating Taspase1 expression or activity for therapeutic purposes. Accordingly, in an exemplary embodiment, the modulatory method of the invention involves contacting a cell with a Taspase1 or agent that modulates one or more of the activities of Taspase1 protein activity associated with the cell. An agent that modulates Taspase1 protein activity can be an agent as described herein, such as a nucleic acid or a protein, a naturally-occurring target molecule of a Taspase1 protein (e.g., a Taspase1 substrate or receptor), a Taspase1 antibody, a Taspase1 agonist or antagonist, a peptidomimetic of a Taspase1 agonist or antagonist, or other small molecule.

In one embodiment, the agent stimulates Taspase1 activity. Examples of such stimulatory agents include active Taspase1 protein and a nucleic acid molecule encoding Taspase1. In another embodiment, the agent inhibits one or more Taspase1 activities. Examples of such inhibitory agents include antisense Taspase1 nucleic acid molecules, anti-Taspase1 antibodies, and Taspase1 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a Taspase1 protein or nucleic acid molecule.

Stimulation of Taspase1 activity is desirable in situations in which Taspase1 is abnormally downregulated and/or in which increased Taspase1 activity is likely to have a beneficial effect. Likewise, inhibition of Taspase1 activity is desirable in situations in which Taspase1 is abnormally upregulated and/or in which decreased Taspase1 activity is likely to have a beneficial effect.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising an isolated polypeptide that inhibits the protease activity of the Taspase1 of SEQ ID NO: 1, wherein the isolated polypeptide consists essentially of at least 4, but not more than 5 contiguous amino acids, wherein the at least 4, but not more than 5 contiguous amino acids comprise the amino acid sequence SQLA (SEQ ID NO:6).

2. A composition comprising an isolated polypeptide that inhibits the protease activity of the Taspase1 of SEQ ID NO: 1, wherein the isolated polypeptide consists essentially of at least 5, but not more than 7 contiguous amino acids, wherein the at least 5, but not more than 7 contiguous amino acids comprise the amino acid sequence ISQLA (SEQ ID NO:7).

3. The composition of claim 1, wherein the C-terminal or N-terminal end of the isolated polypeptide is a chemically reactive group that will form a covalent bond between the Taspase1 and the isolated polypeptide.

4. The composition of claim 3, wherein the chemically reactive group is a C-terminal aldehyde, chloromethylketone, or fluoromethylketone.

5. The composition of claim 1, wherein the isolated polypeptide is a modified polypeptide that has a terminal thiazole group.

6. The composition of claim 1, wherein the polypeptide has a dissociation constant (Ki) for inhibition of the cleavage of the mixed lineage leukemia (MLL) nuclear protein of SEQ ID NO: 59, by the Taspase1 of SEQ ID NO:1, of about $10^{-4}$ M or less.

7. The composition of claim 1, wherein the isolated polypeptide is a modified polypeptide that has a terminal pyridyl group.

8. The composition of claim 2, wherein the C-terminal or N-terminal end of the isolated polypeptide is a chemically reactive group that will form a covalent bond between the Taspase1 and the isolated polypeptide.

9. The composition of claim 8, wherein the chemically reactive group is a C-terminal aldehyde, chloromethylketone, or fluoromethylketone.

10. The composition of claim 2, wherein the isolated polypeptide is a modified polypeptide that has a terminal thiazole group.

11. The composition of claim 2, wherein the isolated polypeptide is a modified polypeptide that has a terminal pyridyl group.

12. The composition of claim 2, wherein the polypeptide has a Ki for inhibition of the cleavage of the MLL nuclear protein of SEQ ID NO: 59, by the Taspase1 of SEQ ID NO:1, of about $10^{-4}$ M or less.

13. A composition comprising an isolated polypeptide that inhibits the protease activity of the Taspase1 of SEQ ID NO: 1, wherein the isolated polypeptide consists of the amino acid sequence SQLA (SEQ ID NO:6) or a chemically modified variant of SEQ ID NO: 6.

14. The composition of claim 13, wherein the C-terminal or N-terminal end of the isolated polypeptide is a chemically reactive group that will form a covalent bond between the Taspase1 and the isolated polypeptide.

15. The composition of claim 14, wherein the chemically reactive group is a C-terminal aldehyde, chloromethylketone, or fluoromethylketone.

16. The composition of claim 13, wherein the isolated polypeptide is a modified polypeptide that has a terminal thiazole group.

17. The composition of claim 13, wherein the isolated polypeptide is a modified polypeptide that has a terminal pyridyl group.

18. The composition of claim 13, wherein the polypeptide has a Ki for inhibition of the cleavage of the MLL nuclear protein of SEQ ID NO: 59, by the Taspase1 of SEQ ID NO:1, of about $10^{-4}$ M or less.

19. A composition comprising an isolated polypeptide that inhibits the protease activity of the Taspase1 of SEQ ID NO: 1, wherein the isolated polypeptide consists of the amino acid sequence ISQLA (SEQ ID NO:7) or a chemically modified variant of SEQ ID NO: 7.

20. The composition of claim 19, wherein the C-terminal or N-terminal end of the isolated polypeptide is a chemically reactive group that will form a covalent bond between the Taspase1 and the isolated polypeptide.

21. The composition of claim 20, wherein the chemically reactive group is a C-terminal aldehyde, chloromethylketone, or fluoromethylketone.

22. The composition of claim 19, wherein the isolated polypeptide is a modified polypeptide that has a terminal thiazole group.

23. The composition of claim 19, wherein the isolated polypeptide is a modified polypeptide that has a terminal pyridyl group.

24. The composition of claim 19, wherein the polypeptide has a Ki for inhibition of the cleavage of the MLL nuclear protein of SEQ ID NO: 59, by the Taspase1 of SEQ ID NO:1, of about $10^{-4}$ M or less.

* * * * *

UNITED STATES PATENT AND TRADEMARK OFFICE
CERTIFICATE OF CORRECTION

| | | |
|---|---|---|
| PATENT NO. | : 7,964,700 B2 | Page 1 of 1 |
| APPLICATION NO. | : 11/851301 | |
| DATED | : June 21, 2011 | |
| INVENTOR(S) | : James J. D. Hsieh, Stanley Korsmeyer and Emily H. Y. Cheng | |

It is certified that error appears in the above-identified patent and that said Letters Patent is hereby corrected as shown below:

On the First Page, Column 1 Item 75 (Inventors), line 2-4, delete "Stanley J. Korsmeyer, Weston, MA (US); Susan Korsmeyer, legal representative, Weston, MA (US);" and insert -- Stanley J. Korsmeyer, Deceased, late of Weston, MA (US); by Susan Korsmeyer, legal representative, Weston, MA (US); --

Signed and Sealed this
Sixteenth Day of August, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,964,700 B2 | Page 1 of 1 |
| APPLICATION NO. | : 11/851301 | |
| DATED | : June 21, 2011 | |
| INVENTOR(S) | : Hsieh et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 95 days.

Signed and Sealed this
Fifteenth Day of November, 2011

David J. Kappos
*Director of the United States Patent and Trademark Office*

SEQUENCE LISTING

```
<160> NUMBER OF SEQ ID NOS: 59

<210> SEQ ID NO 1
<211> LENGTH: 420
<212> TYPE: PRT
<213> ORGANISM: Homo sapiens

<400> SEQUENCE: 1

Met Thr Met Glu Lys Gly Met Ser Ser Gly Glu Gly Leu Pro Ser Arg
 1               5                   10                  15
```

```
Ser Ser Gln Val Ser Ala Gly Lys Ile Thr Ala Lys Glu Leu Glu Thr
            20                  25                  30

Lys Gln Ser Tyr Lys Glu Lys Arg Gly Gly Phe Val Leu Val His Ala
            35                  40                  45

Gly Ala Gly Tyr His Ser Ser Lys Ala Lys Glu Tyr Lys His Val
 50                  55                  60

Cys Lys Arg Ala Cys Gln Lys Ala Ile Glu Lys Leu Gln Ala Gly Ala
 65                  70                  75                  80

Leu Ala Thr Asp Ala Val Thr Ala Ala Leu Val Glu Leu Glu Asp Ser
                 85                  90                  95

Pro Phe Thr Asn Ala Gly Met Gly Ser Asn Leu Asn Leu Leu Gly Glu
                100                 105                 110

Ile Glu Cys Asp Ala Ser Ile Met Asp Gly Lys Ser Leu Asn Phe Gly
                115                 120                 125

Ala Val Gly Ala Leu Ser Gly Ile Lys Asn Pro Val Ser Val Ala Asn
130                 135                 140

Arg Leu Leu Cys Glu Gly Gln Lys Gly Lys Leu Ser Ala Gly Arg Ile
145                 150                 155                 160

Pro Pro Cys Phe Leu Val Gly Glu Gly Ala Tyr Arg Trp Ala Val Asp
                165                 170                 175

His Gly Ile Pro Ser Cys Pro Pro Asn Ile Met Thr Thr Arg Phe Ser
                180                 185                 190

Leu Ala Ala Phe Lys Arg Asn Lys Arg Lys Leu Glu Leu Ala Glu Arg
                195                 200                 205

Val Asp Thr Asp Phe Met Gln Leu Lys Lys Arg Arg Gln Ser Ser Glu
    210                 215                 220

Lys Glu Asn Asp Ser Gly Thr Leu Asp Thr Val Gly Ala Val Val Val
225                 230                 235                 240

Asp His Glu Gly Asn Val Ala Ala Ala Val Ser Ser Gly Gly Leu Ala
                245                 250                 255

Leu Lys His Pro Gly Arg Val Gly Gln Ala Ala Leu Tyr Gly Cys Gly
                260                 265                 270

Cys Trp Ala Glu Asn Thr Gly Ala His Asn Pro Tyr Ser Thr Ala Val
                275                 280                 285

Ser Thr Ser Gly Cys Gly Glu His Leu Val Arg Thr Ile Leu Ala Arg
    290                 295                 300

Glu Cys Ser His Ala Leu Gln Ala Glu Asp Ala His Gln Ala Leu Leu
305                 310                 315                 320

Glu Thr Met Gln Asn Lys Phe Ile Ser Ser Pro Phe Leu Ala Ser Glu
                325                 330                 335

Asp Gly Val Leu Gly Gly Val Ile Val Leu Arg Ser Cys Arg Cys Ser
                340                 345                 350

Ala Glu Pro Asp Ser Ser Gln Asn Lys Gln Thr Leu Leu Val Glu Phe
                355                 360                 365

Leu Trp Ser His Thr Thr Glu Ser Met Cys Val Gly Tyr Met Ser Ala
    370                 375                 380

Gln Asp Gly Lys Ala Lys Thr His Ile Ser Arg Leu Pro Pro Gly Ala
385                 390                 395                 400

Val Ala Gly Gln Ser Val Ala Ile Glu Gly Gly Val Cys Arg Leu Glu
                405                 410                 415

Ser Pro Val Asn
            420
```

```
<210> SEQ ID NO 2
<211> LENGTH: 1263
<212> TYPE: DNA
<213> ORGANISM: Homo sapiens

<400> SEQUENCE: 2
atgaccatgg agaaggggat gagttctgga gaagggctgc cttccagatc atctcaggtt      60
tcggctggta aaataacagc caaagagttg gaaacaaagc agtcctataa agagaaacga     120
ggaggctttg tgttggtgca tgcaggtgca ggttatcatt ctgaatccaa agccaaggag     180
tataaacatg tatgcaaacg agcttgtcag aaggcaattg aaaagctgca ggccggtgct     240
cttgcaactg acgcagtcac tgcagcactg gtggaacttg aggattctcc ttttacaaat     300
gcaggaatgg gatctaatct aaatctgtta ggtgaaattg agtgtgatgc cagcataatg     360
gatggaaaat ccttaaattt tggagcagtt ggagcactga gtggaatcaa gaacccagtc     420
tcggttgcca acagactctt atgtgaaggg cagaagggca agctctcggc tggcagaatt     480 cctcccctgct tttagttgg agaaggagcc tacagatggg cagtagatca tggaataccc     540
tcttgccctc ctaacatcat gaccacaaga ttcagtttag ctgcatttaa agaaacaag     600 aggaaactag agctggcaga aagggtggac acagatttta tgcaactaaa gaaaagaaga     660
caatcaagtg agaaggaaaa tgactcaggc actttggaca cggtaggcgc tgtggttgtg     720
gaccacgaag ggaatgttgc tgctgctgtc tccagtggag gcttggcctt gaaacatccg     780
gggagagttg ggcaggctgc tctttatgga tgtggctgct gggctgaaaa tactggagct     840
cataacccct actccacagc tgtgagtacc tcaggatgtg gagagcatct tgtgcgcacc     900
atactggcta gagaatgttc acatgcttta caagctgagg atgctcacca gccctgttg     960 gagactatgc aaaacaagtt tatcagttca ccttttcctg ccagtgaaga tggcgtgctt    1020
ggcggagtga ttgtcctccg ttcatgcaga tgttctgccg agcctgactc ctcccaaaat    1080
aagcagacac ttctagtgga atttctgtgg agccacacga cggagagcat gtgtgtcgga    1140
tatatgtcag cccaggatgg gaaagccaag actcacattt caagacttcc tcctggtgcg    1200
gtggcaggac agtctgtggc aatcgaaggt ggggtgtgcc gcctggagag cccagtgaac    1260
tga                                                                  1263

<210> SEQ ID NO 3
<211> LENGTH: 5
<212> TYPE: PRT
<213> ORGANISM: Homo sapiens

<400> SEQUENCE: 3

Asp Gly Ala Asp Asp
 1               5

<210> SEQ ID NO 4
<211> LENGTH: 5
<212> TYPE: PRT
<213> ORGANISM: Homo sapiens

<400> SEQUENCE: 4

Asp Gly Val Asp Asp
 1               5

<210> SEQ ID NO 5
<211> LENGTH: 5
<212> TYPE: PRT
<213> ORGANISM: Homo sapiens

<400> SEQUENCE: 5
```

```
Leu Asp Thr Val Gly
 1               5

<210> SEQ ID NO 6
<211> LENGTH: 4
<212> TYPE: PRT
<213> ORGANISM: Homo sapiens

<400> SEQUENCE: 6

Ser Gln Leu Ala
 1

<210> SEQ ID NO 7
<211> LENGTH: 5
<212> TYPE: PRT
<213> ORGANISM: Homo sapiens

<400> SEQUENCE: 7

Ile Ser Gln Leu Ala
 1               5

<210> SEQ ID NO 8
<211> LENGTH: 6
<212> TYPE: PRT
<213> ORGANISM: Homo sapiens

<400> SEQUENCE: 8

Lys Ile Ser Gln Leu Ala
 1               5

<210> SEQ ID NO 9
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 9

Ser Gln Leu Asp
 1

<210> SEQ ID NO 10
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 10

Ile Ser Gln Leu Asp
 1               5

<210> SEQ ID NO 11
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 11

Lys Ile Ser Gln Leu Asp
 1               5

<210> SEQ ID NO 12
<211> LENGTH: 4
<212> TYPE: PRT
```

```
<213> ORGANISM: Artificial Sequence
<220> FEATURE:
<223> OTHER INFORMATION: Synthetically generated peptide

<400> SEQUENCE: 12

Ser Gln Leu Asp
 1

<210> SEQ ID NO 13
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 13

Ile Ser Gln Leu Asp
 1               5

<210> SEQ ID NO 14
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 14

Lys Ile Ser Gln Leu Asp
 1               5

<210> SEQ ID NO 15
<211> LENGTH: 5
<212> TYPE: PRT
<213> ORGANISM: Homo sapiens

<400> SEQUENCE: 15

Ile Ser Gln Leu Asp
 1               5

<210> SEQ ID NO 16
<211> LENGTH: 5
<212> TYPE: PRT
<213> ORGANISM: Homo sapiens

<400> SEQUENCE: 16

Glu Gly Gln Val Asp
 1               5

<210> SEQ ID NO 17
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 17

Ser Gln Leu Ala
 1

<210> SEQ ID NO 18
<211> LENGTH: 5
<212> TYPE: PRT
<213> ORGANISM: Homo sapiens

<400> SEQUENCE: 18

Ala Ala Ala Asp Asp
 1               5
```

```
<210> SEQ ID NO 19
<211> LENGTH: 20
<212> TYPE: PRT
<213> ORGANISM: Homo sapiens

<400> SEQUENCE: 19

Gly Lys Arg Ser Ala Glu Gly Gln Val Asp Gly Ala Asp Asp Leu Ser
 1               5                  10                  15
Thr Ser Asp Glu
            20

<210> SEQ ID NO 20
<211> LENGTH: 20
<212> TYPE: PRT
<213> ORGANISM: Mus musculus

<400> SEQUENCE: 20

Gly Lys Arg Ser Ala Glu Gly Gln Val Asp Gly Ala Asp Asp Leu Ser
 1               5                  10                  15
Thr Ser Asp Glu
            20

<210> SEQ ID NO 21
<211> LENGTH: 20
<212> TYPE: PRT
<213> ORGANISM: Danio Rerio

<400> SEQUENCE: 21

Arg Lys Lys Ser Ala Glu Gly Gln Val Asp Gly Ala Asp Asp Ile Ser
 1               5                  10                  15
Ser Thr Ser Ser
            20

<210> SEQ ID NO 22
<211> LENGTH: 20
<212> TYPE: PRT
<213> ORGANISM: Homo sapiens

<400> SEQUENCE: 22

Cys Asp Leu Pro Lys Ile Ser Gln Leu Asp Gly Val Asp Asp Gly Thr
 1               5                  10                  15
Glu Ser Asp Thr
            20

<210> SEQ ID NO 23
<211> LENGTH: 20
<212> TYPE: PRT
<213> ORGANISM: Mus musculus

<400> SEQUENCE: 23

Cys Asp Leu Pro Lys Ile Ser Gln Leu Asp Gly Val Asp Asp Gly Thr
 1               5                  10                  15
Glu Ser Asp Thr
            20

<210> SEQ ID NO 24
<211> LENGTH: 20
<212> TYPE: PRT
<213> ORGANISM: Danio rerio

<400> SEQUENCE: 24

Leu Gly Lys Pro Gln Ile Gly Gln Leu Asp Gly Val Asp Asp Gly Ser
```

-continued

```
                1               5                  10                  15
Glu Ser Asp Ala
            20

<210> SEQ ID NO 25
<211> LENGTH: 20
<212> TYPE: PRT
<213> ORGANISM: Anopheles trathorax

<400> SEQUENCE: 25

Phe Gln Lys Leu Lys Ile Ser Gln Leu Asp Gly Val Asp Asp Ile Cys
1               5                  10                  15

Leu Asp Gly Thr
            20

<210> SEQ ID NO 26
<211> LENGTH: 20
<212> TYPE: PRT
<213> ORGANISM: Drosophilia trithorax

<400> SEQUENCE: 26

Ala Ala Lys Met Arg Ile Met Gln Met Asp Gly Val Asp Asp Ser Ile
1               5                  10                  15

Thr Glu Phe Arg
            20

<210> SEQ ID NO 27
<211> LENGTH: 20
<212> TYPE: PRT
<213> ORGANISM: Homo sapiens

<400> SEQUENCE: 27

Pro Gly Ala Pro Arg Ile Glu Gln Leu Asp Gly Val Asp Asp Gly Thr
1               5                  10                  15

Asp Ser Glu Ala
            20

<210> SEQ ID NO 28
<211> LENGTH: 10
<212> TYPE: PRT
<213> ORGANISM: Homo sapiens

<400> SEQUENCE: 28

Thr Leu Asp Thr Val Gly Ala Val Val Val
1               5                  10

<210> SEQ ID NO 29
<211> LENGTH: 10
<212> TYPE: PRT
<213> ORGANISM: Mus musculus

<400> SEQUENCE: 29

Thr Leu Asp Thr Val Gly Ala Val Val Val
1               5                  10

<210> SEQ ID NO 30
<211> LENGTH: 10
<212> TYPE: PRT
<213> ORGANISM: Rattus norvegicus

<400> SEQUENCE: 30

Ala Leu Asp Thr Val Gly Ala Val Val Val
1               5                  10
```

```
<210> SEQ ID NO 31
<211> LENGTH: 10
<212> TYPE: PRT
<213> ORGANISM: Fugu rubripes

<400> SEQUENCE: 31

Cys Leu Asp Thr Val Gly Ala Val Val Val
1               5                   10

<210> SEQ ID NO 32
<211> LENGTH: 10
<212> TYPE: PRT
<213> ORGANISM: Danio rerio

<400> SEQUENCE: 32

Cys Leu Asp Thr Val Gly Ala Val Val Val
1               5                   10

<210> SEQ ID NO 33
<211> LENGTH: 10
<212> TYPE: PRT
<213> ORGANISM: Anopheles gambiae

<400> SEQUENCE: 33

Pro Leu Asp Thr Val Gly Ala Val Cys Val
1               5                   10

<210> SEQ ID NO 34
<211> LENGTH: 10
<212> TYPE: PRT
<213> ORGANISM: Drosophilia melanogaster

<400> SEQUENCE: 34

Ala Leu Asp Thr Val Gly Ala Val Cys Val
1               5                   10

<210> SEQ ID NO 35
<211> LENGTH: 10
<212> TYPE: PRT
<213> ORGANISM: Homo sapiens

<400> SEQUENCE: 35

Gly His Asp Thr Ile Gly Met Val Val Ile
1               5                   10

<210> SEQ ID NO 36
<211> LENGTH: 10
<212> TYPE: PRT
<213> ORGANISM: Mus musculus

<400> SEQUENCE: 36

Ser His Asp Thr Ile Gly Met Val Val Ile
1               5                   10

<210> SEQ ID NO 37
<211> LENGTH: 10
<212> TYPE: PRT
<213> ORGANISM: Fugu rubripes

<400> SEQUENCE: 37

Ala His Asp Thr Ile Gly Met Ile Ala Ile
1               5                   10

<210> SEQ ID NO 38
<211> LENGTH: 10
```

```
<212> TYPE: PRT
<213> ORGANISM: Spodotera frugiperda

<400> SEQUENCE: 38

Asn His Asp Thr Ile Gly Met Val Ala Ile
1               5                   10

<210> SEQ ID NO 39
<211> LENGTH: 10
<212> TYPE: PRT
<213> ORGANISM: Flavobacterium meningosepticum

<400> SEQUENCE: 39

Asn His Asp Thr Ile Gly Met Ile Ala Ile
1               5                   10

<210> SEQ ID NO 40
<211> LENGTH: 10
<212> TYPE: PRT
<213> ORGANISM: Homo sapiens

<400> SEQUENCE: 40

Asn Leu Gly Thr Val Gly Ala Val Ala Leu
1               5                   10

<210> SEQ ID NO 41
<211> LENGTH: 10
<212> TYPE: PRT
<213> ORGANISM: Mus musculus

<400> SEQUENCE: 41

Asn Ser Gly Thr Val Gly Ala Val Ala Leu
1               5                   10

<210> SEQ ID NO 42
<211> LENGTH: 10
<212> TYPE: PRT
<213> ORGANISM: Fugu rubripes

<400> SEQUENCE: 42

Lys Met Gly Thr Val Gly Ala Val Ala Val
1               5                   10

<210> SEQ ID NO 43
<211> LENGTH: 10
<212> TYPE: PRT
<213> ORGANISM: Arabidopsis thaliana

<400> SEQUENCE: 43

Gln Ile Gly Thr Val Gly Cys Val Ala Val
1               5                   10

<210> SEQ ID NO 44
<211> LENGTH: 10
<212> TYPE: PRT
<213> ORGANISM: Lupinus arboreus

<400> SEQUENCE: 44

Gln Ile Gly Thr Val Gly Cys Val Ala Val
1               5                   10

<210> SEQ ID NO 45
<211> LENGTH: 420
<212> TYPE: PRT
<213> ORGANISM: Mus musculus
```

-continued

<400> SEQUENCE: 45

| Met | Ile | Met | Glu | Lys | Gly | Met | Asn | Ser | Gly | Glu | Gly | Leu | Pro | Ser | Arg |
| 1 | | | | 5 | | | | | 10 | | | | | 15 | |

| Ser | Ser | Gln | Ala | Ser | Ala | Ala | Lys | Val | Thr | Val | Lys | Glu | Leu | Glu | Thr |
| | | | 20 | | | | | 25 | | | | | 30 | | |

| Gln | Gln | Pro | Cys | Lys | Glu | Lys | Arg | Gly | Gly | Phe | Val | Leu | Val | His | Ala |
| | | | 35 | | | | | 40 | | | | | 45 | | |

| Gly | Ala | Gly | Tyr | His | Ser | Glu | Ser | Lys | Ala | Lys | Glu | Tyr | Lys | His | Val |
| | | | 50 | | | | | 55 | | | | | 60 | | |

| Cys | Lys | Arg | Ala | Cys | Gln | Lys | Ala | Ile | Glu | Lys | Leu | Gln | Ala | Gly | Ala |
| 65 | | | | | 70 | | | | | 75 | | | | | 80 |

| Leu | Ala | Thr | Asp | Ala | Val | Ala | Ala | Leu | Val | Glu | Leu | Glu | Asp | Ser |
| | | | | 85 | | | | | 90 | | | | | 95 |

| Pro | Phe | Thr | Asn | Ala | Gly | Ile | Gly | Ser | Asn | Leu | Asn | Leu | Leu | Gly | Glu |
| | | | | 100 | | | | | 105 | | | | | 110 | |

| Ile | Glu | Cys | Asp | Ala | Ser | Ile | Met | Asp | Gly | Lys | Ser | Leu | Asn | Phe | Gly |
| | | | | 115 | | | | | 120 | | | | | 125 | |

| Ala | Val | Gly | Ala | Leu | Ser | Gly | Ile | Lys | Asn | Pro | Val | Ser | Val | Ala | His |
| | | | 130 | | | | | 135 | | | | | 140 | | |

| Arg | Leu | Leu | Cys | Glu | Gly | Gln | Lys | Gly | Lys | Leu | Ser | Ala | Gly | Arg | Ile |
| 145 | | | | | 150 | | | | | 155 | | | | | 160 |

| Pro | Pro | Cys | Phe | Leu | Val | Gly | Glu | Gly | Ala | Tyr | Arg | Trp | Ala | Val | Asp |
| | | | | 165 | | | | | 170 | | | | | 175 | |

| His | Gly | Ile | Pro | Ser | Cys | Pro | Pro | Ser | Thr | Met | Thr | Thr | Arg | Phe | Ser |
| | | | 180 | | | | | 185 | | | | | 190 | | |

| Leu | Ala | Ala | Phe | Lys | Arg | Asn | Lys | Arg | Lys | Leu | Glu | Leu | Ala | Glu | Arg |
| | | | 195 | | | | | 200 | | | | | 205 | | |

| Val | Glu | Thr | Asp | Phe | Ile | Gln | Leu | Lys | Arg | Arg | Arg | Gln | Ser | Ser | Ala |
| | | 210 | | | | | 215 | | | | | 220 | | | |

| Lys | Glu | Asn | Asp | Ser | Gly | Thr | Leu | Asp | Thr | Val | Gly | Ala | Val | Val | Val |
| 225 | | | | | 230 | | | | | 235 | | | | | 240 |

| Asp | His | Glu | Gly | Asn | Val | Ala | Ala | Val | Ser | Ser | Gly | Gly | Leu | Ala |
| | | | | 245 | | | | | 250 | | | | | 255 |

| Leu | Lys | His | Pro | Gly | Arg | Val | Gly | Gln | Ala | Ala | Leu | Tyr | Gly | Cys | Gly |
| | | | 260 | | | | | 265 | | | | | 270 | | |

| Cys | Trp | Ala | Glu | Asn | Thr | Gly | Ala | Gln | Asn | Pro | Tyr | Ser | Thr | Ala | Val |
| | | | 275 | | | | | 280 | | | | | 285 | | |

| Ser | Thr | Ser | Gly | Cys | Gly | Glu | His | Leu | Val | Arg | Thr | Ile | Leu | Ala | Arg |
| | | 290 | | | | | 295 | | | | | 300 | | | |

| Glu | Cys | Ser | His | Ala | Leu | Gln | Ala | Glu | Asp | Ala | His | Gln | Ala | Leu | Leu |
| 305 | | | | | 310 | | | | | 315 | | | | | 320 |

| Glu | Thr | Met | Gln | Asn | Lys | Phe | Ile | Ser | Ser | Pro | Phe | Leu | Ala | Cys | Glu |
| | | | | 325 | | | | | 330 | | | | | 335 |

| Asp | Gly | Val | Leu | Gly | Gly | Val | Ile | Val | Leu | Arg | Ser | Cys | Arg | Cys | Ser |
| | | | 340 | | | | | 345 | | | | | 350 | | |

| Ser | Glu | Ser | Asp | Ser | Ser | Gln | Asp | Lys | Gln | Thr | Leu | Leu | Val | Glu | Phe |
| | | | 355 | | | | | 360 | | | | | 365 | | |

| Leu | Trp | Ser | His | Thr | Thr | Glu | Ser | Met | Cys | Val | Gly | Tyr | Met | Ser | Ala |
| | | 370 | | | | | 375 | | | | | 380 | | | |

| Gln | Asp | Gly | Lys | Ala | Lys | Thr | His | Ile | Ser | Arg | Leu | Pro | Pro | Gly | Ala |
| 385 | | | | | 390 | | | | | 395 | | | | | 400 |

| Val | Ala | Gly | Gln | Ser | Val | Ala | Ile | Glu | Gly | Gly | Val | Cys | Arg | Leu | Glu |
| | | | | 405 | | | | | 410 | | | | | 415 |

-continued

Ser Pro Val Asn
        420

<210> SEQ ID NO 46
<211> LENGTH: 386
<212> TYPE: PRT
<213> ORGANISM: Rattus norvegicus

<400> SEQUENCE: 46

Met Leu Lys Phe Val Asp Asp Ser Glu Tyr Arg Asp Ser Pro Phe Thr
 1               5                  10                  15

Asn Ala Gly Val Gly Ser Asn Leu Asn Leu Leu Gly Glu Ile Glu Cys
            20                  25                  30

Asp Ala Ser Ile Met Asp Gly Lys Ser Leu Ser Phe Gly Ala Val Gly
        35                  40                  45

Ala Leu Ser Gly Ile Lys Asn Pro Val Ser Val Ala His Arg Leu Leu
    50                  55                  60

Cys Glu Gly Gln Lys Gly Lys Leu Ser Ala Gly Arg Ile Pro Pro Cys
65                  70                  75                  80

Phe Leu Val Gly Glu Gly Ala Tyr Arg Trp Ala Val Asp His Gly Ile
                85                  90                  95

Pro Ser Cys Pro Pro Ser Thr Met Thr Thr Arg Phe Ser Leu Ala Ala
            100                 105                 110

Phe Lys Arg Asn Lys Arg Lys Leu Glu Leu Ala Glu Val Glu Thr
        115                 120                 125

Asp Phe Ile Gln Leu Lys Arg Arg Arg Gln Ser Ser Ala Lys Glu Asn
    130                 135                 140

Asp Ser Gly Ala Leu Asp Thr Val Gly Ala Val Val Asp His Glu
145                 150                 155                 160

Gly Asn Val Ala Ala Val Ser Ser Gly Gly Leu Ala Leu Lys His
                165                 170                 175

Pro Gly Arg Val Gly Gln Asp Val Glu Ser Ile Leu Cys Ala Pro Tyr
            180                 185                 190

Trp Leu Glu Asn Val His Thr Leu Tyr Lys Leu Lys Thr Leu Thr Lys
        195                 200                 205

Leu Cys Trp Arg Leu Cys Lys Thr Ser Leu Ser Asp Thr Glu Arg Ile
    210                 215                 220

Pro Gly Leu Asp Ser Ala Tyr Gly Thr Gly Lys Lys Arg Glu Gly Ile
225                 230                 235                 240

Pro Ser Leu Gly Ser Glu Lys Glu Phe His Asn Gly Gln Pro His Asp
                245                 250                 255

Ala Trp Asn Ser Asp Thr His Leu His Ser Thr Ala Arg Thr Leu His
            260                 265                 270

His Gly Ser Pro Phe Leu Ala Ser Glu Asp Gly Val Leu Gly Gly Val
        275                 280                 285

Ile Val Leu Arg Ser Cys Arg Cys Pro Ser Glu Ser Asp Pro Ser Gln
    290                 295                 300

Asp Lys Gln Thr Leu Leu Val Glu Phe Leu Trp Ser His Ser Thr Glu
305                 310                 315                 320

Ser Met Cys Val Gly Tyr Met Ser Ala Gln Asp Gly Lys Ala Lys Val
                325                 330                 335

Ile Val Arg Asn Met Thr Leu Glu Ser Leu Leu His Phe Ser Lys Val
            340                 345                 350

Phe Asn Ala Val Ile Ile Tyr Leu Trp Pro Leu Phe Leu Asn Val Ile
        355                 360                 365

```
Asp Asp Val Ile Cys Glu Val Ser Leu Asn Asp Leu Ile Leu Pro
    370                 375                 380
Cys Tyr
385

<210> SEQ ID NO 47
<211> LENGTH: 360
<212> TYPE: PRT
<213> ORGANISM: Danio rerio

<400> SEQUENCE: 47

Lys Glu Glu Ser Ser Lys Asn Gln Lys Ala Lys Pro Val Gly Gly Phe
  1               5                  10                  15

Val Leu Val His Ala Gly Ala Gly Tyr His Ser Glu Ser Lys Ala Lys
             20                  25                  30

Glu Tyr Lys His Val Cys Lys Arg Ala Cys Gln Arg Ala Val Asp Gln
         35                  40                  45

Leu Asn Ala Gly Ala Leu Ala Val Glu Ala Val Ala Ala Ala Leu Val
 50                  55                  60

Glu Leu Glu Asp Ser Pro Phe Thr Asn Ala Gly Met Gly Ser Asn Leu
65                  70                  75                  80

Asn Leu Leu Gly Glu Ile Glu Cys Asp Ala Ser Ile Met Asp Gly Lys
                 85                  90                  95

Ser Leu Gln Tyr Gly Ala Val Gly Ser Ile Ser Gly Val Lys Asn Pro
            100                 105                 110

Val Leu Val Ala Asn Arg Leu Leu Ser Glu Ala Gln Arg Gly Lys Leu
        115                 120                 125

Ser Ala Gly Arg Ile Pro Pro Cys Phe Leu Val Gly Arg Gly Ala Leu
130                 135                 140

Glu Trp Ala Val Ser His Gly Ile Ala Pro Cys Pro Ser Glu Lys Met
145                 150                 155                 160

Ala Thr Lys Phe Ser Leu Ser Ala Tyr Lys Arg Asn Leu Arg Lys Met
                165                 170                 175

Glu Leu Ala Glu Leu Ala Glu Lys Met Glu Ser Gly His Asn Gln Ile
            180                 185                 190

Lys Lys Arg Arg Gln Ser Thr Glu Thr Ala Asn Pro Thr Glu Asp Gly
        195                 200                 205

Ser Gly Cys Leu Asp Thr Val Gly Ala Val Val Asp Leu Glu Gly
210                 215                 220

Asn Val Ala Ala Ala Val Ser Ser Gly Gly Leu Ala Met Lys His Pro
225                 230                 235                 240

Gly Arg Val Gly Gln Val Gly Leu Ser Gln Tyr Asn Asn Ala His Phe
                245                 250                 255

Cys Val Thr Ala Ser Phe Cys Cys Gly Glu His Leu Ile Arg Thr Met
            260                 265                 270

Leu Ala Arg Glu Cys Ser Ala Ala Met Arg Ser Glu Asp Ala His Gln
        275                 280                 285

Ala Leu Leu Glu Ala Met Gln Asn Lys Phe Ile Ser Ser Pro Phe Leu
290                 295                 300

Ala Gly Glu Asp Arg Val Leu Gly Gly Val Ile Val Leu Arg Gly Cys
305                 310                 315                 320

Arg Cys Val Glu Ala Pro Ser Ser Gln Asn Ile Gln Gly Ile Leu Val
                325                 330                 335

Glu Phe Leu Trp Ser His Thr Thr Glu Ser Met Cys Val Gly Tyr Met
            340                 345                 350
```

Ser Ala Gln Asp Ser Lys Ala Lys
          355                 360

<210> SEQ ID NO 48
<211> LENGTH: 328
<212> TYPE: PRT
<213> ORGANISM: Danio rerio

<400> SEQUENCE: 48

Lys Leu Asn Ser Thr Ile Ser His Arg Asp Gly Lys Asn Met Gly Phe
 1               5                  10                  15

Val Leu Val His Ala Gly Ala Gly Tyr His Ser Glu Ser Lys Ala Lys
             20                  25                  30

Glu Tyr Lys His Val Cys Lys Arg Ala Cys Gln Lys Leu Gln Asp Ser
         35                  40                  45

Pro Phe Thr Asn Ala Gly Thr Gly Ser Asn Leu Asn Leu Ser Gly Glu
     50                  55                  60

Val Glu Cys Asp Ala Ser Ile Met Asp Gly Lys Ser Leu Asn Tyr Gly
 65                  70                  75                  80

Ala Val Gly Ala Leu Ser Gly Ile Lys Asn Pro Val Leu Val Ser Arg
                 85                  90                  95

Arg Leu Leu Ser Glu Thr Gln Lys Gly Lys Leu Ser Ala Gly Arg Ile
            100                 105                 110

Pro Pro Phe Leu Val Gly Lys Gly Ala Glu Gln Trp Ala Ile Ser His
        115                 120                 125

Gly Ile Pro Ala Cys Pro Thr Glu Lys Met Thr Thr Glu Gly Asn Asn
    130                 135                 140

Ser Ala Cys Leu Asp Thr Val Gly Ala Val Val Asp Gly Glu Gly
145                 150                 155                 160

Asn Val Ala Thr Ala Val Ser Ser Gly Gly Leu Ala Met Lys His Pro
                165                 170                 175

Gly Arg Val Gly Gln Ala Ala His Tyr Gly Cys Gly Cys Trp Ala Glu
            180                 185                 190

Asn Ala Arg Asp Val Ser Leu Tyr Ser Thr Ala Val Ser Gly Ser Gly
        195                 200                 205

Glu His Leu Ile Pro Pro Met Leu Ala Arg Glu Cys Ser Thr Ala Met
    210                 215                 220

His Ala Glu Asn Pro Pro Ala Pro Leu Glu Pro Met Gln Asn Lys
225                 230                 235                 240

Phe Ile Ser Ser Pro Phe Leu Ala Gly Glu Asp Cys Val Leu Gly Gly
                245                 250                 255

Val Ile Val Leu Arg Cys Cys Thr Cys Gly Glu Ala Gln Arg Ser Glu
            260                 265                 270

Asp Ile Gln Ala Leu Leu Val Glu Phe Leu Trp Ser His Thr Thr Glu
        275                 280                 285

Ser Met Cys Val Gly Tyr Met Ser Ala Gln Asp Ser Lys Ala Arg Thr
    290                 295                 300

His Ile Ser Arg Leu Pro Pro Gly Ala Val Ala Gly Gln Ser Leu Ala
305                 310                 315                 320

Ile Glu Gly Gly Val Cys Arg Leu
                325

<210> SEQ ID NO 49
<211> LENGTH: 388
<212> TYPE: PRT
<213> ORGANISM: Anopheles gambiae str -continued

<400> SEQUENCE: 49

Asn Ile Leu Pro Ser Gln Cys Ala Val Leu Lys Ser Ile Gln Leu Pro
1               5                   10                  15

Ser Thr Ser Cys Leu Cys Gln Cys Ser Cys Cys Pro Asn Val Ile Val
            20                  25                  30

Arg Lys Lys Ala Arg Ala Leu Val Thr Met Thr Gly Phe Val Ala Val
        35                  40                  45

His Thr Gly Ala Gly Asn Phe Leu Asp Glu Thr Leu Tyr Glu His Val
    50                  55                  60

Cys Arg Glu Ala Cys Asn Gln Ala Val Asn Val Leu Tyr Ala Gly Gly
65                  70                  75                  80

Thr Ala Leu Asp Ala Cys Glu Arg Ala Ile Val Leu Leu Glu Asn Ser
                85                  90                  95

Thr Ala Thr Asn Ala Gly Ile Gly Ser Asn Leu Asn Trp Asp Arg Arg
            100                 105                 110

Val Glu Cys Asp Ala Cys Ile Met Asp Gly Ala Ser Leu Gln Phe Gly
        115                 120                 125

Ala Cys Thr Asn Val Thr Asp Val Lys Asn Pro Ile Ser Leu Ala Arg
130                 135                 140

His Leu Cys Glu Arg Gln Ser Lys Leu Leu Ser Phe Gly Arg Ile Phe
145                 150                 155                 160

Phe Met Val Leu Val Gly Gln Gly Ala Ser Ala Tyr Ala Arg Glu Val
                165                 170                 175

Gly Leu Gln Leu Val Pro Ala Glu His Met Ile Ser Val Asn Ala Ala
            180                 185                 190

Lys Lys Tyr Asp His Tyr Arg Ser Gln Ile Met Gln Tyr Glu Glu Met
        195                 200                 205

Asn Arg Ala Lys Leu Ser Pro Leu Asp Thr Val Gly Ala Val Cys Val
210                 215                 220

Asp Ala Glu Gly Ser Ile Val Ala Gly Cys Ser Ser Gly Gly Met Leu
225                 230                 235                 240

Lys Leu Ser Gly Arg Val Gly Gln Ala Ala Thr Tyr Gly Ala Gly Cys
                245                 250                 255

Trp Ala Leu Met Asp Glu Ser Thr Ser Met Ser Ala Ala Ser Cys Thr
            260                 265                 270

Thr Gly Asn Gly Glu Tyr Leu Met Lys Thr Leu Phe Ala Lys Glu Leu
        275                 280                 285

Val Asp Asp Leu Ile Ser Cys Asn Cys Pro Ile Thr Ser Gln His Leu
290                 295                 300

Thr Tyr Lys Lys Lys Leu Leu Glu Ser Pro Phe Leu Ser Lys Gln Lys
305                 310                 315                 320

Ala Ile His Ala Gly Ser Leu Ser Ile Ile Tyr Asn Thr Ala Ser Gly
                325                 330                 335

Asp Gly Asp Leu Leu Trp Ala His Thr Thr Asn Ser Met Cys Ile Gly
            340                 345                 350

Phe Met Ser Thr Lys Gln Lys Lys Pro Lys Phe Val Leu Ser Lys Leu
        355                 360                 365

Pro Gln Asn Leu Thr Cys Gly Thr Lys Pro Val Ile Asn Gly His His
370                 375                 380

Phe Lys Leu Ile
385

<210> SEQ ID NO 50
<211> LENGTH: 360

-continued

```
<212> TYPE: PRT
<213> ORGANISM: Drosophila melanogaster

<400> SEQUENCE: 50

Met Ala Gly Phe Val Ala Val His Thr Gly Ala Gly Asn Cys Ile Asp
 1               5                  10                  15

Glu Thr Lys Tyr Gln Arg Val Ile Lys Glu Ala Cys Leu Arg Ala Thr
             20                  25                  30

Glu Ile Leu Arg Asn Gly Gly Ser Ala Val Asp Ala Cys Glu Ala Ala
         35                  40                  45

Ile Val Arg Leu Glu Asn Cys Gly Tyr Thr Asn Ala Gly Tyr Gly Ser
 50                  55                  60

Asn Leu Cys Met Asp Gly Ser Val Gln Cys Asp Ala Ala Ile Met Asp
65                  70                  75                  80

Gly Ser Thr Leu Asn Phe Gly Ala Cys Thr Asn Val Ser Arg Val Lys
                 85                  90                  95

Asn Pro Ile Gln Leu Ala Arg Arg Ile Cys Asp Ala Gln Ser Ser Pro
            100                 105                 110

Gln Leu Leu Glu Arg Ile Pro Pro Met Ile Leu Ala Gly Thr Gly Ala
        115                 120                 125

Glu His Tyr Ala Asp Glu Val Gly Cys Ser Met Val Glu Pro Gly Val
    130                 135                 140

Leu Ile Ser Ser Lys Ala Lys Phe Gln Phe Asn His Tyr Lys Ser Lys
145                 150                 155                 160

Tyr Asp Leu Val Val Asn Ser Arg Leu Gly Lys Ala Thr Ser Glu Glu
                165                 170                 175

Ser Val Gln Val Pro Glu Pro Gly Asn Glu Val Glu Leu Ala Ala Ala
            180                 185                 190

Leu Asp Thr Val Gly Ala Val Cys Val Asp Gly Ala Gly Asn Thr Ala
        195                 200                 205

Ala Gly Cys Ser Ser Gly Gly Ile Leu Leu Lys Val Pro Gly Arg Val
    210                 215                 220

Gly Gln Ala Ala Thr Tyr Gly Ala Gly Cys Trp Ala Thr Asp Thr Asp
225                 230                 235                 240

Glu Leu Ala Ile Ala Thr Cys Thr Thr Gly Asn Gly Glu Tyr Leu Met
                245                 250                 255

Lys Thr Leu Leu Ala Arg Glu Ile Cys His Gly Ala Phe Ser Ser Asp
            260                 265                 270

Cys Ala Val Thr Ser Leu His Lys Thr Phe Lys Gln Lys Phe Leu Asp
        275                 280                 285

Ser Pro Leu Leu Pro Arg Gln Gln Asp Leu Tyr Ala Gly Ala Leu Thr
    290                 295                 300

Leu Leu Tyr Tyr Pro Gly Gln Ser Ser Gly Glu Val Met Trp Ser His
305                 310                 315                 320

Thr Thr Gln Ser Phe Cys Val Gly Tyr Met Ala Thr Asn Gln Arg Val
                325                 330                 335

Pro Lys Phe Val His Ser Pro Leu Pro Thr Tyr Ser Val Pro Gly Arg
            340                 345                 350

Ser Cys Val Val Asn Gly His Asn
        355                 360

<210> SEQ ID NO 51
<211> LENGTH: 11
<212> TYPE: PRT
<213> ORGANISM: Homo sapiens
<220> FEATURE:
```

```
<221> NAME/KEY: VARIANT
<222> LOCATION: 7
<223> OTHER INFORMATION: Xaa = Asp or Gly

<400> SEQUENCE: 51

Pro Lys Ile Ser Gln Leu Xaa Val Asp Asp Gly
 1               5                  10

<210> SEQ ID NO 52
<211> LENGTH: 4
<212> TYPE: PRT
<213> ORGANISM: Homo sapiens

<400> SEQUENCE: 52

Ser Gln Leu Asp
 1

<210> SEQ ID NO 53
<211> LENGTH: 6
<212> TYPE: PRT
<213> ORGANISM: Homo sapiens

<400> SEQUENCE: 53

Lys Ile Ser Gln Leu Asp
 1               5

<210> SEQ ID NO 54
<211> LENGTH: 7
<212> TYPE: PRT
<213> ORGANISM: Homo sapiens

<400> SEQUENCE: 54

Lys Ile Ser Asp Gln Leu Ala
 1               5

<210> SEQ ID NO 55
<211> LENGTH: 5
<212> TYPE: PRT
<213> ORGANISM: Homo sapiens

<400> SEQUENCE: 55

Lys Ile Ser Gln Ala
 1               5

<210> SEQ ID NO 56
<211> LENGTH: 19
<212> TYPE: RNA
<213> ORGANISM: Artificial Sequence
<220> FEATURE:
<223> OTHER INFORMATION: Primer

<400> SEQUENCE: 56
gacucacauu ucaagacuu                                                19

<210> SEQ ID NO 57
<211> LENGTH: 19
<212> TYPE: RNA
<213> ORGANISM: Artificial Sequence
<220> FEATURE:
<223> OTHER INFORMATION: Primer

<400> SEQUENCE: 57
gaagucagag ugcgaaguc                                                19

<210> SEQ ID NO 58
<211> LENGTH: 5
```

```
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2, 5
<223> OTHER INFORMATION: Xaa = any amino acid

<400> SEQUENCE: 58

Ile Xaa Gln Leu Xaa
 1               5

<210> SEQ ID NO 59
<211> LENGTH: 3969
<212> TYPE: PRT
<213> ORGANISM: Homo sapiens
<220> FEATURE:
<221> NAME/KEY: VARIANT
<222> LOCATION: 30
<223> OTHER INFORMATION: Xaa = any amino acid

<400> SEQUENCE: 59

Met Ala His Ser Cys Arg Trp Arg Phe Pro Ala Arg Pro Gly Thr Thr
 1               5                  10                  15

Gly Gly Gly Gly Gly Gly Arg Arg Gly Leu Gly Gly Xaa Pro Arg
            20                  25                  30

Gln Arg Val Pro Ala Leu Leu Leu Pro Pro Gly Pro Pro Val Gly Gly
        35                  40                  45

Gly Gly Pro Gly Ala Pro Pro Ser Pro Pro Ala Val Ala Ala Ala
    50                  55                  60

Ala Ala Ala Gly Ser Ser Gly Ala Gly Val Pro Gly Gly Ala Ala Ala
65                  70                  75                  80

Ala Ser Ala Ala Ser Ser Ser Ala Ser Ser Ser Ser Ser Ser
                85                  90                  95

Ser Ser Ala Ser Ser Gly Pro Ala Leu Leu Arg Val Gly Pro Gly Phe
            100                 105                 110

Asp Ala Ala Leu Gln Val Ser Ala Ala Ile Gly Thr Asn Leu Arg Arg
        115                 120                 125

Phe Arg Ala Val Phe Gly Glu Ser Gly Gly Gly Gly Ser Gly Glu
    130                 135                 140

Asp Glu Gln Phe Leu Gly Phe Gly Ser Asp Glu Glu Val Arg Val Arg
145                 150                 155                 160

Ser Pro Thr Arg Ser Pro Ser Val Lys Thr Ser Pro Arg Lys Pro Arg
                165                 170                 175

Gly Arg Pro Arg Ser Gly Ser Asp Arg Asn Ser Ala Ile Leu Ser Asp
            180                 185                 190

Pro Ser Val Phe Ser Pro Leu Asn Lys Ser Glu Thr Lys Ser Gly Asp
        195                 200                 205

Lys Ile Lys Lys Lys Asp Ser Lys Ser Ile Glu Lys Lys Arg Gly Arg
    210                 215                 220

Pro Pro Thr Phe Pro Gly Val Lys Ile Lys Ile Thr His Gly Lys Asp
225                 230                 235                 240

Ile Ser Glu Leu Pro Lys Gly Asn Lys Glu Asp Ser Leu Lys Lys Ile
                245                 250                 255

Lys Arg Thr Pro Ser Ala Thr Phe Gln Gln Ala Thr Lys Ile Lys Lys
            260                 265                 270

Leu Arg Ala Gly Lys Leu Ser Pro Leu Lys Ser Lys Phe Lys Thr Gly
        275                 280                 285
```

```
Lys Leu Gln Ile Gly Arg Lys Gly Val Gln Ile Val Arg Arg Gly
    290                 295                 300

Arg Pro Pro Ser Thr Glu Arg Ile Lys Thr Pro Ser Val Ser Leu
305                 310                 315                 320

Ile Leu Asn Trp Lys Ser Pro Arg Lys Ser Gly Lys Thr Arg Lys Glu
                325                 330                 335

His Leu His Leu Gln Lys Lys Ile Arg Gln Leu Ser Asp Lys Ala Leu
            340                 345                 350

Glu Gly Leu Ser Gln Leu Gly Leu Phe Leu Leu Gln Lys Gly Gln Met
        355                 360                 365

Gln Pro Leu Leu Ser Asn Ser Tyr Arg Gly Gln Lys Lys Gly Ala Gln
    370                 375                 380

Lys Lys Ile Glu Lys Glu Ala Ala Gln Leu Gln Gly Arg Lys Val Lys
385                 390                 395                 400

Thr Gln Val Lys Asn Ile Arg Gln Phe Ile Met Pro Val Val Ser Ala
                405                 410                 415

Ile Ser Ser Arg Ile Ile Lys Thr Pro Arg Arg Phe Ile Glu Asp Glu
            420                 425                 430

Asp Tyr Asp Pro Pro Ile Lys Ile Ala Arg Leu Glu Ser Thr Pro Asn
        435                 440                 445

Ser Arg Phe Ser Ala Pro Ser Cys Gly Ser Ser Glu Lys Ser Ser Ala
    450                 455                 460

Ala Ser Gln His Ser Ser Gln Met Ser Ser Asp Ser Ser Arg Ser Ser
465                 470                 475                 480

Ser Pro Ser Val Asp Thr Ser Thr Asp Ser Gln Ala Ser Glu Glu Ile
                485                 490                 495

Gln Val Leu Pro Glu Glu Arg Ser Asp Thr Pro Glu Val His Pro Pro
            500                 505                 510

Leu Pro Ile Ser Gln Ser Pro Glu Asn Glu Ser Asn Asp Arg Arg Ser
        515                 520                 525

Arg Arg Tyr Ser Val Ser Glu Arg Ser Phe Gly Ser Arg Thr Thr Lys
    530                 535                 540

Lys Leu Ser Thr Leu Gln Ser Ala Pro Gln Gln Gln Thr Ser Ser Ser
545                 550                 555                 560

Pro Pro Pro Pro Leu Leu Thr Pro Pro Pro Leu Gln Pro Ala Ser
                565                 570                 575

Ser Ile Ser Asp His Thr Pro Trp Leu Met Pro Pro Thr Ile Pro Leu
            580                 585                 590

Ala Ser Pro Phe Leu Pro Ala Ser Thr Ala Pro Met Gln Gly Lys Arg
        595                 600                 605

Lys Ser Ile Leu Arg Glu Pro Thr Phe Arg Trp Thr Ser Leu Lys His
    610                 615                 620

Ser Arg Ser Glu Pro Gln Tyr Phe Ser Ser Ala Lys Tyr Ala Lys Glu
625                 630                 635                 640

Gly Leu Ile Arg Lys Pro Ile Phe Asp Asn Phe Arg Pro Pro Pro Leu
                645                 650                 655

Thr Pro Glu Asp Val Gly Phe Ala Ser Gly Phe Ser Ala Ser Gly Thr
            660                 665                 670

Ala Ala Ser Ala Arg Leu Phe Ser Pro Leu His Ser Gly Thr Arg Phe
        675                 680                 685

Asp Met His Lys Arg Ser Pro Leu Leu Arg Ala Pro Arg Phe Thr Pro
    690                 695                 700

Ser Glu Ala His Ser Arg Ile Phe Glu Ser Val Thr Leu Pro Ser Asn
705                 710                 715                 720
```

```
Arg Thr Ser Ala Gly Thr Ser Ser Gly Val Ser Asn Arg Lys Arg
            725                 730                 735

Lys Arg Lys Val Phe Ser Pro Ile Arg Ser Glu Pro Arg Ser Pro Ser
            740                 745                 750

His Ser Met Arg Thr Arg Ser Gly Arg Leu Ser Ser Ser Glu Leu Ser
            755                 760                 765

Pro Leu Thr Pro Pro Ser Ser Val Ser Ser Ser Leu Ser Ile Ser Val
            770                 775                 780

Ser Pro Leu Ala Thr Ser Ala Leu Asn Pro Thr Phe Thr Phe Pro Ser
785                 790                 795                 800

His Ser Leu Thr Gln Ser Gly Glu Ser Ala Glu Lys Asn Gln Arg Pro
            805                 810                 815

Arg Lys Gln Thr Ser Ala Pro Ala Glu Pro Phe Ser Ser Ser Pro
            820                 825                 830

Thr Pro Leu Phe Pro Trp Phe Thr Pro Gly Ser Gln Thr Glu Arg Gly
            835                 840                 845

Arg Asn Lys Asp Lys Ala Pro Glu Glu Leu Ser Lys Asp Arg Asp Ala
            850                 855                 860

Asp Lys Ser Val Glu Lys Asp Lys Ser Arg Glu Arg Asp Arg Glu Arg
865                 870                 875                 880

Glu Lys Glu Asn Lys Arg Glu Ser Arg Lys Glu Arg Lys Lys Gly
            885                 890                 895

Ser Glu Ile Gln Ser Ser Ser Ala Leu Tyr Pro Val Gly Arg Val Ser
            900                 905                 910

Lys Glu Lys Val Val Gly Glu Asp Val Ala Thr Ser Ser Ala Lys
            915                 920                 925

Lys Ala Thr Gly Arg Lys Lys Ser Ser Ser His Asp Ser Gly Thr Asp
            930                 935                 940

Ile Thr Ser Val Thr Leu Gly Asp Thr Thr Ala Val Lys Thr Lys Ile
945                 950                 955                 960

Leu Ile Lys Lys Gly Arg Gly Asn Leu Glu Lys Thr Asn Leu Asp Leu
            965                 970                 975

Gly Pro Thr Ala Pro Ser Leu Glu Lys Glu Lys Thr Leu Cys Leu Ser
            980                 985                 990

Thr Pro Ser Ser Ser Thr Val Lys His Ser Thr Ser Ser Ile Gly Ser
            995                 1000                1005

Met Leu Ala Gln Ala Asp Lys Leu Pro Met Thr Asp Lys Arg Val Ala
            1010                1015                1020

Ser Leu Leu Lys Lys Ala Lys Ala Gln Leu Cys Lys Ile Glu Lys Ser
1025                1030                1035                1040

Lys Ser Leu Lys Gln Thr Asp Gln Pro Lys Ala Gln Gly Gln Glu Ser
            1045                1050                1055

Asp Ser Ser Glu Thr Ser Val Arg Gly Pro Arg Ile Lys His Val Cys
            1060                1065                1070

Arg Arg Ala Ala Val Ala Leu Gly Arg Lys Arg Ala Val Phe Pro Asp
            1075                1080                1085

Asp Met Pro Thr Leu Ser Ala Leu Pro Trp Glu Glu Arg Glu Lys Ile
            1090                1095                1100

Leu Ser Ser Met Gly Asn Asp Asp Lys Ser Ser Ile Ala Gly Ser Glu
1105                1110                1115                1120

Asp Ala Glu Pro Leu Ala Pro Pro Ile Lys Pro Ile Lys Pro Val Thr
            1125                1130                1135

Arg Asn Lys Ala Pro Gln Glu Pro Pro Val Lys Lys Gly Arg Arg Ser
```

-continued

```
                    1140                1145                1150
Arg Arg Cys Gly Gln Cys Pro Gly Cys Gln Val Pro Glu Asp Cys Gly
                1155                1160                1165
Val Cys Thr Asn Cys Leu Asp Lys Pro Lys Phe Gly Gly Arg Asn Ile
1170                1175                1180
Lys Lys Gln Cys Cys Lys Met Arg Lys Cys Gln Asn Leu Gln Trp Met
1185                1190                1195                1200
Pro Ser Lys Ala Tyr Leu Gln Lys Gln Ala Lys Ala Val Lys Lys
                1205                1210                1215
Glu Lys Lys Ser Lys Thr Ser Glu Lys Lys Asp Ser Lys Glu Ser Ser
                1220                1225                1230
Val Val Lys Asn Val Val Asp Ser Ser Gln Lys Pro Thr Pro Ser Ala
                1235                1240                1245
Arg Glu Asp Pro Ala Pro Lys Lys Ser Ser Ser Glu Pro Pro Pro Arg
                1250                1255                1260
Lys Pro Val Glu Glu Lys Ser Glu Glu Gly Asn Val Ser Ala Pro Gly
1265                1270                1275                1280
Pro Glu Ser Lys Gln Ala Thr Thr Pro Ala Ser Arg Lys Ser Ser Lys
                1285                1290                1295
Gln Val Ser Gln Pro Ala Leu Val Ile Pro Pro Gln Pro Pro Thr Thr
                1300                1305                1310
Gly Pro Pro Arg Lys Glu Val Pro Lys Thr Thr Pro Ser Glu Pro Lys
                1315                1320                1325
Lys Lys Gln Pro Pro Pro Glu Ser Gly Pro Glu Gln Ser Lys Gln
                1330                1335                1340
Lys Lys Val Ala Pro Arg Pro Ser Ile Pro Val Lys Gln Lys Pro Lys
1345                1350                1355                1360
Glu Lys Glu Lys Pro Pro Pro Val Asn Lys Gln Glu Asn Ala Gly Thr
                1365                1370                1375
Leu Asn Ile Leu Ser Thr Leu Ser Asn Gly Asn Ser Ser Lys Gln Lys
                1380                1385                1390
Ile Pro Ala Asp Gly Val His Arg Ile Arg Val Asp Phe Lys Glu Asp
                1395                1400                1405
Cys Glu Ala Glu Asn Val Trp Glu Met Gly Gly Leu Gly Ile Leu Thr
                1410                1415                1420
Ser Val Pro Ile Thr Pro Arg Val Val Cys Phe Leu Cys Ala Ser Ser
1425                1430                1435                1440
Gly His Val Glu Phe Val Tyr Cys Gln Val Cys Cys Glu Pro Phe His
                1445                1450                1455
Lys Phe Cys Leu Glu Glu Asn Glu Arg Pro Leu Glu Asp Gln Leu Glu
                1460                1465                1470
Asn Trp Cys Cys Arg Arg Cys Lys Phe Cys His Val Cys Gly Arg Gln
                1475                1480                1485
His Gln Ala Thr Lys Gln Leu Leu Glu Cys Asn Lys Cys Arg Asn Ser
                1490                1495                1500
Tyr His Pro Glu Cys Leu Gly Pro Asn Tyr Pro Thr Lys Pro Thr Lys
1505                1510                1515                1520
Lys Lys Lys Val Trp Ile Cys Thr Lys Cys Val Arg Cys Lys Ser Cys
                1525                1530                1535
Gly Ser Thr Thr Pro Gly Lys Gly Trp Asp Ala Gln Trp Ser His Asp
                1540                1545                1550
Phe Ser Leu Cys His Asp Cys Ala Lys Leu Phe Ala Lys Gly Asn Phe
                1555                1560                1565
```

-continued

```
Cys Pro Leu Cys Asp Lys Cys Tyr Asp Asp Asp Tyr Glu Ser Lys
    1570            1575                1580
Met Met Gln Cys Gly Lys Cys Asp Arg Trp Val His Ser Lys Cys Glu
1585            1590                1595                1600
Asn Leu Ser Asp Glu Met Tyr Glu Ile Leu Ser Asn Leu Pro Glu Ser
            1605                1610                1615
Val Ala Tyr Thr Cys Val Asn Cys Thr Glu Arg His Pro Ala Glu Trp
        1620                1625                1630
Arg Leu Ala Leu Glu Lys Glu Leu Gln Ile Ser Leu Lys Gln Val Leu
            1635                1640                1645
Thr Ala Leu Leu Asn Ser Arg Thr Thr Ser His Leu Leu Arg Tyr Arg
        1650                1655                1660
Gln Ala Ala Lys Pro Pro Asp Leu Asn Pro Glu Thr Glu Glu Ser Ile
1665            1670                1675                1680
Pro Ser Arg Ser Ser Pro Glu Gly Pro Asp Pro Val Leu Thr Glu
            1685                1690                1695
Val Ser Lys Gln Asp Asp Gln Gln Pro Leu Asp Leu Glu Gly Val Lys
        1700                1705                1710
Arg Lys Met Asp Gln Gly Asn Tyr Thr Ser Val Leu Glu Phe Ser Asp
            1715                1720                1725
Asp Ile Val Lys Ile Ile Gln Ala Ala Ile Asn Ser Asp Gly Gly Gln
        1730                1735                1740
Pro Glu Ile Lys Lys Ala Asn Ser Met Val Lys Ser Phe Phe Ile Arg
1745            1750                1755                1760
Gln Met Glu Arg Val Phe Pro Trp Phe Ser Val Lys Lys Ser Arg Phe
            1765                1770                1775
Trp Glu Pro Asn Lys Val Ser Ser Asn Ser Gly Met Leu Pro Asn Ala
        1780                1785                1790
Val Leu Pro Pro Ser Leu Asp His Asn Tyr Ala Gln Trp Gln Glu Arg
            1795                1800                1805
Glu Glu Asn Ser His Thr Glu Gln Pro Pro Leu Met Lys Lys Ile Ile
        1810                1815                1820
Pro Ala Pro Lys Pro Lys Gly Pro Gly Glu Pro Asp Ser Pro Thr Pro
1825            1830                1835                1840
Leu His Pro Pro Thr Pro Pro Ile Leu Ser Thr Asp Arg Ser Arg Glu
            1845                1850                1855
Asp Ser Pro Glu Leu Asn Pro Pro Gly Ile Glu Asp Asn Arg Gln
        1860                1865                1870
Cys Ala Leu Cys Leu Thr Tyr Gly Asp Asp Ser Ala Asn Asp Ala Gly
            1875                1880                1885
Arg Leu Leu Tyr Ile Gly Gln Asn Glu Trp Thr His Val Asn Cys Ala
        1890                1895                1900
Leu Trp Ser Ala Glu Val Phe Glu Asp Asp Asp Gly Ser Leu Lys Asn
1905            1910                1915                1920
Val His Met Ala Val Ile Arg Gly Lys Gln Leu Arg Cys Glu Phe Cys
            1925                1930                1935
Gln Lys Pro Gly Ala Thr Val Gly Cys Cys Leu Thr Ser Cys Thr Ser
        1940                1945                1950
Asn Tyr His Phe Met Cys Ser Arg Ala Lys Asn Cys Val Phe Leu Asp
            1955                1960                1965
Asp Lys Lys Val Tyr Cys Gln Arg His Arg Asp Leu Ile Lys Gly Glu
        1970                1975                1980
Val Val Pro Glu Asn Gly Phe Glu Val Phe Arg Arg Val Phe Val Asp
1985            1990                1995                2000
```

```
Phe Glu Gly Ile Ser Leu Arg Arg Lys Phe Leu Asn Gly Leu Glu Pro
            2005                2010                2015
Glu Asn Ile His Met Met Ile Gly Ser Met Thr Ile Asp Cys Leu Gly
            2020                2025                2030
Ile Leu Asn Asp Leu Ser Asp Cys Glu Asp Lys Leu Phe Pro Ile Gly
            2035                2040                2045
Tyr Gln Cys Ser Arg Val Tyr Trp Ser Thr Thr Asp Ala Arg Lys Arg
            2050                2055                2060
Cys Val Tyr Thr Cys Lys Ile Val Glu Cys Arg Pro Pro Val Val Glu
2065                2070                2075                2080
Pro Asp Ile Asn Ser Thr Val Glu His Asp Glu Asn Arg Thr Ile Ala
            2085                2090                2095
His Ser Pro Thr Ser Phe Thr Gly Ser Ser Ser Lys Glu Ser Gln Asn
            2100                2105                2110
Thr Ala Glu Ile Ile Ser Pro Pro Ser Pro Asp Arg Pro Pro His Ser
            2115                2120                2125
Gln Thr Ser Gly Ser Cys Tyr Tyr His Val Ile Ser Lys Val Pro Arg
            2130                2135                2140
Ile Arg Thr Pro Ser Tyr Ser Pro Thr Gln Arg Ser Pro Gly Cys Arg
2145                2150                2155                2160
Pro Leu Pro Ser Ala Gly Ser Pro Thr Pro Thr Thr His Glu Ile Val
            2165                2170                2175
Thr Val Gly Asp Pro Leu Leu Ser Ser Gly Leu Arg Ser Ile Gly Ser
            2180                2185                2190
Arg Arg His Ser Thr Ser Ser Leu Ser Pro Gln Arg Ser Lys Leu Arg
            2195                2200                2205
Ile Met Ser Pro Met Arg Thr Gly Asn Thr Tyr Ser Arg Asn Asn Val
            2210                2215                2220
Ser Ser Val Ser Thr Thr Gly Thr Ala Thr Asp Leu Glu Ser Ser Ala
2225                2230                2235                2240
Lys Val Val Asp His Val Leu Gly Pro Leu Asn Ser Ser Thr Ser Leu
            2245                2250                2255
Gly Gln Asn Thr Ser Thr Ser Ser Asn Leu Gln Arg Thr Val Val Thr
            2260                2265                2270
Val Gly Asn Lys Asn Ser His Leu Asp Gly Ser Ser Ser Ser Glu Met
            2275                2280                2285
Lys Gln Ser Ser Ala Ser Asp Leu Val Ser Lys Ser Ser Ser Leu Lys
            2290                2295                2300
Gly Glu Lys Thr Lys Val Leu Ser Ser Lys Ser Ser Glu Gly Ser Ala
2305                2310                2315                2320
His Asn Val Ala Tyr Pro Gly Ile Pro Lys Leu Ala Pro Gln Val His
            2325                2330                2335
Asn Thr Thr Ser Arg Glu Leu Asn Val Ser Lys Ile Gly Ser Phe Ala
            2340                2345                2350
Glu Pro Ser Ser Val Ser Phe Ser Ser Lys Glu Ala Leu Ser Phe Pro
            2355                2360                2365
His Leu His Leu Arg Gly Gln Arg Asn Asp Arg Asp Gln His Thr Asp
            2370                2375                2380
Ser Thr Gln Ser Ala Asn Ser Ser Pro Asp Glu Asp Thr Glu Val Lys
2385                2390                2395                2400
Thr Leu Lys Leu Ser Gly Met Ser Asn Arg Ser Ser Ile Ile Asn Glu
            2405                2410                2415
His Met Gly Ser Ser Ser Arg Asp Arg Arg Gln Lys Gly Lys Lys Ser
```

```
                    2420            2425            2430
Cys Lys Glu Thr Phe Lys Glu Lys His Ser Ser Lys Ser Phe Leu Glu
            2435            2440            2445

Pro Gly Gln Val Thr Thr Gly Glu Glu Gly Asn Leu Lys Pro Glu Phe
            2450            2455            2460

Met Asp Glu Val Leu Thr Pro Glu Tyr Met Gly Gln Arg Pro Cys Asn
2465            2470            2475            2480

Asn Val Ser Ser Asp Lys Ile Gly Asp Lys Gly Leu Ser Met Pro Gly
            2485            2490            2495

Val Pro Lys Ala Pro Pro Met Gln Val Glu Gly Ser Ala Lys Glu Leu
            2500            2505            2510

Gln Ala Pro Arg Lys Arg Thr Val Lys Val Thr Leu Thr Pro Leu Lys
            2515            2520            2525

Met Glu Asn Glu Ser Gln Ser Lys Asn Ala Leu Lys Glu Ser Ser Pro
            2530            2535            2540

Ala Ser Pro Leu Gln Ile Glu Ser Thr Ser Pro Thr Glu Pro Ile Ser
2545            2550            2555            2560

Ala Ser Glu Asn Pro Gly Asp Gly Pro Val Ala Gln Pro Ser Pro Asn
            2565            2570            2575

Asn Thr Ser Cys Gln Asp Ser Gln Ser Asn Asn Tyr Gln Asn Leu Pro
            2580            2585            2590

Val Gln Asp Arg Asn Leu Met Leu Pro Asp Gly Pro Lys Pro Gln Glu
            2595            2600            2605

Asp Gly Ser Phe Lys Arg Arg Tyr Pro Arg Arg Ser Ala Arg Ala Arg
            2610            2615            2620

Ser Asn Met Phe Phe Gly Leu Thr Pro Leu Tyr Gly Val Arg Ser Tyr
2625            2630            2635            2640

Gly Glu Glu Asp Ile Pro Phe Tyr Ser Ser Ser Thr Gly Lys Lys Arg
            2645            2650            2655

Gly Lys Arg Ser Ala Glu Gly Gln Val Asp Gly Ala Asp Asp Leu Ser
            2660            2665            2670

Thr Ser Asp Glu Asp Asp Leu Tyr Tyr Tyr Asn Phe Thr Arg Thr Val
            2675            2680            2685

Ile Ser Ser Gly Gly Glu Glu Arg Leu Ala Ser His Asn Leu Phe Arg
            2690            2695            2700

Glu Glu Glu Gln Cys Asp Leu Pro Lys Ile Ser Gln Leu Asp Gly Val
2705            2710            2715            2720

Asp Asp Gly Thr Glu Ser Asp Thr Ser Val Thr Ala Thr Thr Arg Lys
            2725            2730            2735

Ser Ser Gln Ile Pro Lys Arg Asn Gly Lys Glu Asn Gly Thr Glu Asn
            2740            2745            2750

Leu Lys Ile Asp Arg Pro Glu Asp Ala Gly Glu Lys Glu His Val Thr
            2755            2760            2765

Lys Ser Ser Val Gly His Lys Asn Glu Pro Lys Met Asp Asn Cys His
            2770            2775            2780

Ser Val Ser Arg Val Lys Thr Gln Gly Gln Asp Ser Leu Glu Ala Gln
2785            2790            2795            2800

Leu Ser Ser Leu Glu Ser Ser Arg Arg Val His Thr Ser Thr Pro Ser
            2805            2810            2815

Asp Lys Asn Leu Leu Asp Thr Tyr Asn Thr Glu Leu Leu Lys Ser Asp
            2820            2825            2830

Ser Asp Asn Asn Asn Ser Asp Asp Cys Gly Asn Ile Leu Pro Ser Asp
            2835            2840            2845
```

-continued

Ile Met Asp Phe Val Leu Lys Asn Thr Pro Ser Met Gln Ala Leu Gly
              2850                2855                2860

Glu Ser Pro Glu Ser Ser Ser Glu Leu Leu Asn Leu Gly Glu Gly
2865                2870                2875                2880

Leu Gly Leu Asp Ser Asn Arg Glu Lys Asp Met Gly Leu Phe Glu Val
              2885                2890                2895

Phe Ser Gln Gln Leu Pro Thr Thr Glu Pro Val Asp Ser Ser Val Ser
              2900                2905                2910

Ser Ser Ile Ser Ala Glu Glu Gln Phe Glu Leu Pro Leu Glu Leu Pro
              2915                2920                2925

Ser Asp Leu Ser Val Leu Thr Thr Arg Ser Pro Thr Val Pro Ser Gln
              2930                2935                2940

Asn Pro Ser Arg Leu Ala Val Ile Ser Asp Ser Gly Glu Lys Arg Val
2945                2950                2955                2960

Thr Ile Thr Glu Lys Ser Val Ala Ser Ser Glu Ser Asp Pro Ala Leu
              2965                2970                2975

Leu Ser Pro Gly Val Asp Pro Thr Pro Glu Gly His Met Thr Pro Asp
              2980                2985                2990

His Phe Ile Gln Gly His Met Asp Ala Asp His Ile Ser Ser Pro Pro
              2995                3000                3005

Cys Gly Ser Val Glu Gln Gly His Gly Asn Asn Gln Asp Leu Thr Arg
              3010                3015                3020

Asn Ser Ser Thr Pro Gly Leu Gln Val Pro Val Ser Pro Thr Val Pro
3025                3030                3035                3040

Ile Gln Asn Gln Lys Tyr Val Pro Asn Ser Thr Asp Ser Pro Gly Pro
              3045                3050                3055

Ser Gln Ile Ser Asn Ala Ala Val Gln Thr Thr Pro Pro His Leu Lys
              3060                3065                3070

Pro Ala Thr Glu Lys Leu Ile Val Val Asn Gln Asn Met Gln Pro Leu
              3075                3080                3085

Tyr Val Leu Gln Thr Leu Pro Asn Gly Val Thr Gln Lys Ile Gln Leu
              3090                3095                3100

Thr Ser Ser Val Ser Ser Thr Pro Ser Val Met Glu Thr Asn Thr Ser
3105                3110                3115                3120

Val Leu Gly Pro Met Gly Gly Gly Leu Thr Leu Thr Thr Gly Leu Asn
              3125                3130                3135

Pro Ser Leu Pro Thr Ser Gln Ser Leu Phe Pro Ser Ala Ser Lys Gly
              3140                3145                3150

Leu Leu Pro Met Ser His His Gln His Leu His Ser Phe Pro Ala Ala
              3155                3160                3165

Thr Gln Ser Ser Phe Pro Pro Asn Ile Ser Asn Pro Pro Ser Gly Leu
              3170                3175                3180

Leu Ile Gly Val Gln Pro Pro Asp Pro Gln Leu Leu Val Ser Glu
3185                3190                3195                3200

Ser Ser Gln Arg Thr Asp Leu Ser Thr Thr Val Ala Thr Pro Ser Ser
              3205                3210                3215

Gly Leu Lys Lys Arg Pro Ile Ser Arg Leu Gln Thr Arg Lys Asn Lys
              3220                3225                3230

Lys Leu Ala Pro Ser Ser Thr Pro Ser Asn Ile Ala Pro Ser Asp Val
              3235                3240                3245

Val Ser Asn Met Thr Leu Ile Asn Phe Thr Pro Ser Gln Leu Pro Asn
              3250                3255                3260

His Pro Ser Leu Leu Asp Leu Gly Ser Leu Asn Thr Ser Ser His Arg
3265                3270                3275                3280

```
Thr Val Pro Asn Ile Ile Lys Arg Ser Lys Ser Ser Ile Met Tyr Phe
            3285                3290                3295

Glu Pro Ala Pro Leu Pro Gln Ser Val Gly Gly Thr Ala Ala Thr
            3300                3305                3310

Ala Ala Gly Thr Ser Thr Ile Ser Gln Asp Thr Ser His Leu Thr Ser
            3315                3320                3325

Gly Ser Val Ser Gly Leu Ala Ser Ser Ser Val Leu Asn Val Val
            3330                3335                3340

Ser Met Gln Thr Thr Thr Thr Pro Thr Ser Ser Ala Ser Val Pro Gly
3345                3350                3355                3360

His Val Thr Leu Thr Asn Pro Arg Leu Leu Gly Thr Pro Asp Ile Gly
            3365                3370                3375

Ser Ile Ser Asn Leu Leu Ile Lys Ala Ser Gln Gln Ser Leu Gly Ile
            3380                3385                3390

Gln Asp Gln Pro Val Ala Leu Pro Pro Ser Ser Gly Met Phe Pro Gln
            3395                3400                3405

Leu Gly Thr Ser Gln Thr Pro Ser Thr Ala Ala Ile Thr Ala Ala Ser
            3410                3415                3420

Ser Ile Cys Val Leu Pro Ser Thr Gln Thr Thr Gly Ile Thr Ala Ala
3425                3430                3435                3440

Ser Pro Ser Gly Glu Ala Asp Glu His Tyr Gln Leu Gln His Val Asn
            3445                3450                3455

Gln Leu Leu Ala Ser Lys Thr Gly Ile His Ser Ser Gln Arg Asp Leu
            3460                3465                3470

Asp Ser Ala Ser Gly Pro Gln Val Ser Asn Phe Thr Gln Thr Val Asp
            3475                3480                3485

Ala Pro Asn Ser Met Gly Leu Glu Gln Asn Lys Ala Leu Ser Ser Ala
            3490                3495                3500

Val Gln Ala Ser Pro Thr Ser Pro Gly Gly Ser Pro Ser Ser Pro Ser
3505                3510                3515                3520

Ser Gly Gln Arg Ser Ala Ser Pro Ser Val Pro Gly Pro Thr Lys Pro
            3525                3530                3535

Lys Pro Lys Thr Lys Arg Phe Gln Leu Pro Leu Asp Lys Gly Asn Gly
            3540                3545                3550

Lys Lys His Lys Val Ser His Leu Arg Thr Ser Ser Ser Glu Ala His
            3555                3560                3565

Ile Pro Asp Gln Glu Thr Thr Ser Leu Thr Ser Gly Thr Gly Thr Pro
            3570                3575                3580

Gly Ala Glu Ala Glu Gln Gln Asp Thr Ala Ser Val Glu Gln Ser Ser
3585                3590                3595                3600

Gln Lys Glu Cys Gly Gln Pro Ala Gly Gln Val Ala Val Leu Pro Glu
            3605                3610                3615

Val Gln Val Thr Gln Asn Pro Ala Asn Glu Gln Glu Ser Ala Glu Pro
            3620                3625                3630

Lys Thr Val Glu Glu Glu Glu Ser Asn Phe Ser Ser Pro Leu Met Leu
            3635                3640                3645

Trp Leu Gln Gln Glu Gln Lys Arg Lys Glu Ser Ile Thr Glu Lys Lys
            3650                3655                3660

Pro Lys Lys Gly Leu Val Phe Glu Ile Ser Ser Asp Asp Gly Phe Gln
3665                3670                3675                3680

Ile Cys Ala Glu Ser Ile Glu Asp Ala Trp Lys Ser Leu Thr Asp Lys
            3685                3690                3695

Val Gln Glu Ala Arg Ser Asn Ala Arg Leu Lys Gln Leu Ser Phe Ala
```

-continued

```
                  3700            3705                3710
Gly Val Asn Gly Leu Arg Met Leu Gly Ile Leu His Asp Ala Val Val
            3715                3720                3725

Phe Leu Ile Glu Gln Leu Ser Gly Ala Lys His Cys Arg Asn Tyr Lys
        3730                3735            3740

Phe Arg Phe His Lys Pro Glu Glu Ala Asn Glu Pro Pro Leu Asn Pro
3745                3750                3755            3760

His Gly Ser Ala Arg Ala Glu Val His Leu Arg Lys Ser Ala Phe Asp
                3765                3770            3775

Met Phe Asn Phe Leu Ala Ser Lys His Arg Gln Pro Pro Glu Tyr Asn
            3780                3785                3790

Pro Asn Asp Glu Glu Glu Glu Val Gln Leu Lys Ser Ala Arg Arg
            3795                3800            3805

Ala Thr Ser Met Asp Leu Pro Met Pro Met Arg Phe Arg His Leu Lys
        3810                3815            3820

Lys Thr Ser Lys Glu Ala Val Gly Val Tyr Arg Ser Pro Ile His Gly
3825                3830                3835                3840

Arg Gly Leu Phe Cys Lys Arg Asn Ile Asp Ala Gly Glu Met Val Ile
                3845                3850                3855

Glu Tyr Ala Gly Asn Val Ile Arg Ser Ile Gln Thr Asp Lys Arg Glu
            3860                3865                3870

Lys Tyr Tyr Asp Ser Lys Gly Ile Gly Cys Tyr Met Phe Arg Ile Asp
            3875                3880                3885

Asp Ser Glu Val Val Asp Ala Thr Met His Gly Asn Arg Ala Arg Phe
3890                3895                3900

Ile Asn His Ser Cys Glu Pro Asn Cys Tyr Ser Arg Val Ile Asn Ile
3905                3910                3915                3920

Asp Gly Gln Lys His Ile Val Ile Phe Ala Met Arg Lys Ile Tyr Arg
                3925                3930                3935

Gly Glu Glu Leu Thr Tyr Asp Tyr Lys Phe Pro Ile Glu Asp Ala Ser
                3940                3945                3950

Asn Lys Leu Pro Cys Asn Cys Gly Ala Lys Lys Cys Arg Lys Phe Leu
            3955                3960                3965

Asn
```